US012582164B2

(12) United States Patent
Novak, III et al.

(10) Patent No.:  US 12,582,164 B2
(45) Date of Patent:       Mar. 24, 2026

(54) AEROSOL DELIVERY DEVICE WITH IMPROVED CONNECTIVITY, AIRFLOW, AND AEROSOL PATHS

(71) Applicant: RAI Strategic Holdings, Inc., Winston-Salem, NC (US)

(72) Inventors: Charles Jacob Novak, III, Winston-Salem, NC (US); Sean A. Daugherty, Yadkinville, NC (US); Jared Aller, Winston-Salem, NC (US); Michael Ryan Galloway, Winston-Salem, NC (US); Justin Holt, Winston-Salem, NC (US); Matthew Joel Nettenstrom, Bartlett, IL (US); Steven Michael Schennum, Plainfield, IL (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 347 days.

(21) Appl. No.: 18/096,325

(22) Filed: Jan. 12, 2023

(65) Prior Publication Data

US 2023/0178949 A1      Jun. 8, 2023

Related U.S. Application Data

(63) Continuation of application No. 16/598,496, filed on Oct. 10, 2019, now Pat. No. 11,588,287.

(Continued)

(51) Int. Cl.
*A24F 40/42*        (2020.01)
*A61M 11/04*        (2006.01)
(Continued)

(52) U.S. Cl.
CPC ........... *A24F 40/42* (2020.01); *A61M 11/042* (2014.02); *H05B 3/06* (2013.01); *H05B 3/22* (2013.01);
(Continued)

(58) Field of Classification Search
CPC .... H05B 3/06; H05B 3/22; A61M 2205/0288; A61M 11/042; A24F 40/10; A24F 40/20; A24F 40/40; A24F 40/42
See application file for complete search history.

(56) References Cited

U.S. PATENT DOCUMENTS 2,057,353 A     10/1936   Whittemore, Jr.
2,104,266 A      1/1938   McCormick
(Continued)

FOREIGN PATENT DOCUMENTS

CN          1541577        11/2004
CN          2719043         8/2005
(Continued)

OTHER PUBLICATIONS

CN 107890142 Translation and Original (Year: 2018).*

*Primary Examiner* — Marcus E Harcum
(74) *Attorney, Agent, or Firm* — Womble Bond Dickinson (US) LLP

(57) ABSTRACT

The present disclosure provides an aerosol delivery device and a cartridge for an aerosol delivery device. In various implementations, the aerosol delivery device comprises a control device that includes an outer housing defining a cartridge receiving chamber, and further includes a power source and a control component, and a cartridge that includes a mouthpiece, a tank, a heating assembly, and a bottom cap. The mouthpiece defines an exit portal in an end thereof, and the tank is configured to contain a liquid composition therein. The cartridge is configured to be (Continued)

removably coupled with the receiving chamber of the control device, and the heating assembly defines a vaporization chamber and is configured to heat the liquid composition to generate an aerosol. An inlet airflow is defined by a gap between the cartridge and the control device that originates at an interface between an outer peripheral surface the mouthpiece and control device.

15 Claims, 38 Drawing Sheets

Related U.S. Application Data

(60) Provisional application No. 62/911,519, filed on Oct. 7, 2019, provisional application No. 62/744,978, filed on Oct. 12, 2018.

(51) Int. Cl.

| | |
|---|---|
| *H05B 3/06* | (2006.01) |
| *H05B 3/22* | (2006.01) |
| *H05B 3/46* | (2006.01) |
| *H01R 13/00* | (2006.01) |
| *H01R 13/62* | (2006.01) |
| *H01R 31/06* | (2006.01) |
| *H01R 33/18* | (2006.01) |

(52) U.S. Cl.
CPC ....... *H05B 3/46* (2013.01); *A61M 2205/0288* (2013.01); *A61M 2205/3331* (2013.01); *H01R 13/005* (2013.01); *H01R 13/6205* (2013.01); *H01R 31/06* (2013.01); *H01R 33/18* (2013.01)

(56) References Cited

U.S. PATENT DOCUMENTS

| | | | |
|---|---|---|---|
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,894,841 | A | 4/1999 | Voges |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 8,528,569 | B1 | 9/2013 | Newton |
| 8,833,364 | B2 | 9/2014 | Buchberger |
| 8,950,395 | B2 | 2/2015 | Schennum |
| 9,220,304 | B2 | 12/2015 | Greim |
| 9,462,831 | B2 | 10/2016 | Liu |
| 9,877,508 | B2 | 1/2018 | Kane |
| 10,015,990 | B2 | 7/2018 | Mironov |
| 10,028,537 | B1 | 7/2018 | Hawes et al. |
| 10,058,125 | B2 | 8/2018 | Worm et al. |
| 10,080,851 | B2 | 9/2018 | Davidson et al. |
| 10,085,481 | B2 | 10/2018 | Verleur et al. |
| 10,092,037 | B2 | 10/2018 | Tucker et al. |
| 10,104,913 | B2 | 10/2018 | Lau et al. |
| 10,117,463 | B2 | 11/2018 | Thomas |
| 10,117,467 | B2 | 11/2018 | Hawes et al. |
| 10,779,575 | B2 | 9/2020 | Qiu |
| 11,185,110 | B2 | 11/2021 | Fraser et al. |
| 2005/0016550 | A1 | 1/2005 | Katase |
| 2006/0196518 | A1 | 9/2006 | Hon |
| 2008/0092912 | A1 | 4/2008 | Robinson et al. |
| 2009/0095311 | A1 | 4/2009 | Hon |
| 2009/0126745 | A1 | 5/2009 | Hon |
| 2009/0151717 | A1 | 6/2009 | Bowen et al. |
| 2009/0188490 | A1 | 7/2009 | Hon |
| 2009/0272379 | A1 | 11/2009 | Thorens et al. |
| 2009/0320863 | A1 | 12/2009 | Fernando et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2013/0037041 | A1 | 2/2013 | Worm et al. |
| 2013/0042865 | A1 | 2/2013 | Monsees et al. |
| 2013/0306084 | A1 | 11/2013 | Flick |
| 2013/0319435 | A1 | 12/2013 | Flick |
| 2014/0000638 | A1 | 1/2014 | Sebastian et al. |
| 2014/0096781 | A1 | 4/2014 | Sears et al. |
| 2014/0096782 | A1 | 4/2014 | Ampolini et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0366898 | A1 | 12/2014 | Monsees et al. |
| 2015/0020832 | A1 | 1/2015 | Greim et al. |
| 2015/0117841 | A1 | 4/2015 | Brammer et al. |
| 2015/0128976 | A1 | 5/2015 | Verleur et al. |
| 2015/0150308 | A1 | 6/2015 | Monsees et al. |
| 2015/0164142 | A1 | 6/2015 | Li et al. |
| 2015/0208729 | A1 | 7/2015 | Monsees et al. |
| 2015/0216233 | A1 | 8/2015 | Sears et al. |
| 2015/0305406 | A1 | 10/2015 | Li et al. |
| 2015/0313287 | A1 | 11/2015 | Verleur et al. |
| 2016/0050975 | A1 | 2/2016 | Worm et al. |
| 2016/0278436 | A1 | 9/2016 | Verleur et al. |
| 2016/0366947 | A1 | 12/2016 | Monsees et al. |
| 2017/0027226 | A1 | 2/2017 | Mironov et al. |
| 2017/0071256 | A1 | 3/2017 | Verleur et al. |
| 2017/0095005 | A1 | 4/2017 | Monsees et al. |
| 2017/0105452 | A1 | 4/2017 | Mironov et al. |
| 2017/0135404 | A1 | 5/2017 | Reevell |
| 2017/0135405 | A1 | 5/2017 | Reevell |
| 2017/0143042 | A1 | 5/2017 | Batista et al. |
| 2017/0215485 | A1 | 8/2017 | Zitzke |
| 2017/0231281 | A1 | 8/2017 | Hatton et al. |
| 2017/0231282 | A1 | 8/2017 | Hatton et al. |
| 2017/0325289 | A1 | 11/2017 | Liu |
| 2017/0340011 | A1 | 11/2017 | Batista |
| 2017/0340012 | A1 | 11/2017 | Mironov et al. |
| 2017/0347711 | A1 | 12/2017 | Litten et al. |
| 2017/0347712 | A1 | 12/2017 | Singh |
| 2017/0357402 | A1 | 12/2017 | Lau et al. |
| 2018/0000157 | A1 | 1/2018 | Batista et al. |
| 2018/0000160 | A1 | 1/2018 | Taschner et al. |
| 2018/0014575 | A1 | 1/2018 | Fursa |
| 2018/0020731 | A1 | 1/2018 | Rasmussen et al. |
| 2018/0020736 | A1 | 1/2018 | Silvestrini |
| 2018/0035717 | A1 | 2/2018 | Batista |
| 2018/0042306 | A1 | 2/2018 | Atkins et al. |
| 2018/0043114 | A1 | 2/2018 | Bowen et al. |
| 2018/0070644 | A1 | 3/2018 | Monsees et al. |
| 2018/0077967 | A1 | 3/2018 | Hatton et al. |
| 2018/0084831 | A1 | 3/2018 | Mironov |
| 2018/0103685 | A1 | 4/2018 | Yener |
| 2018/0132525 | A1 | 5/2018 | Patil et al. |
| 2018/0140019 | A1 | 5/2018 | Guo et al. |
| 2018/0168225 | A1 | 6/2018 | Zinovik et al. |
| 2018/0177230 | A1 | 6/2018 | Hawes et al. |
| 2018/0213845 | A1 | 8/2018 | Qiu |
| 2018/0213850 | A1 | 8/2018 | Brinkley et al. |
| 2018/0228214 | A1 | 8/2018 | McAdam et al. |
| 2018/0242643 | A1 | 8/2018 | Silvestrini et al. |
| 2018/0280637 | A1 | 10/2018 | Mayle et al. |
| 2018/0295888 | A1 | 10/2018 | Newcomb et al. |
| 2018/0296777 | A1 | 10/2018 | Terry et al. |
| 2019/0083720 | A1 | 3/2019 | Leadley et al. |
| 2019/0297953 | A1 | 10/2019 | Qiu et al. |
| 2020/0077702 | A1 | 3/2020 | Mishra et al. |
| 2020/0113239 | A1 | 4/2020 | Aller et al. |
| 2020/0288775 | A1 | 9/2020 | Wright et al. |
| 2020/0316325 | A1 | 10/2020 | Reevell |

(56)              References Cited

U.S. PATENT DOCUMENTS

FOREIGN PATENT DOCUMENTS

| | | | |
|---|---|---|---|
| CN | 201379072 | | 1/2010 |
| CN | 106263031 | | 1/2017 |
| CN | 107427072 | A | 12/2017 |
| CN | 10789142 | | 4/2018 |
| CN | 113455703 | | 10/2021 |
| EP | 1 618 803 | | 1/2006 |
| EP | 2 779 851 | B1 | 10/2016 |
| JP | 2018-527901 | A | 9/2018 |
| KR | 20130084789 | A | 7/2013 |
| TW | 201825827 | | 7/2018 |
| WO | WO 2004/080216 | | 9/2004 |
| WO | WO 2005/099494 | | 10/2005 |
| WO | WO 2007/131449 | | 11/2007 |
| WO | 20150071703 | A1 | 5/2015 |
| WO | 2016/005533 | A1 | 1/2016 |
| WO | WO 2016/026811 | | 2/2016 |
| WO | 2016135331 | A1 | 9/2016 |
| WO | WO 2017/051006 | | 9/2016 |
| WO | 2016/154792 | A1 | 10/2016 |
| WO | WO 2016/154797 | | 10/2016 |
| WO | 20170055803 | A1 | 4/2017 |
| WO | WO 2016/207442 | | 5/2017 |
| WO | 2017/102969 | A1 | 6/2017 |
| WO | WO 2017/163046 | | 9/2017 |
| WO | WO 2018/167166 | | 9/2018 |
| WO | WO 2018/202732 | | 11/2018 |
| WO | WO 2020/075139 | | 4/2020 |
| WO | WO 2021/127277 | | 6/2021 |
| WO | WO 2021/255209 | | 12/2021 |

* cited by examiner

300

302

310

326

AEROSOL DELIVERY DEVICE WITH IMPROVED CONNECTIVITY, AIRFLOW, AND AEROSOL PATHS

CROSS-REFERENCE TO RELATED APPLICATIONS

This application is a continuation of U.S. patent application Ser. No. 16/598,496, titled Aerosol Delivery Device with Improved Connectivity, Airflow, And Aerosol Paths, filed on Oct. 10, 2019, which claims priority to, and the benefit of, U.S. Provisional Patent Application No. 62/744,978, titled Aerosol Forming Device, filed on Oct. 12, 2018, and U.S. Provisional Patent Application No. 62/911,519, titled Aerosol Delivery Device with Improved Connectivity, Airflow, and Aerosol Paths, filed on Oct. 7, 2019, each of which is incorporated herein in its entirety by reference.

TECHNOLOGY FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety. It would be desirable to provide an aerosol delivery device with advantageous usability features.

BRIEF SUMMARY

The present disclosure relates to aerosol delivery devices, methods of forming such devices, and elements of such devices. The disclosure particularly relates to an aerosol delivery device and a cartridge for use in an aerosol delivery device. In this regard, various embodiments of the disclosure provide an aerosol delivery device and/or a cartridge with advantageous usability features. The present disclosure includes, without limitation, the following example implementations:

An aerosol delivery device comprising a control device that includes an outer housing defining an outer wall and having a proximal end and a distal end, the proximal end of the control device defining a receiving chamber, the control device further including a power source and a control component, and a cartridge that includes a mouthpiece, a tank, a heating assembly, and a bottom cap, the mouthpiece having a proximal end and a distal end, the proximal end of the mouthpiece having an exit portal defined therethrough, the tank defining a proximal end and a distal end and being configured to contain a liquid composition, the mouthpiece being configured to engage the proximal end of the tank, and the bottom cap being configured to engage the distal end of the tank, wherein the cartridge is configured to be removably coupled with the receiving chamber of the control device, wherein the heating assembly defines a vaporization chamber and is configured to heat the liquid composition to generate an aerosol, wherein an inlet airflow is defined by a gap between the cartridge and the control device, wherein an aerosol path is defined through the tank and the exit portal of the mouthpiece, and wherein the gap originates at an interface between an outer peripheral surface the mouthpiece and the control device.

The aerosol delivery device of any preceding example implementation, or any combination of any preceding example implementations, wherein the interface is located proximate an outer peripheral surface of the mouthpiece and a top edge of the outer wall of the housing.

The aerosol delivery device of any preceding example implementation, or any combination of any preceding example implementations, wherein the inlet airflow enters the cartridge through a single inlet channel located in an approximate center of a bottom surface of the bottom cap.

The aerosol delivery device of any preceding example implementation, or any combination of any preceding example implementations, wherein the inlet channel located in the bottom cap has a nozzle-like shape.

The aerosol delivery device of any preceding example implementation, or any combination of any preceding example implementations, wherein the gap between the cartridge and the control device is established by a plurality of protuberances located on the control device.

The aerosol delivery device of any preceding example implementation, or any combination of any preceding example implementations, wherein the plurality of protuberances comprises a plurality of raised elongate bosses located on an upper frame of the control device.

The aerosol delivery device of any preceding example implementation, or any combination of any preceding example implementations, wherein the gap between the cartridge and the control device is established between the outer housing and upper frame of the control device and the mouthpiece, tank, and bottom cap of the cartridge.

The aerosol delivery device of any preceding example implementation, or any combination of any preceding example implementations, wherein the gap between the cartridge and the control device is further established between a recessed surface of the upper frame of the control device and a bottom surface of the bottom cap of the cartridge.

The aerosol delivery device of any preceding example implementation, or any combination of any preceding example implementations, wherein the heating assembly comprises a flat heating member and a liquid transport element, and wherein the flat heating member and the liquid transport element are installed in a curved orientation.

The aerosol delivery device of any preceding example implementation, or any combination of any preceding example implementations, wherein the cartridge further defines a vaporization chamber defined by the bottom cap and heating assembly.

The aerosol delivery device of any preceding example implementation, or any combination of any preceding example implementations, wherein the aerosol path originates at the vaporization chamber.

The aerosol delivery device of any preceding example implementation, or any combination of any preceding example implementations, wherein inlet air entering the vaporization chamber impinges on the heating member substantially perpendicularly thereto and spreads out substantially horizontally.

The aerosol delivery device of any preceding example implementation, or any combination of any preceding example implementations, wherein the tank further defines a reservoir cavity configured to hold the liquid composition.

The aerosol delivery device of any preceding example implementation, or any combination of any preceding example implementations, wherein the aerosol path is defined by a pair of flow tubes located in the tank, and wherein at least a portion of the flow tubes are located on opposite sides of the reservoir cavity.

The aerosol delivery device of any preceding example implementation, or any combination of any preceding example implementations, wherein the reservoir cavity defines a closed proximate end and an open distal end.

The aerosol delivery device of any preceding example implementation, or any combination of any preceding example implementations, wherein the open distal end of the reservoir cavity of the cartridge is sealed at least in part by a separate base member.

The aerosol delivery device of any preceding example implementation, or any combination of any preceding example implementations, wherein the base member includes a plurality of slots configured to provide liquid flow passages.

The aerosol delivery device of any preceding example implementation, or any combination of any preceding example implementations, wherein the aerosol path is further defined through an upper aerosol channel insert located between the tank and the exit portal of the mouthpiece.

The aerosol delivery device of any preceding example implementation, or any combination of any preceding example implementations, wherein the bottom cap of the cartridge includes a pair of inserts comprising a ferromagnetic metal material.

The aerosol delivery device of any preceding example implementation, or any combination of any preceding example implementations, wherein an upper frame of the control device includes a pair of magnets configured to substantially align with the pair of metal inserts of the cartridge.

The aerosol delivery device of any preceding example implementation, or any combination of any preceding example implementations, wherein the control device includes a pressure sensor, and wherein the cartridge and the control device include a pressure path configured to signal a negative pressure to the pressure sensor.

The aerosol delivery device of any preceding example implementation, or any combination of any preceding example implementations, wherein the pressure path is defined at least in part by an offset pressure channel defined in the bottom cap of the cartridge.

The aerosol delivery device of any preceding example implementation, or any combination of any preceding example implementations, wherein the pressure path is defined at least in part by a corresponding channel in an upper frame seal of the control device.

The aerosol delivery device of any preceding example implementation, or any combination of any preceding example implementations, wherein the upper frame seal includes a pair of channels such that the pressure path is configured to be established in either of two rotational orientations of the cartridge.

The aerosol delivery device of any preceding example implementation, or any combination of any preceding example implementations, wherein the top edge of the outer wall of the housing defines an opening that is greater in size than the outer peripheral surface of the mouthpiece such that a maximum perimeter of the cartridge is wholly received within the receiving chamber.

The aerosol delivery device of any preceding example implementation, or any combination of any preceding example implementations, wherein when coupled to the control device, a portion of the mouthpiece extends below the top edge of the outer wall of the housing and into the receiving chamber.

A cartridge for use with an aerosol delivery device, the cartridge comprising a mouthpiece having a proximal end and a distal end, the proximal end having an exit portal defined therethrough, a tank having a proximal end and a distal end and being configured to contain a liquid composition therein, a heating assembly defining a vaporization chamber configured to heat the liquid composition to generate an aerosol, a reservoir cavity configured to hold the liquid composition, and a bottom cap, wherein the mouthpiece is configured to engage the proximal end of the tank and the bottom cap is configured to engage the distal end of the tank, wherein an inlet airflow enters the cartridge through a single inlet channel located in an approximate center of a bottom surface of the bottom cap, wherein an aerosol path is defined through the tank and the exit portal of the mouthpiece, wherein the aerosol path is defined by a pair of flow tubes located in the tank, and wherein at least a portion of the flow tubes are located on opposite sides of the reservoir cavity.

The cartridge of any preceding example implementation, or any combination of any preceding example implementations, wherein the inlet channel located in the bottom cap has a nozzle-like shape.

The cartridge of any preceding example implementation, or any combination of any preceding example implementations, wherein the heating assembly comprises a flat heating member and a liquid transport element, and wherein the flat heating member and the liquid transport element are installed in a curved orientation.

The cartridge of any preceding example implementation, or any combination of any preceding example implementations, wherein the cartridge further defines a vaporization chamber defined by the bottom cap and heating assembly.

The cartridge of any preceding example implementation, or any combination of any preceding example implementations, wherein the aerosol path originates at the vaporization chamber.

The cartridge of any preceding example implementation, or any combination of any preceding example implementations, wherein inlet air entering the vaporization chamber impinges on the heating member substantially perpendicularly thereto and spreads out substantially horizontally.

The cartridge of any preceding example implementation, or any combination of any preceding example implementations, wherein the reservoir cavity defines a closed proximate end and an open distal end.

The cartridge of any preceding example implementation, or any combination of any preceding example implementations, wherein the open distal end of the reservoir cavity is sealed at least in part by a separate base member.

The cartridge of any preceding example implementation, or any combination of any preceding example implementations, wherein the base member includes a plurality of slots configured to provide liquid flow passages.

The cartridge of any preceding example implementation, or any combination of any preceding example implementations, wherein the aerosol path is further defined through an upper aerosol channel insert located between the tank and the exit portal of the mouthpiece.

The cartridge of any preceding example implementation, or any combination of any preceding example implementations, wherein the bottom cap includes a pair of inserts comprising a ferromagnetic metal material.

The cartridge of any preceding example implementation, or any combination of any preceding example implementations, wherein a pressure path is defined at least in part by an offset pressure channel defined in the bottom cap of the cartridge.

An aerosol delivery device comprising a control device that includes an outer housing defining an outer wall and having a proximal end and a distal end, the proximal end of the control device defining a receiving chamber, the control device further including a power source and a control component, and a cartridge that includes a mouthpiece, a tank, and a heating assembly, the tank being configured to contain a liquid composition, wherein the cartridge is configured to be removably coupled with the receiving chamber of the control device, wherein the heating assembly is configured to heat the liquid composition to generate an aerosol, wherein the heating assembly comprises a substantially planar heating member and a liquid transport element, and wherein the heating member is installed in a bowed orientation.

The aerosol delivery device of any preceding example implementation, or any combination of any preceding example implementations, wherein the heating member comprises a first end, a second end, and a heater loop connecting the first end and the second end.

The aerosol delivery device of any preceding example implementation, or any combination of any preceding example implementations, wherein the heater loop comprises a serpentine pattern of connected heater traces that extend substantially transverse to a longitudinal axis of the heating member.

The aerosol delivery device of any preceding example implementation, or any combination of any preceding example implementations, wherein the serpentine pattern of heater traces comprises a plurality of split traces located in a central area of the heating member.

The aerosol delivery device of any preceding example implementation, or any combination of any preceding example implementations, wherein the heater loop is configured to concentrate heat in the area of the heating element in contact with the liquid transport element.

The aerosol delivery device of any preceding example implementation, or any combination of any preceding example implementations, further comprising a base member into which the heating member and the liquid transport element are disposed.

The aerosol delivery device of any preceding example implementation, or any combination of any preceding example implementations, wherein at least one edge of the heating member is configured to engage the base member to facilitate the bowed orientation of the heating member.

The aerosol delivery device of any preceding example implementation, or any combination of any preceding example implementations, further comprising a pair of connectors configured to electrically connect the cartridge with one or more of the control component or the power source.

The aerosol delivery device of any preceding example implementation, or any combination of any preceding example implementations, wherein the heating element includes a pair of contact holes configured to connect the heating member to the connectors.

The aerosol delivery device of any preceding example implementation, or any combination of any preceding example implementations, wherein each of the contact holes include one or more extensions that create an effective inner diameter that is less than an outer diameter of the mating connector.

A cartridge for use with an aerosol delivery device, the cartridge comprising a mouthpiece, a tank configured to contain a liquid composition, and a heating assembly, wherein the heating assembly is configured to heat the liquid composition to generate an aerosol, wherein the heating assembly comprises a substantially planar heating member and a liquid transport element, and wherein the heating member is installed in a curved orientation.

The cartridge of any preceding example implementation, or any combination of any preceding example implementations, wherein the heating member comprises a first end, a second end, and a heater loop connecting the first end and the second end.

The cartridge of any preceding example implementation, or any combination of any preceding example implementations, wherein the heater loop comprises a serpentine pattern of connected heater traces that extend substantially transverse to a longitudinal axis of the heating member.

The cartridge of any preceding example implementation, or any combination of any preceding example implementations, wherein the serpentine pattern of heater traces comprises a plurality of split traces located in a central area of the heating member.

The cartridge of any preceding example implementation, or any combination of any preceding example implementations, wherein the heater loop is configured to concentrate heat in the area of the heating element in contact with the liquid transport element.

The cartridge of any preceding example implementation, or any combination of any preceding example implementations, further comprising a base member into which the heating member and the liquid transport element are disposed.

The cartridge of any preceding example implementation, or any combination of any preceding example implementations, wherein at least one edge of the heating member is configured to engage the base member to facilitate the bowed orientation of the heating member. The cartridge of any preceding example implementation, or any combination of any preceding example implementations, further comprising a pair of connectors configured to electrically connect the cartridge with a control device.

The cartridge of any preceding example implementation, or any combination of any preceding example implementations, wherein the heating element includes a pair of contact holes configured to connect the heating member to the connectors.

The cartridge of any preceding example implementation, or any combination of any preceding example implementations, wherein each of the contact holes include one or more extensions that create an effective inner diameter that is less than an outer diameter of the mating connector.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
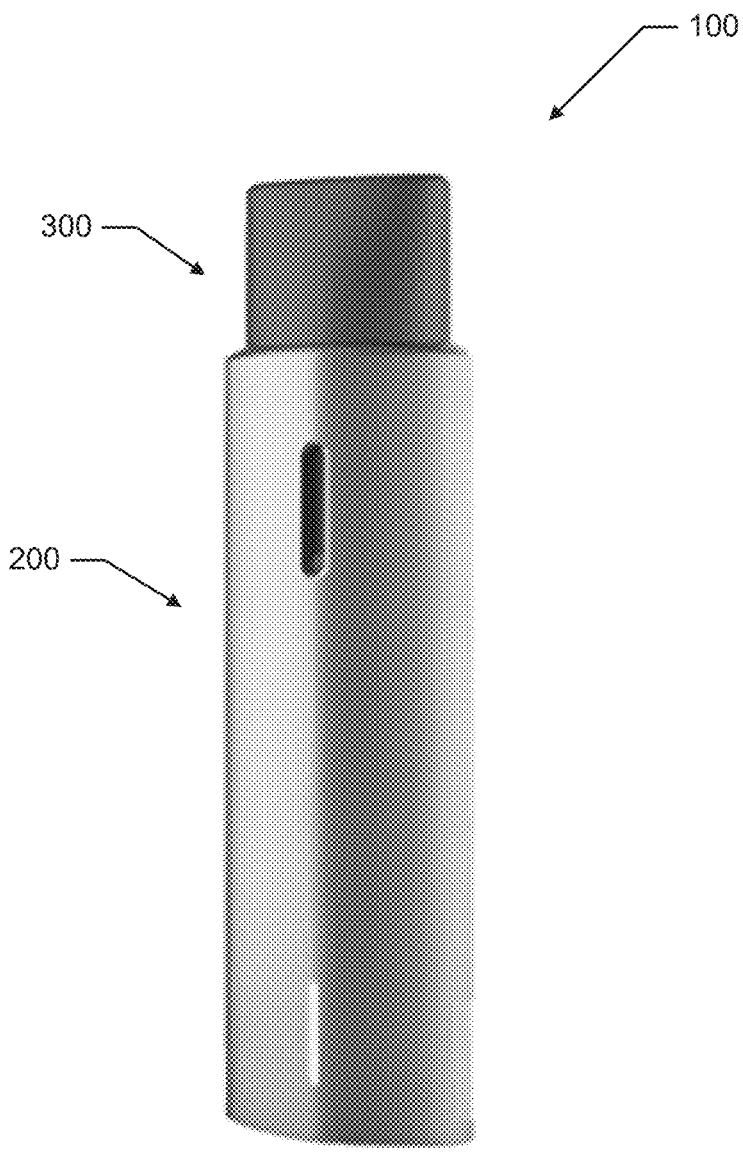
Figure 2:
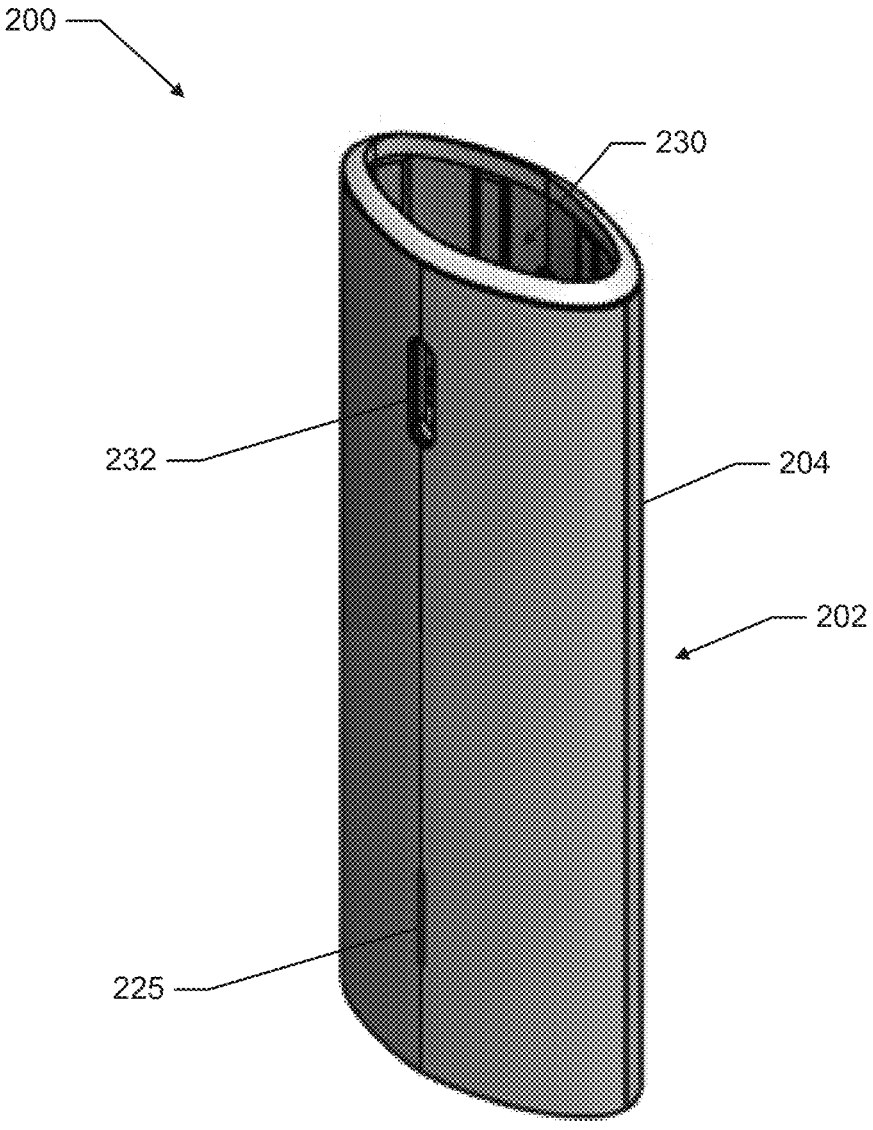
Figure 3:
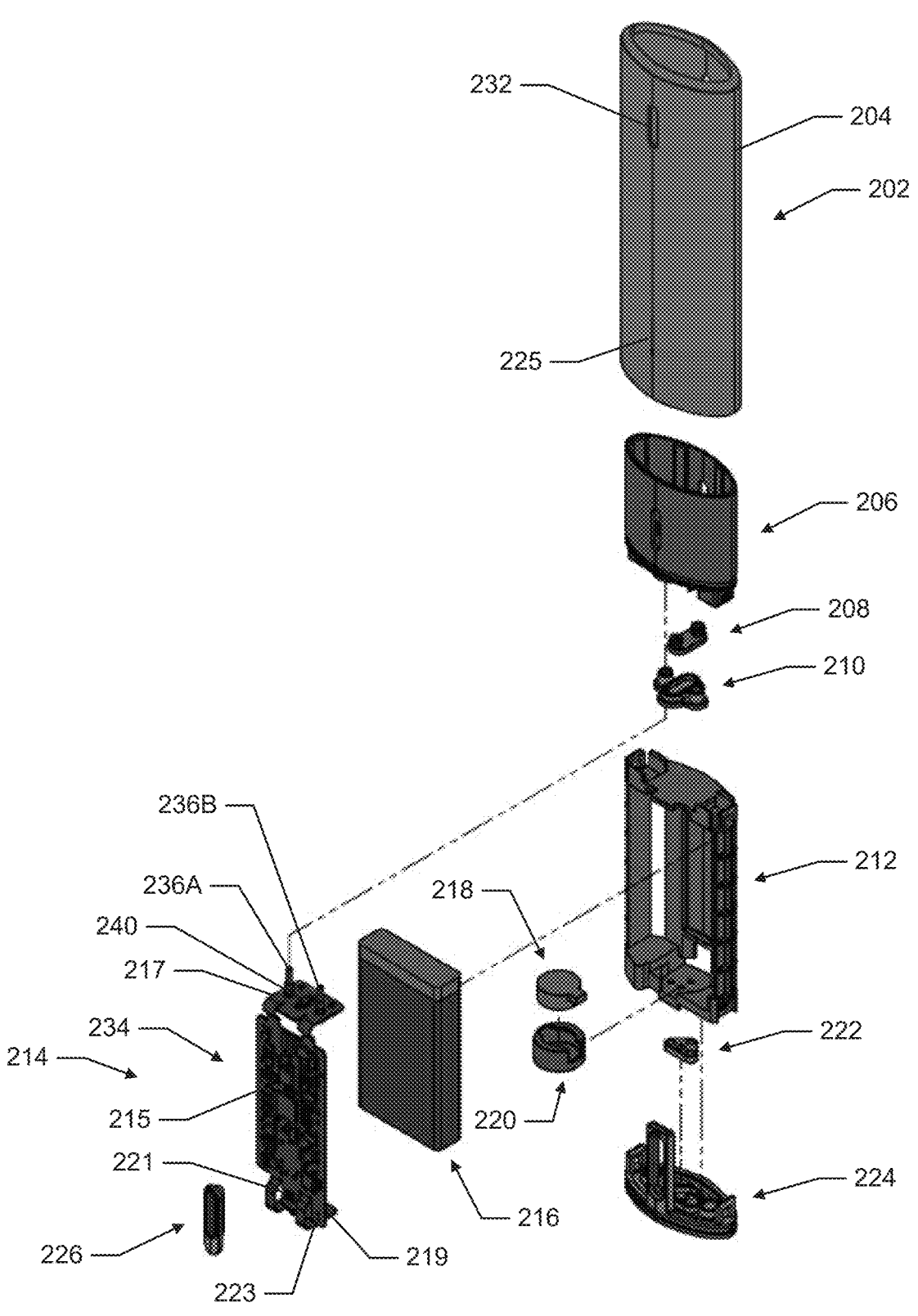
Figures 4A, 4B:
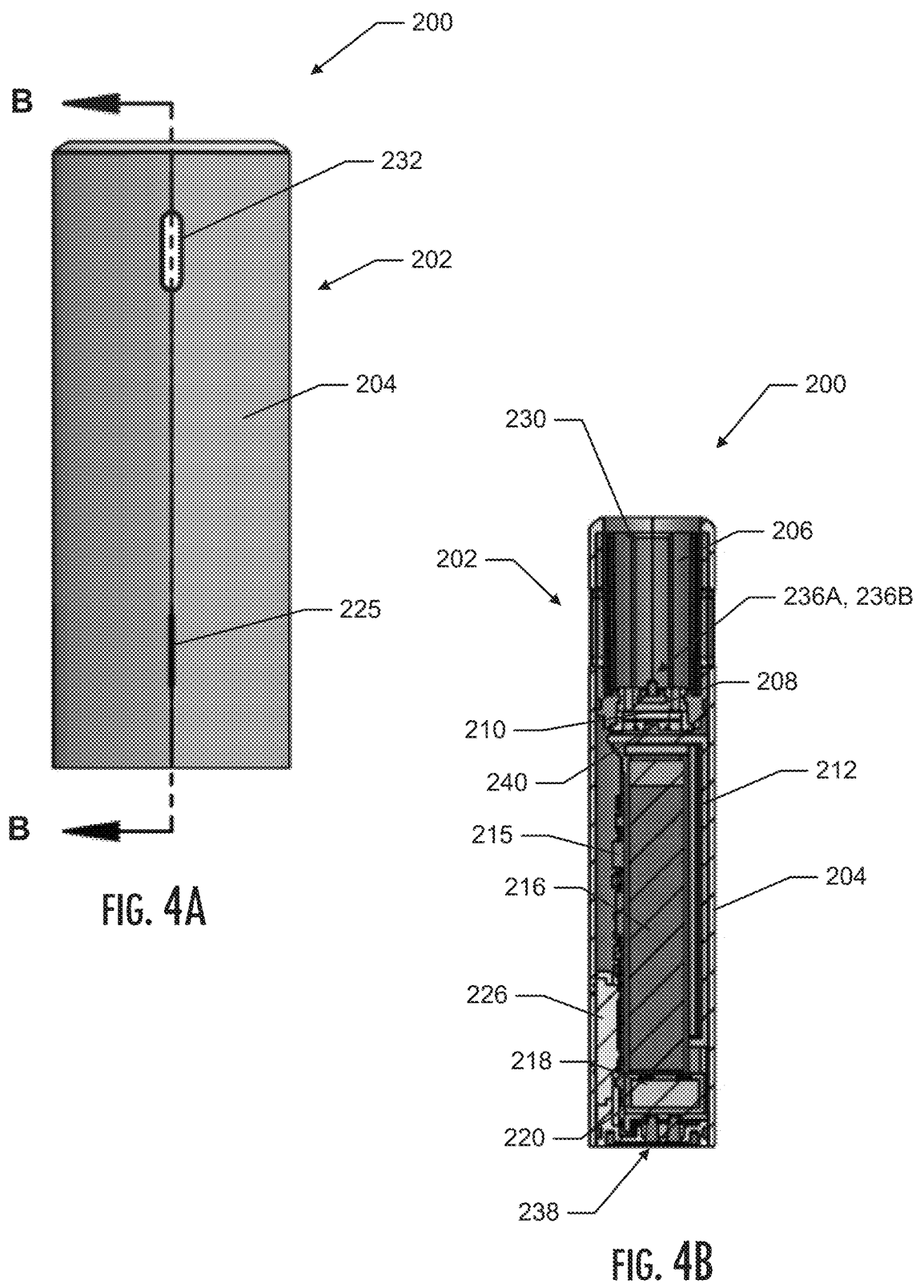
Figures 5A, 5B:
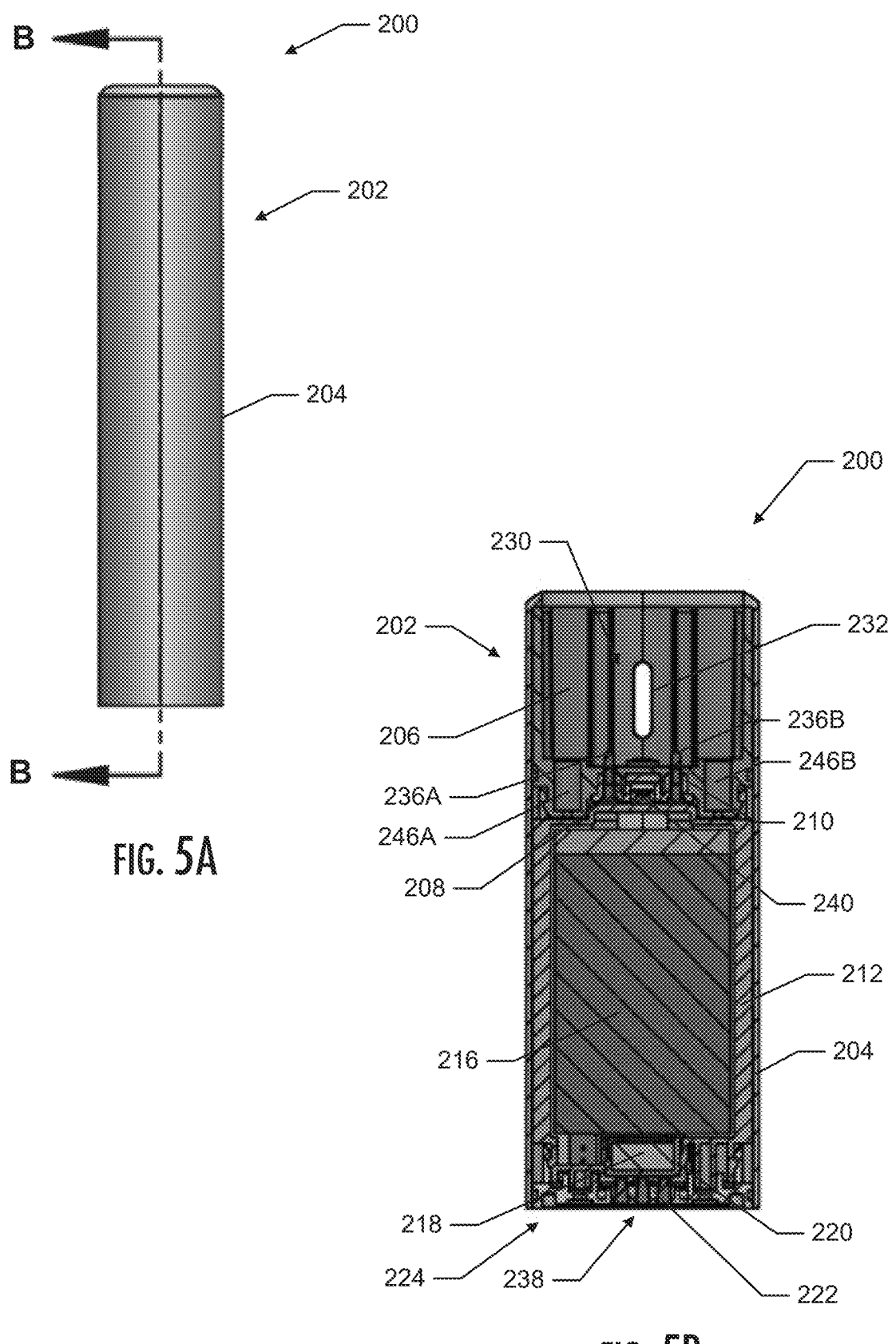
Figure 6:
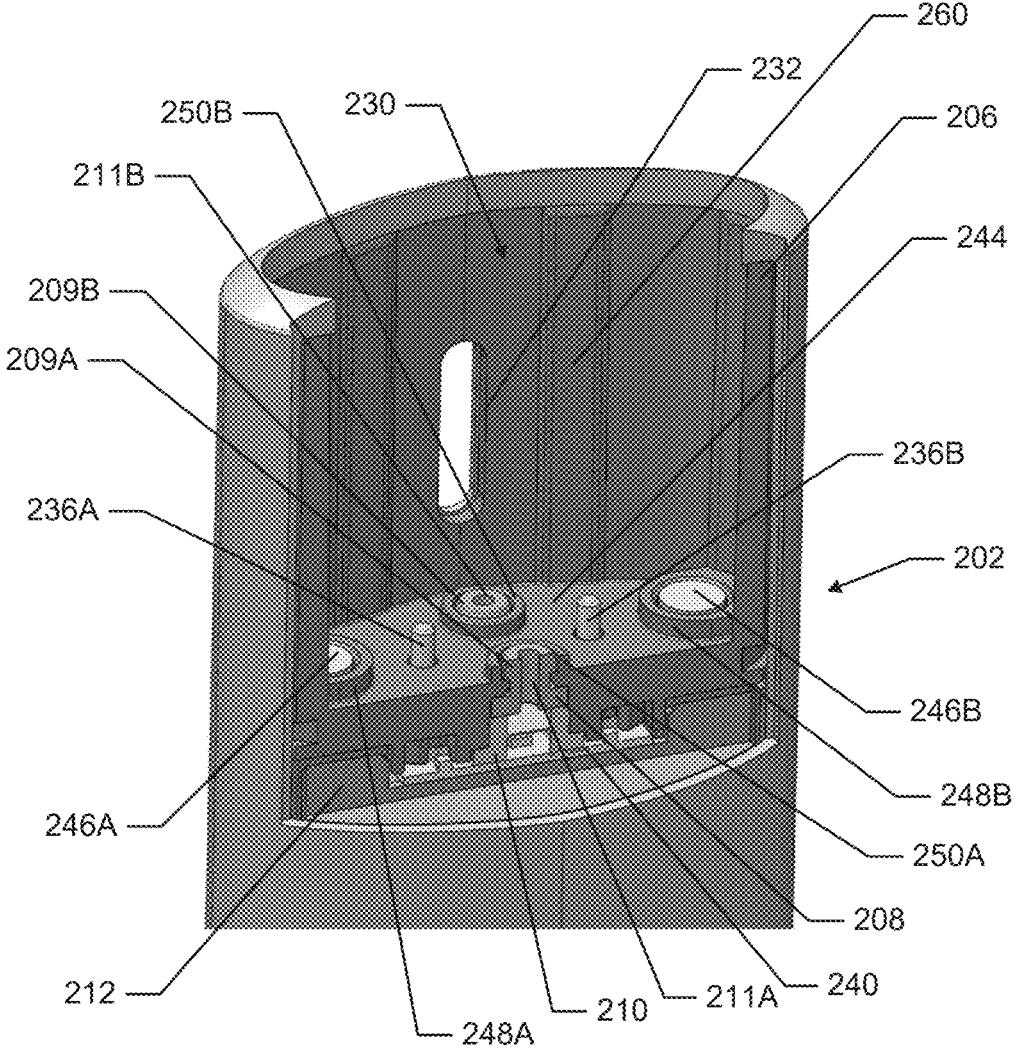
Figure 7:
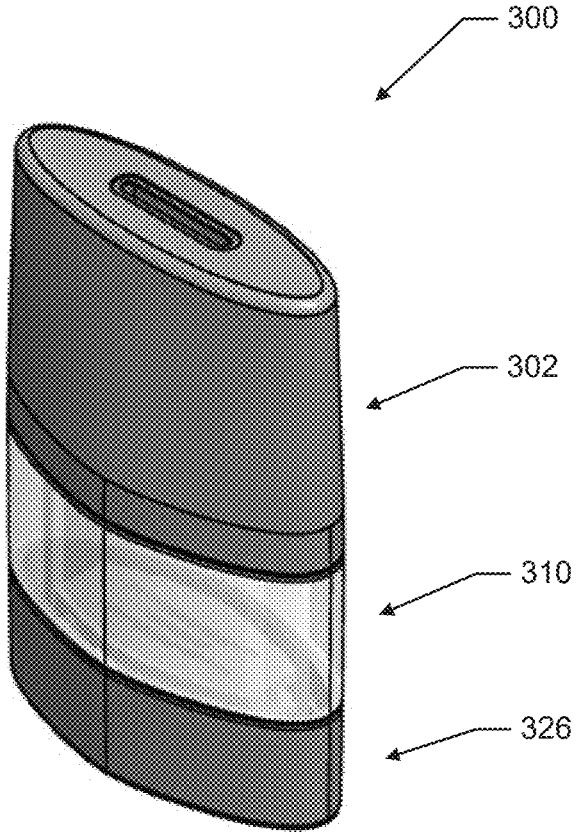
Figure 8:
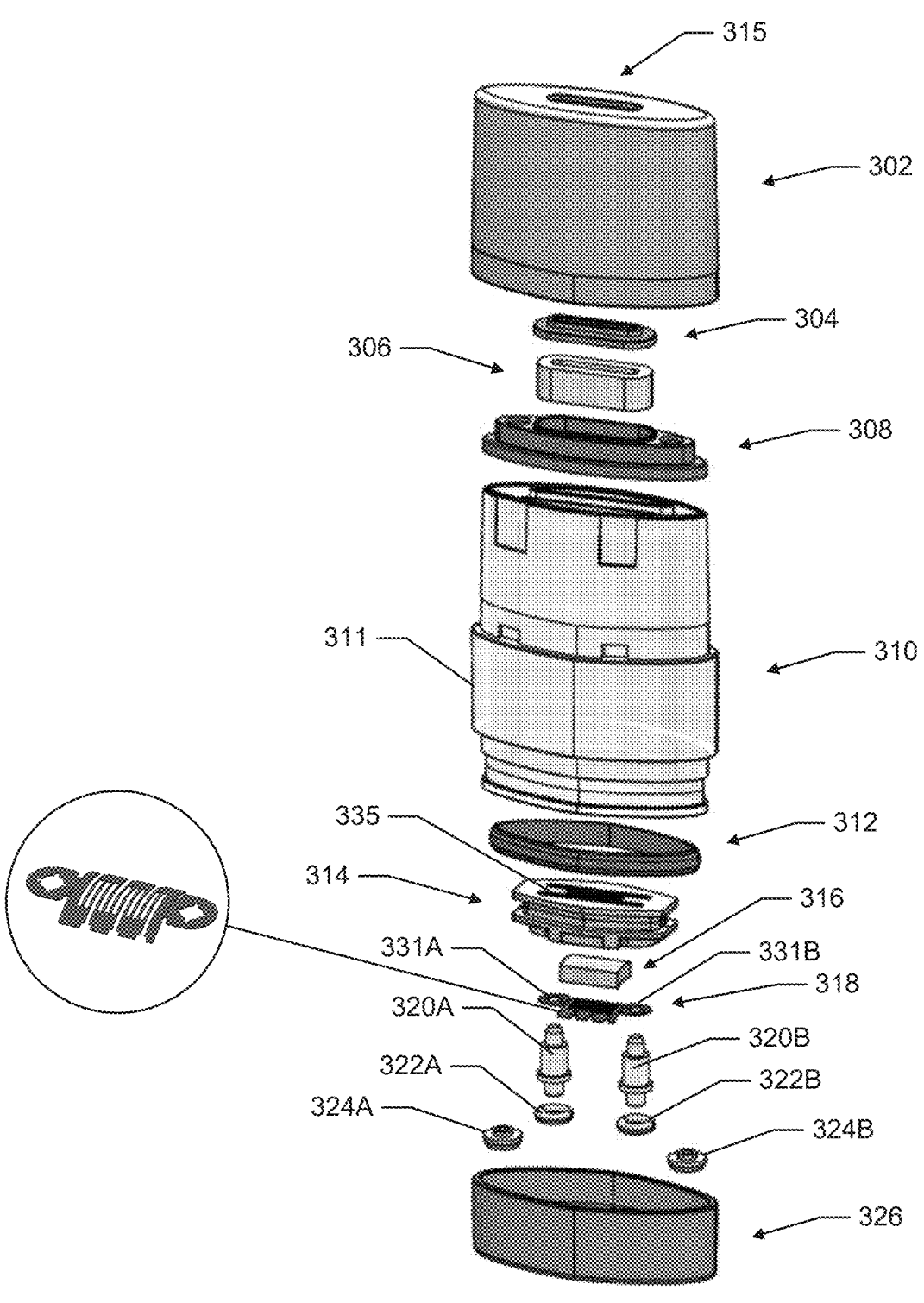
Figures 9A, 9B:
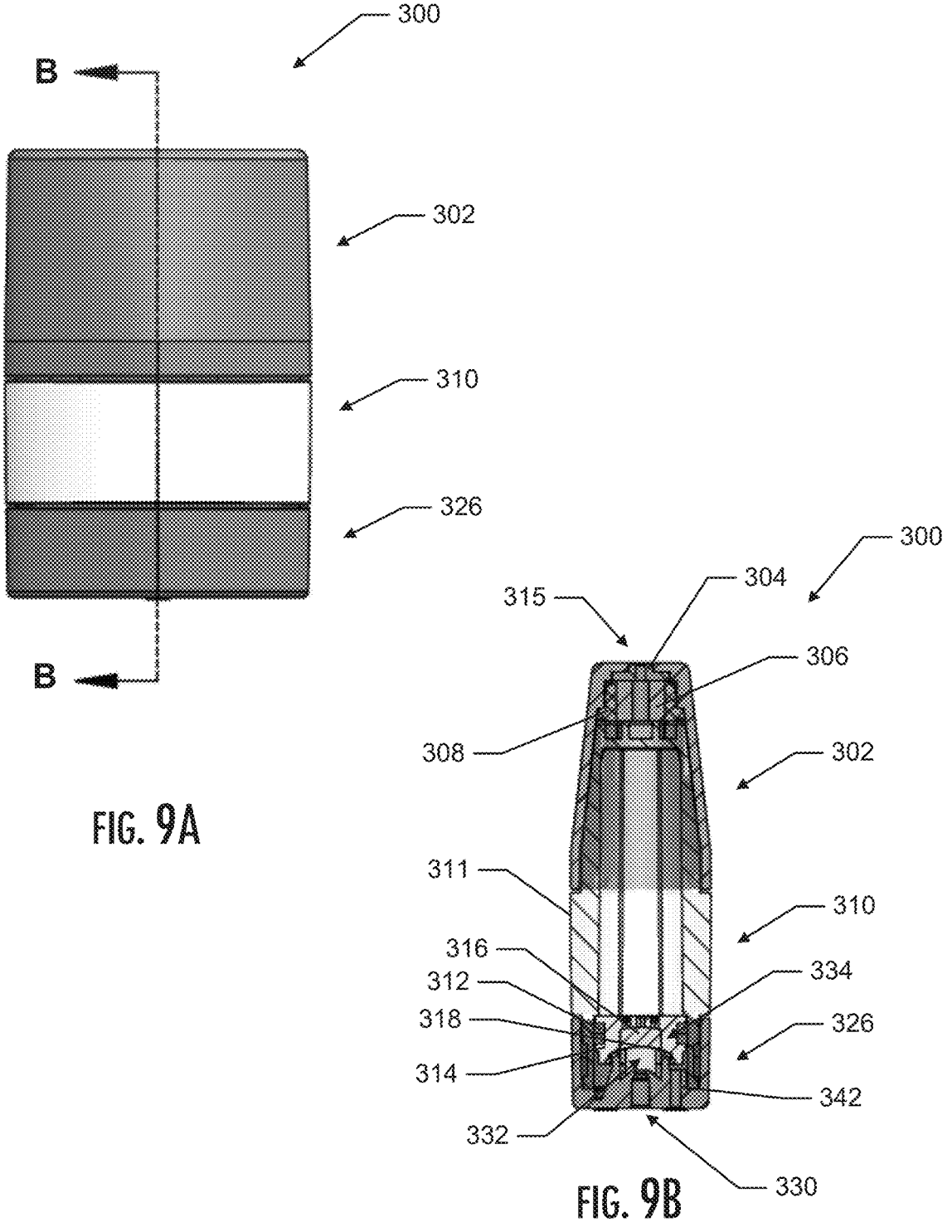
Figures 10A, 10B:
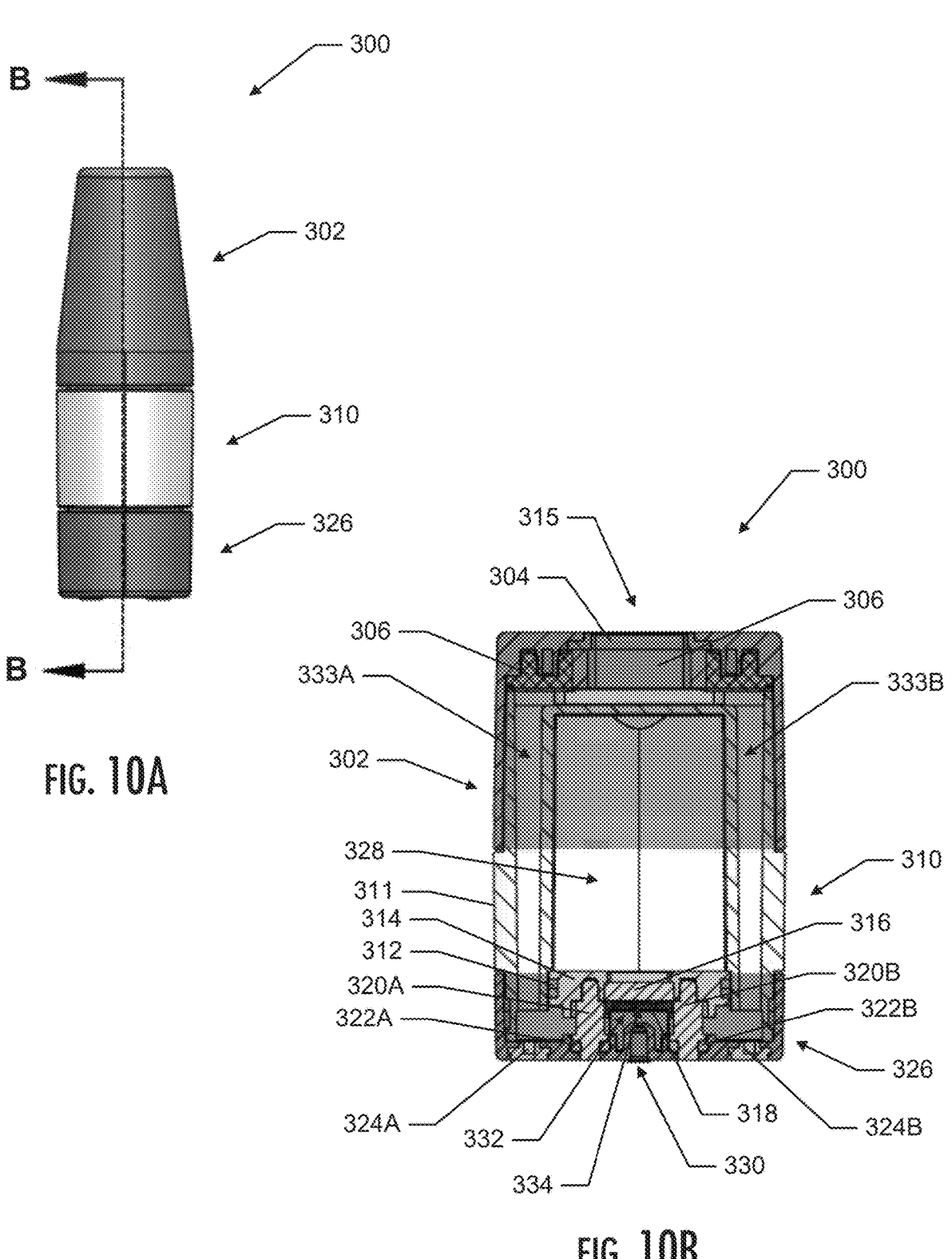
Figure 11:
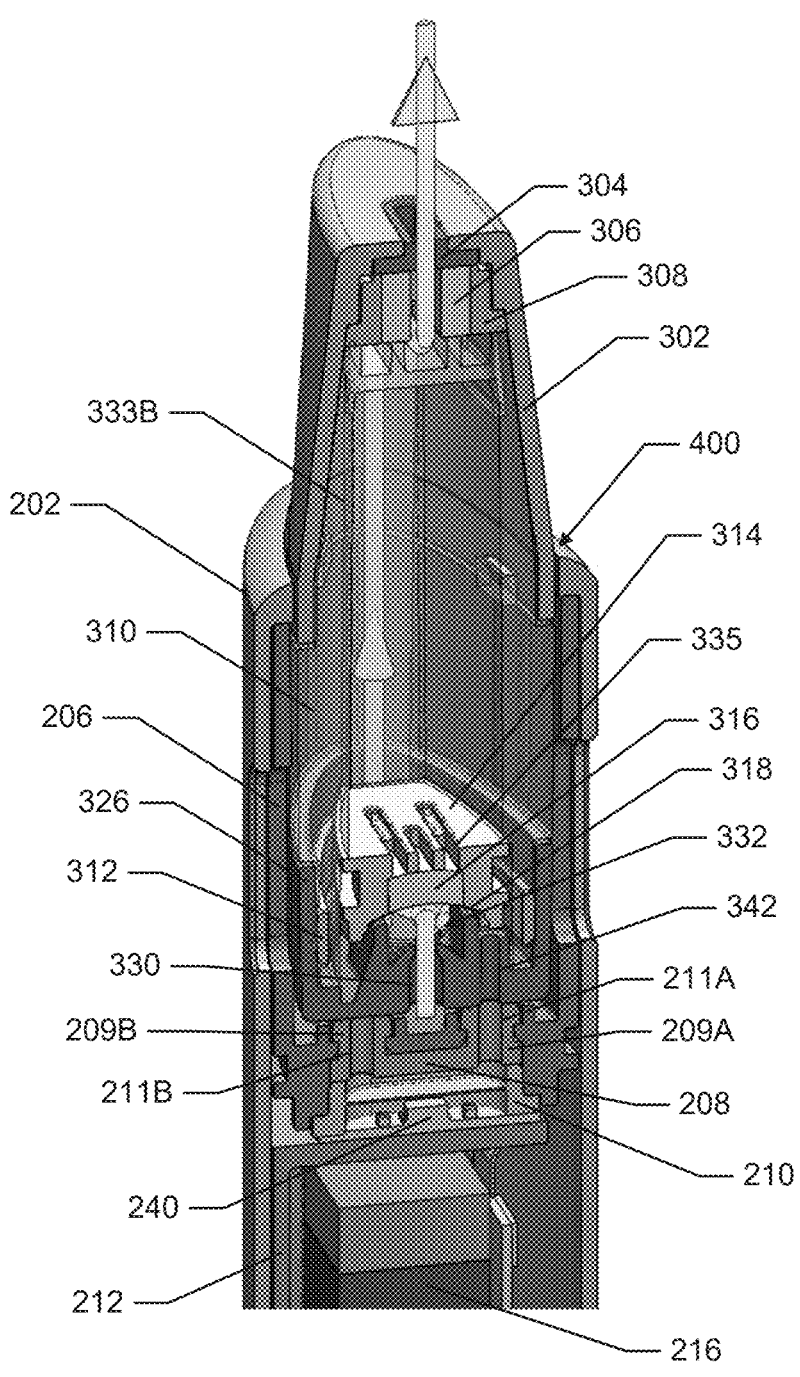
Figures 12A, 12B:
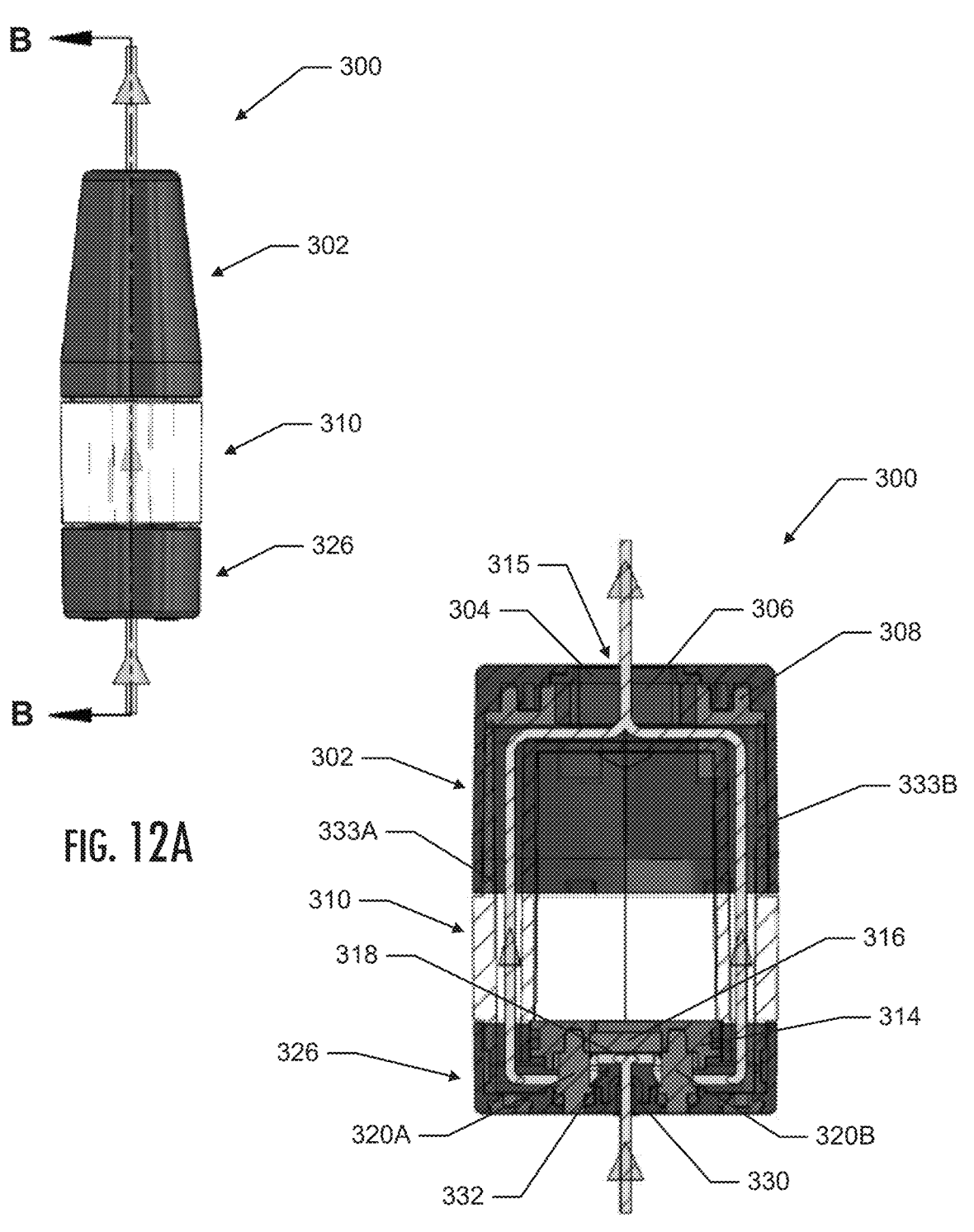
Figure 13:
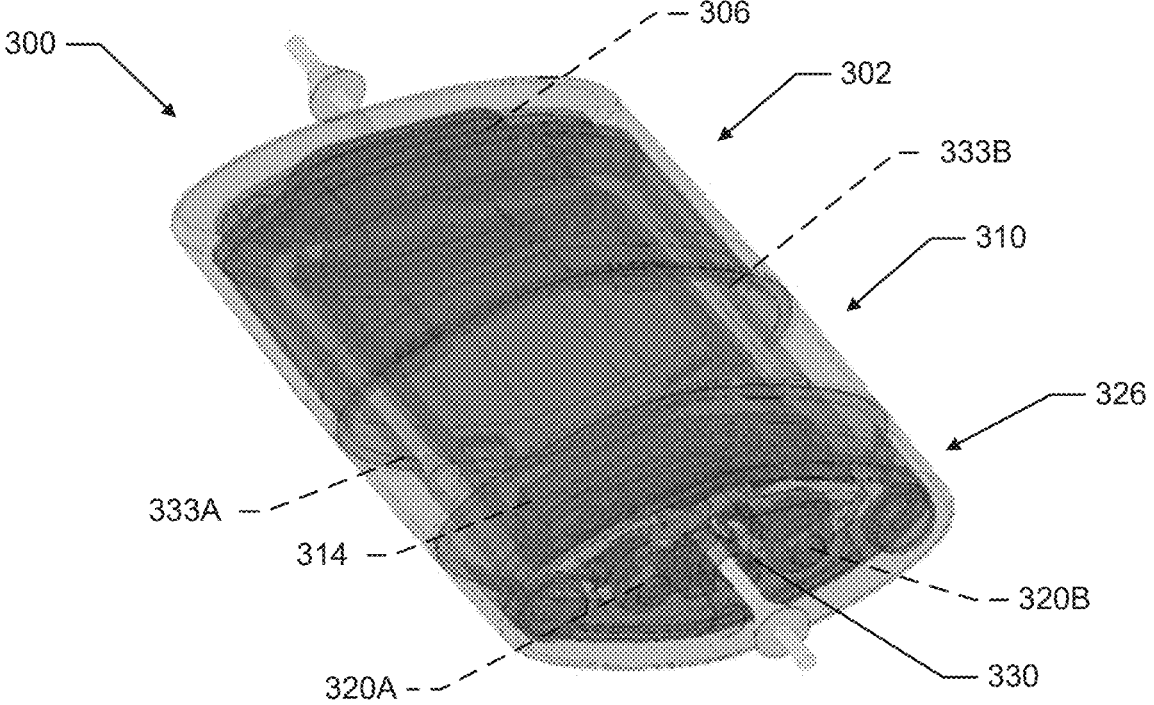
Figure 14:
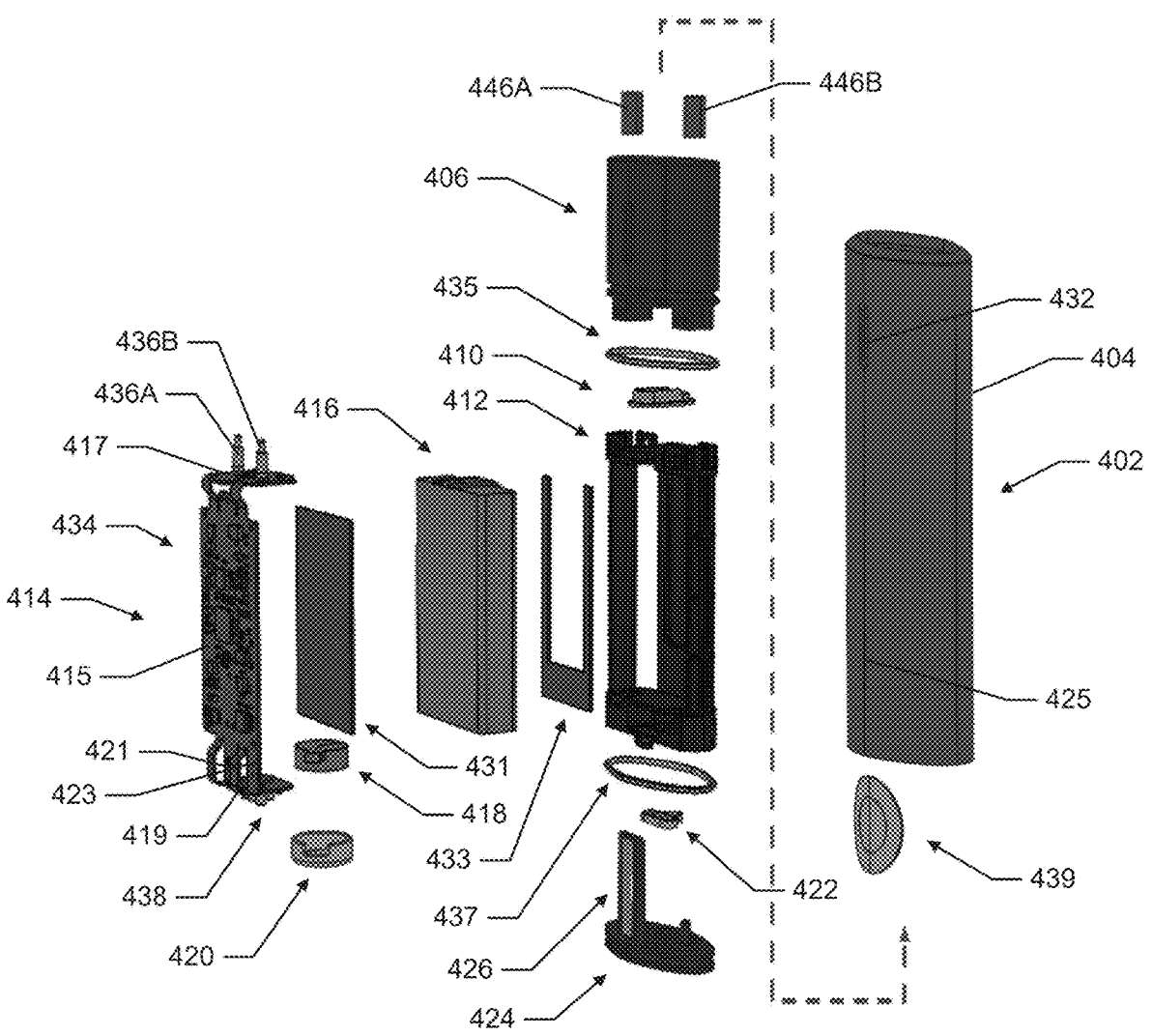
Figure 15:
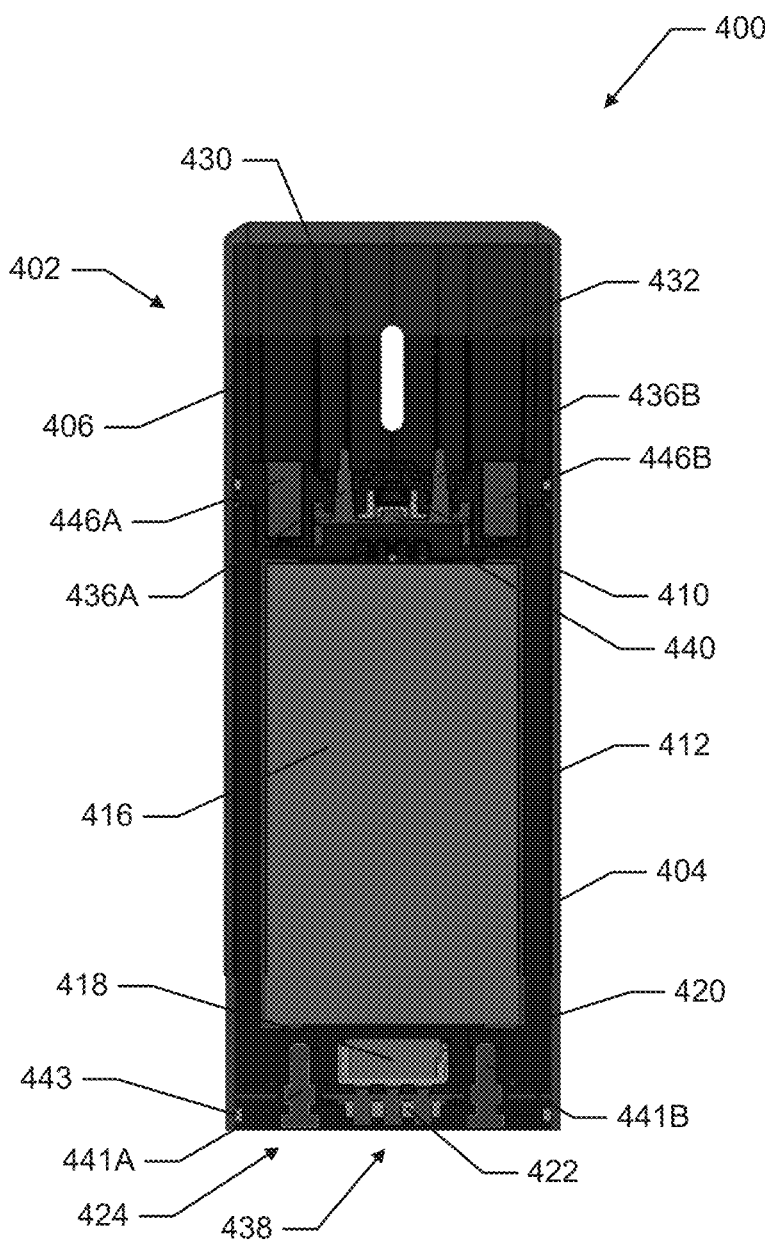
Figure 16:
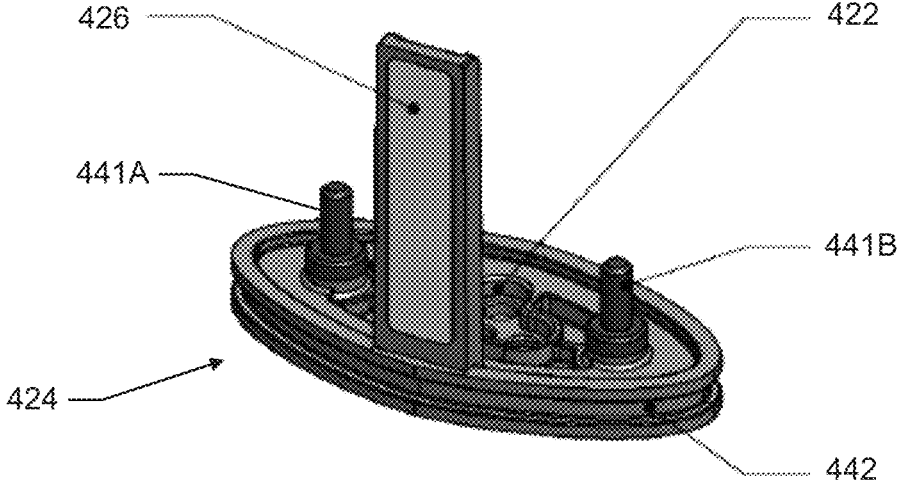
Figures 17A, 17B, 17C:
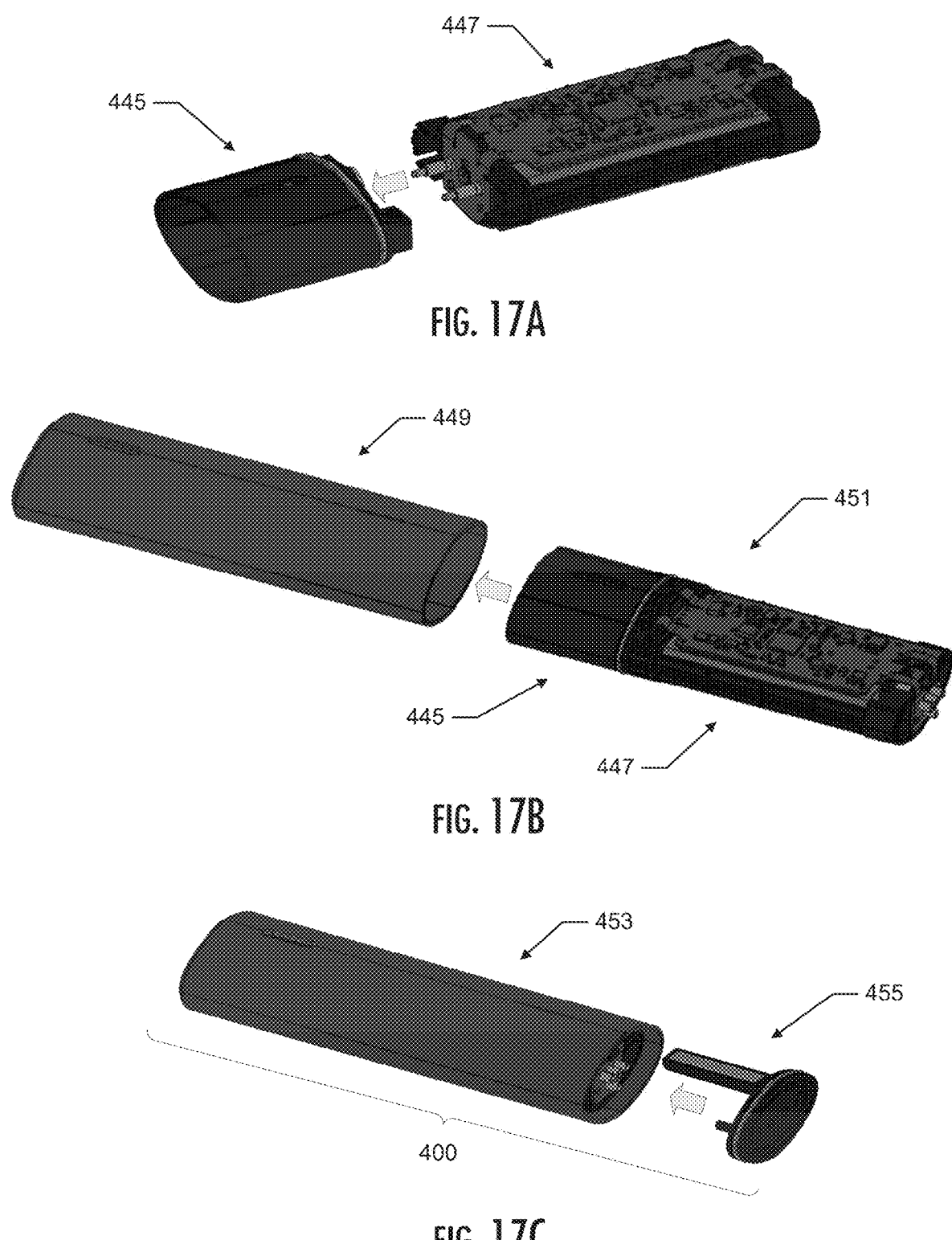
Figure 18:
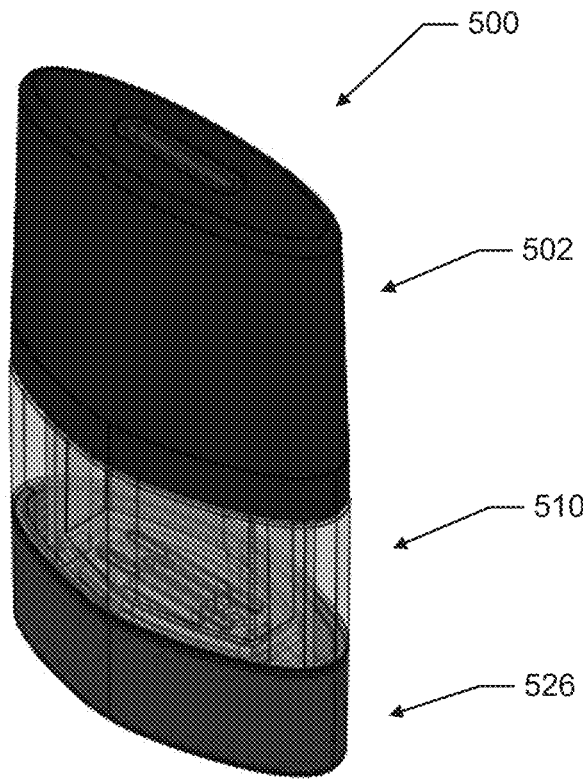
Figure 19:
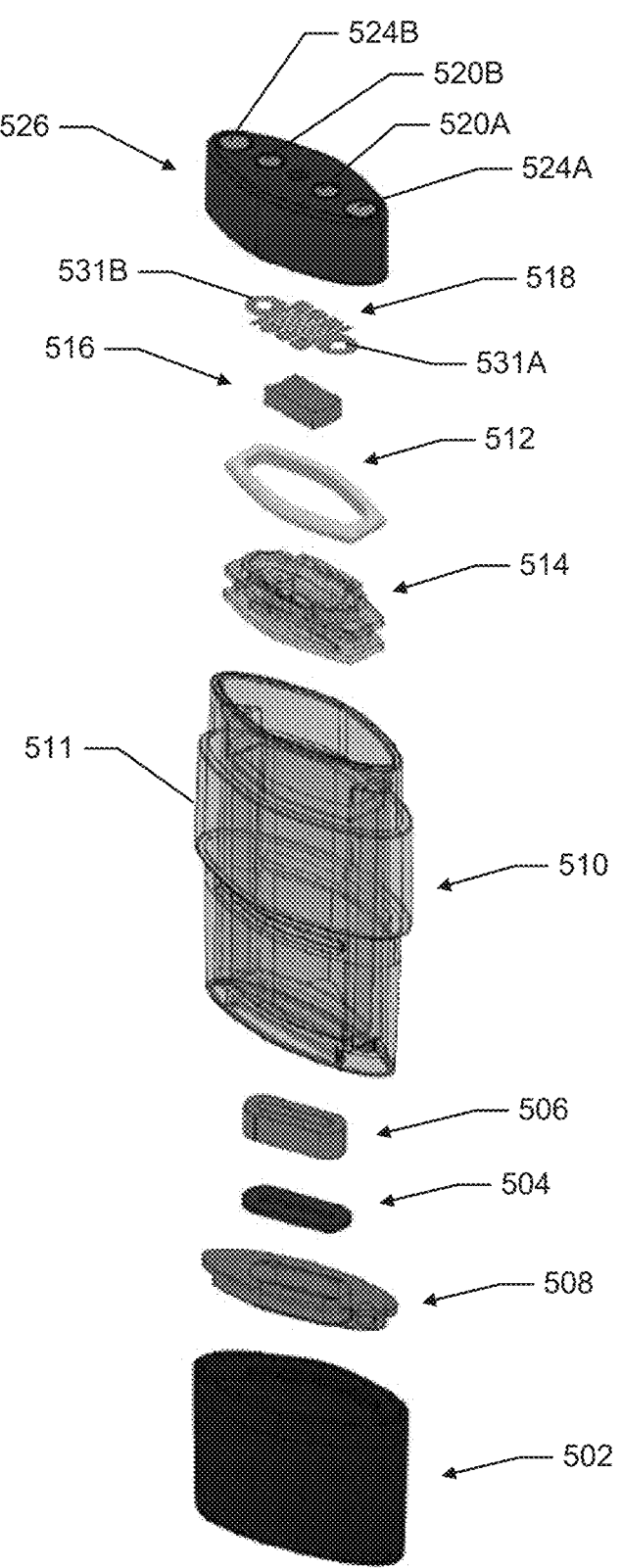
Figure 20:
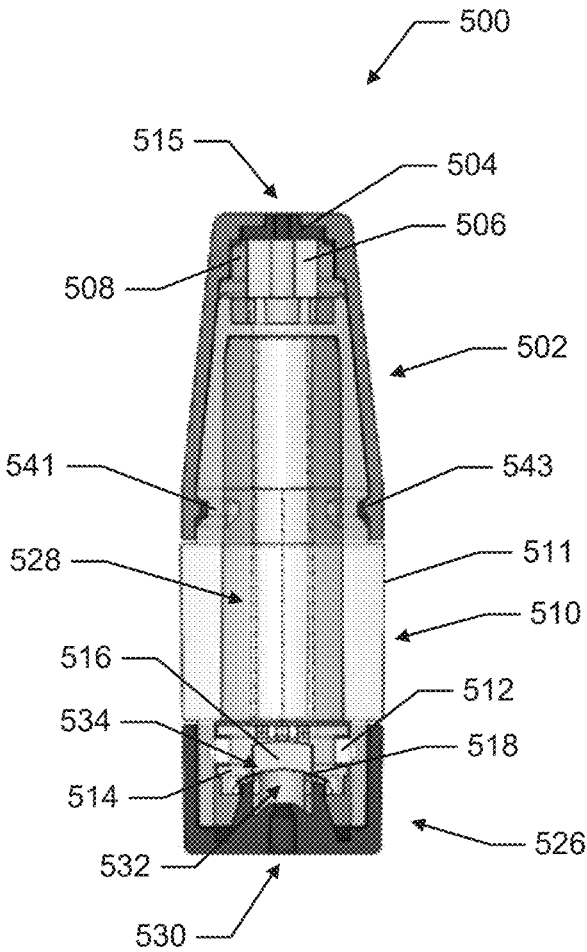
Figures 21A, 21B:
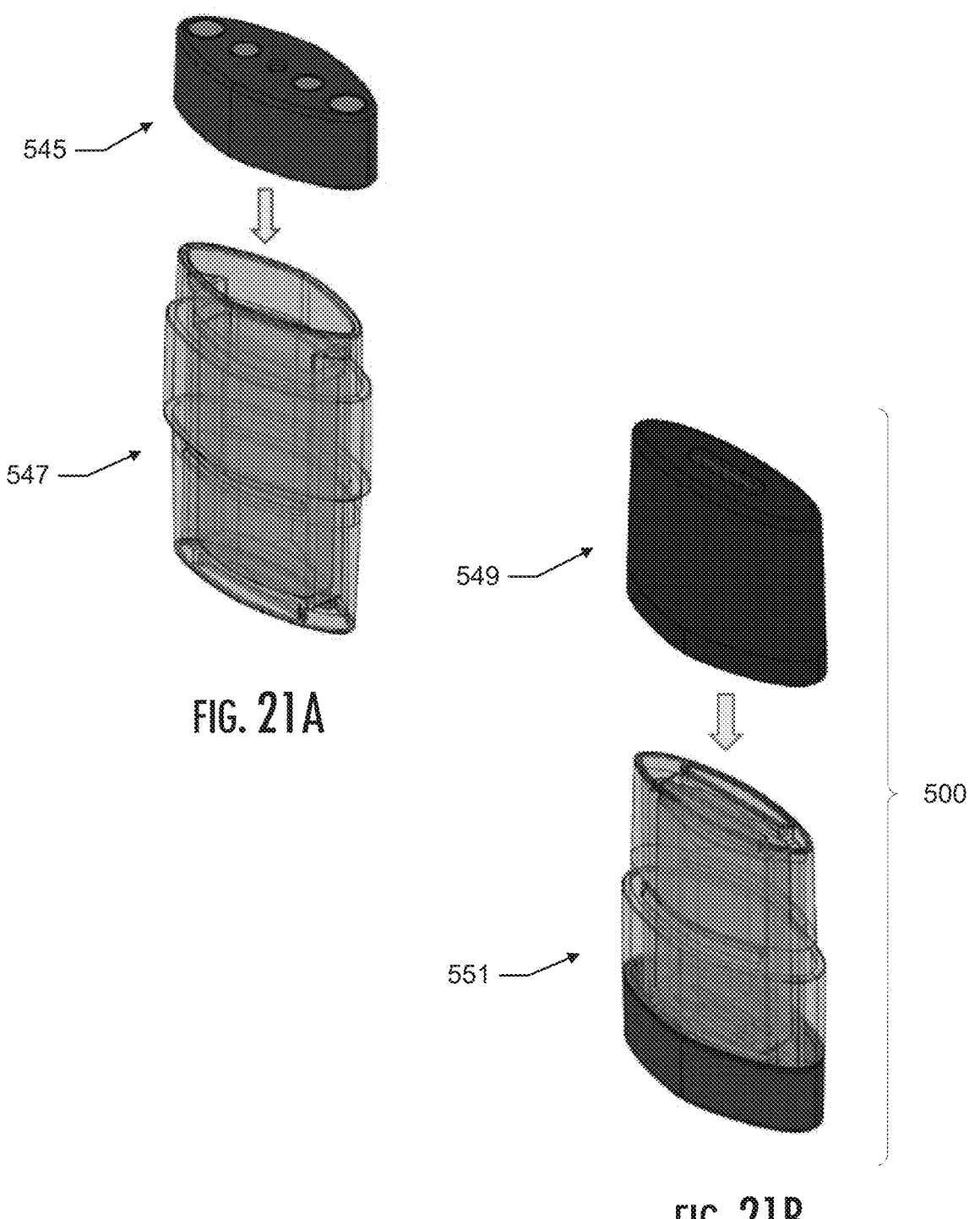
Figure 22:
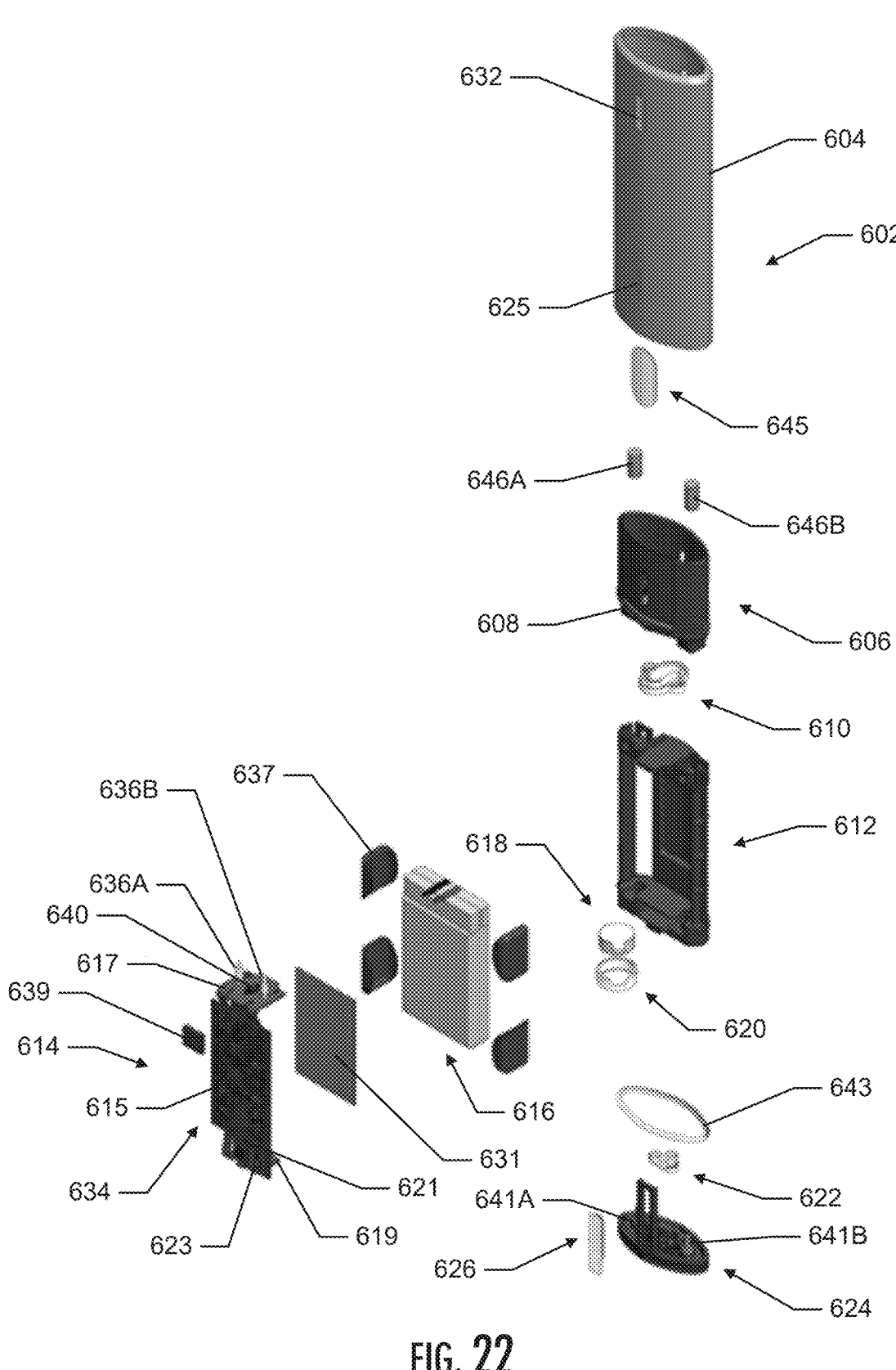
Figure 23:
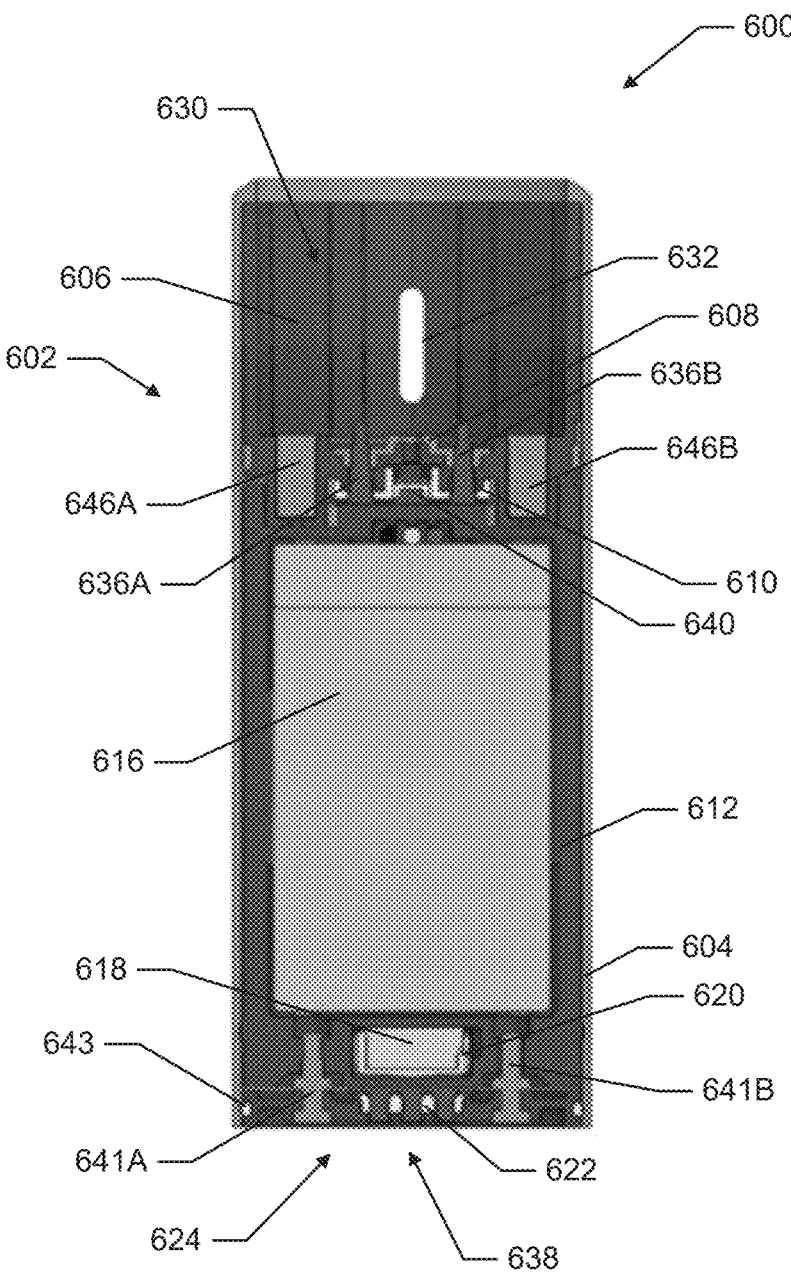
Figure 24:
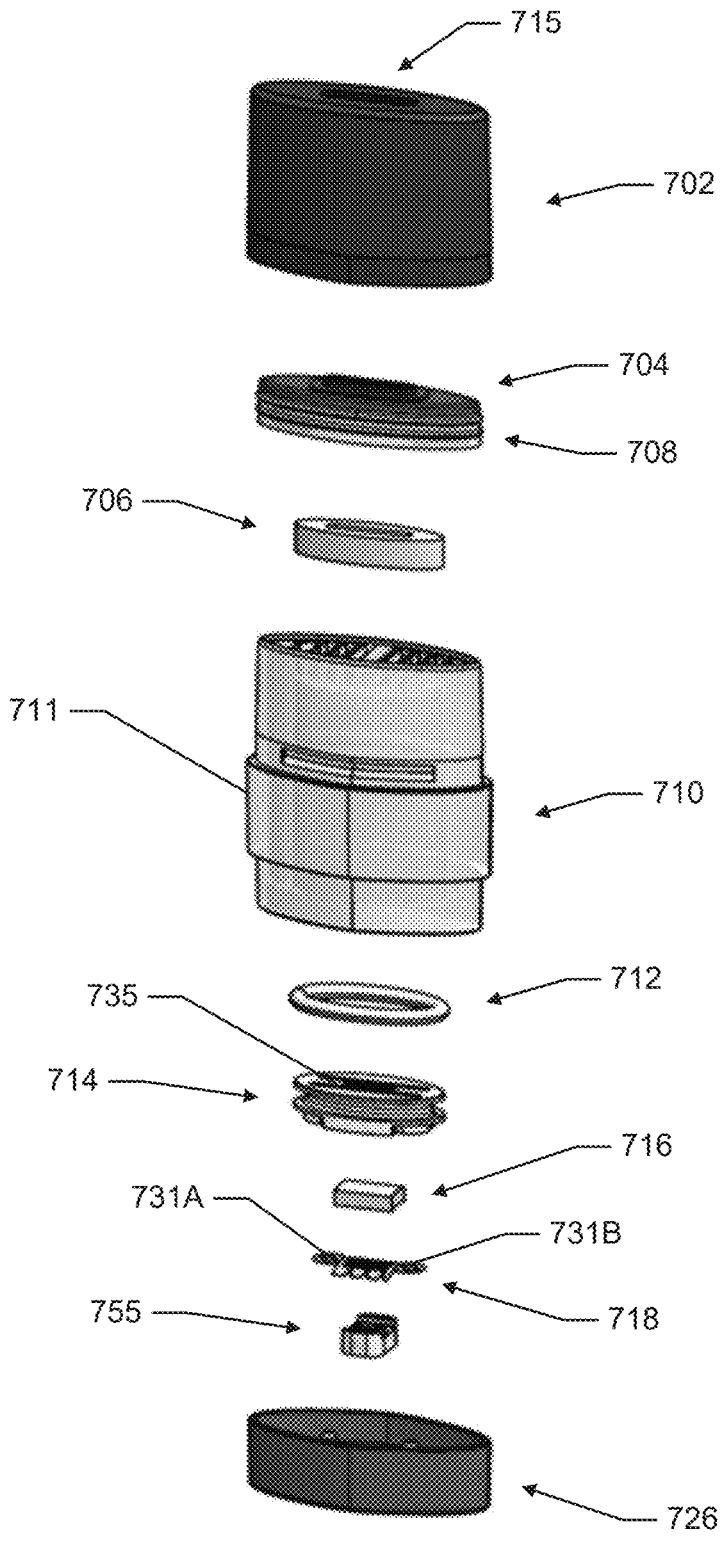
Figure 25:
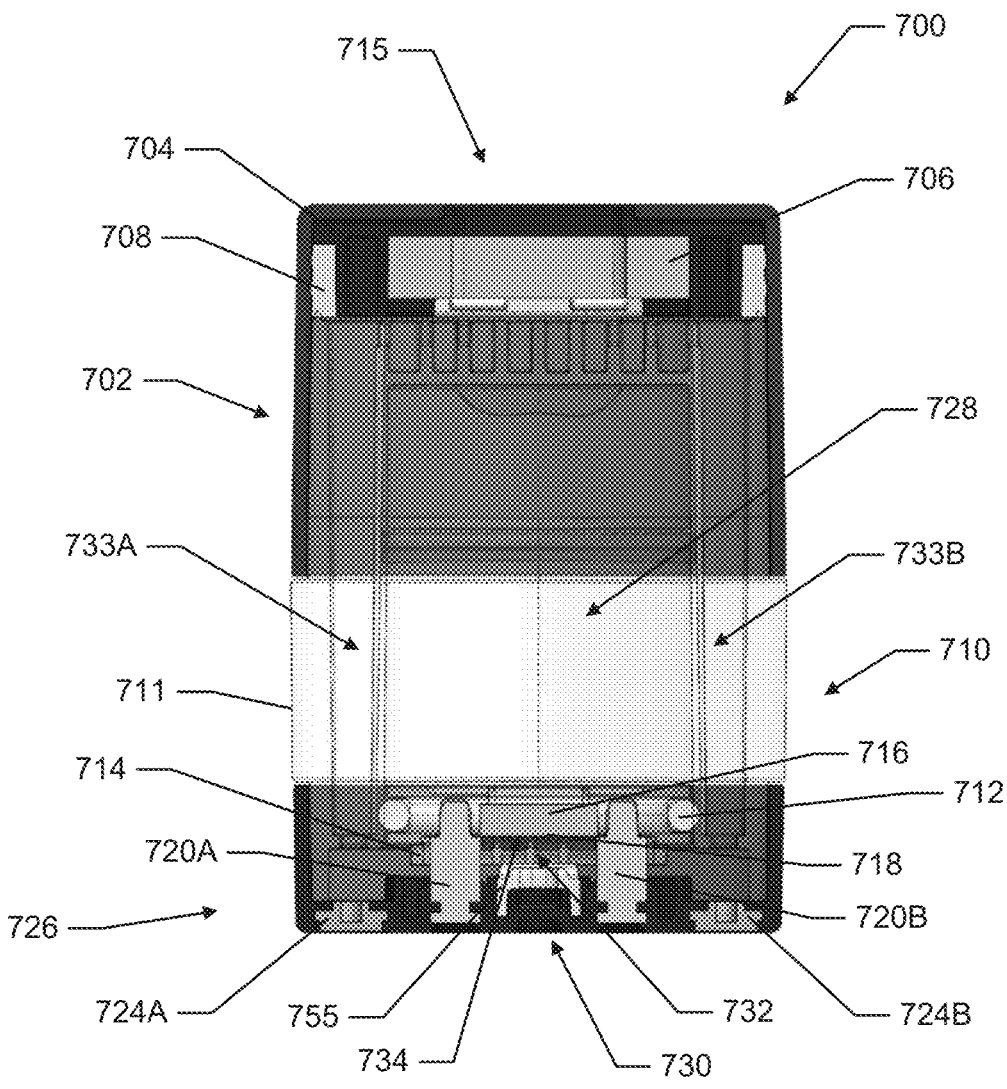
Figure 26:
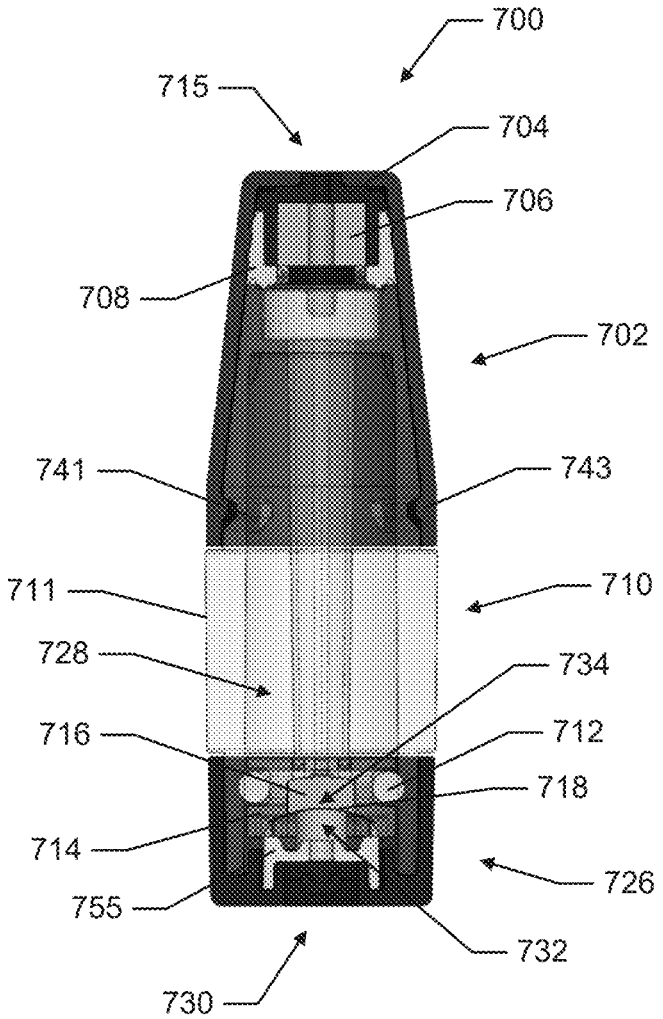
Figure 27:
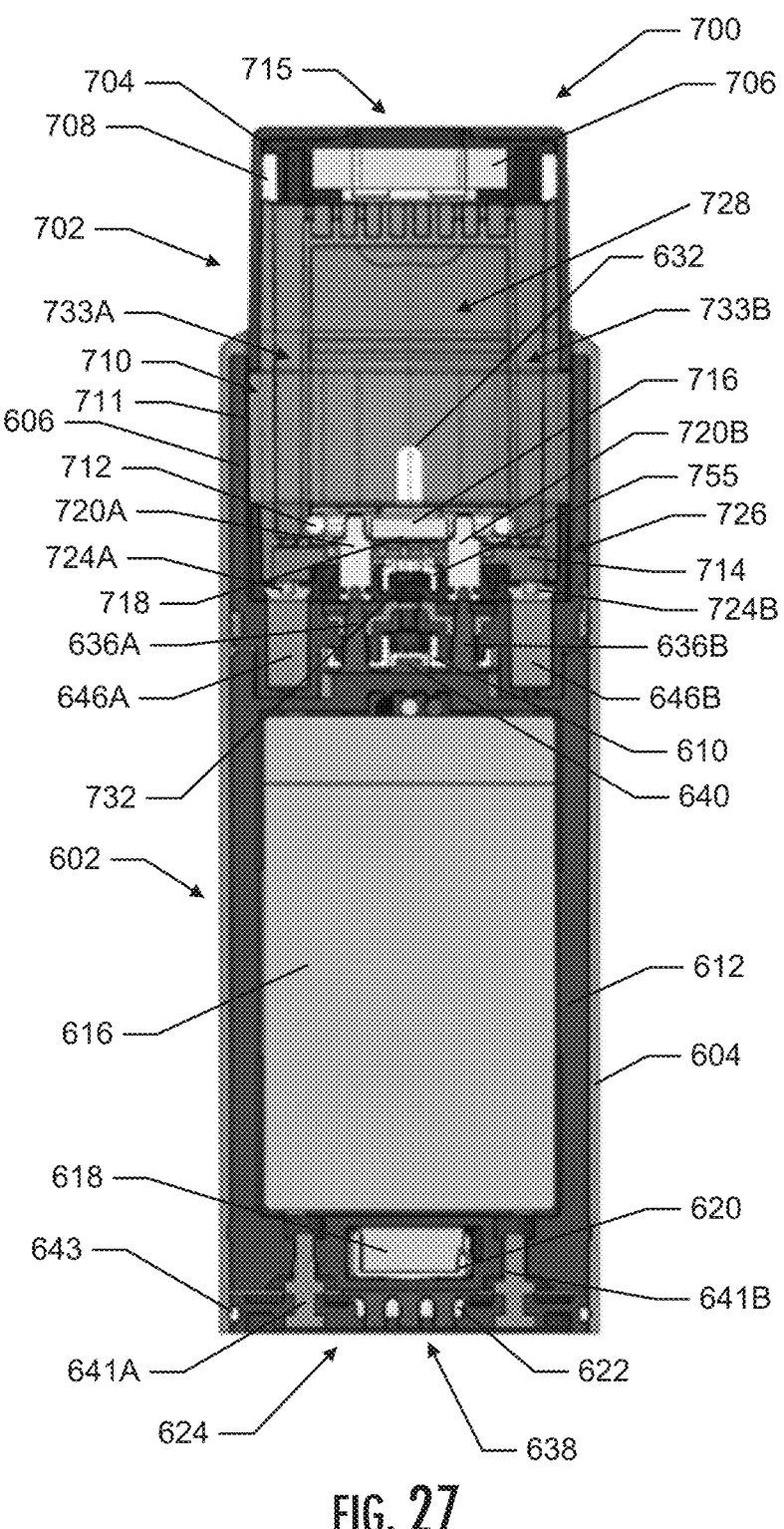
Figure 28:
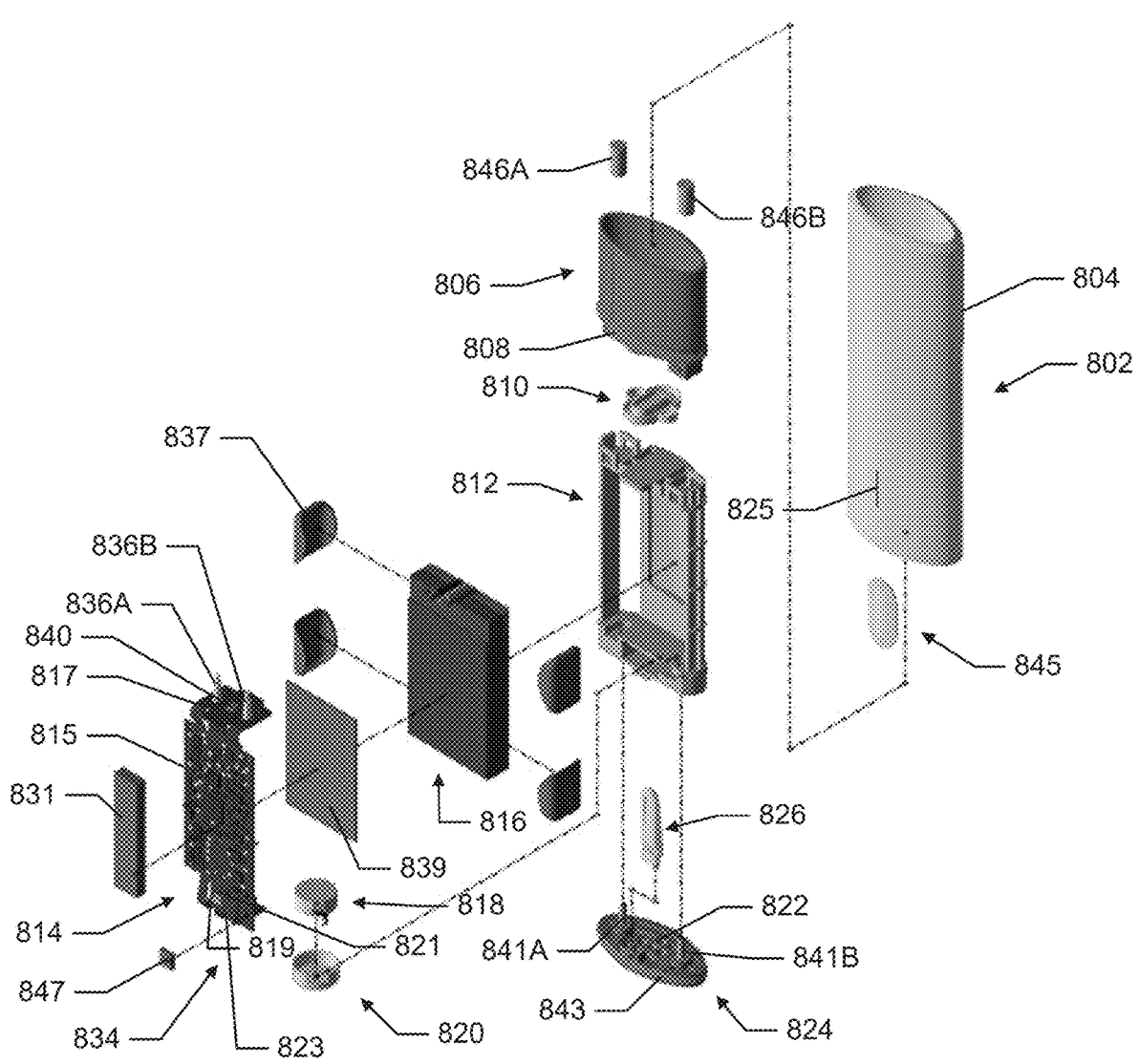
Figure 29:
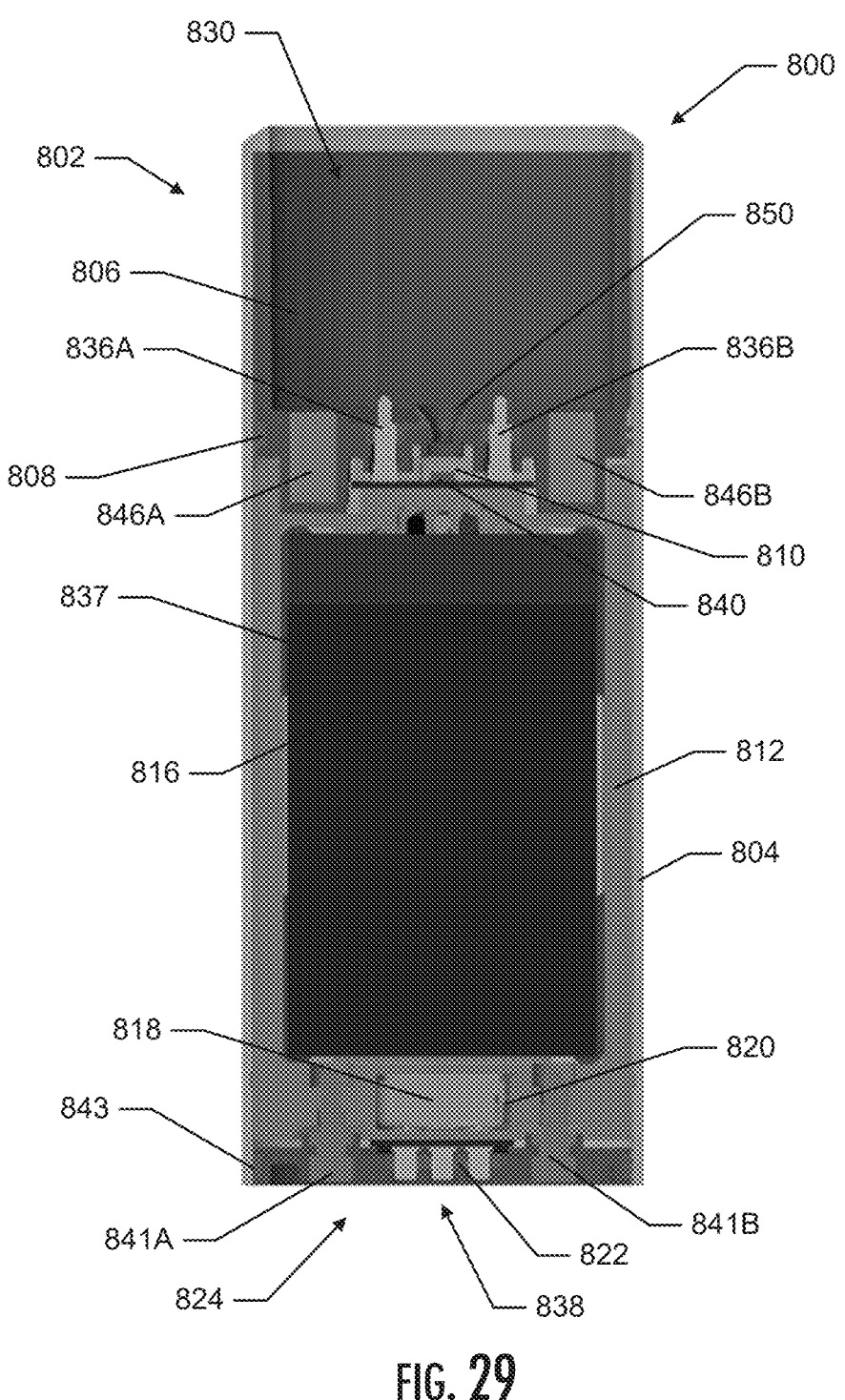
Figure 30:
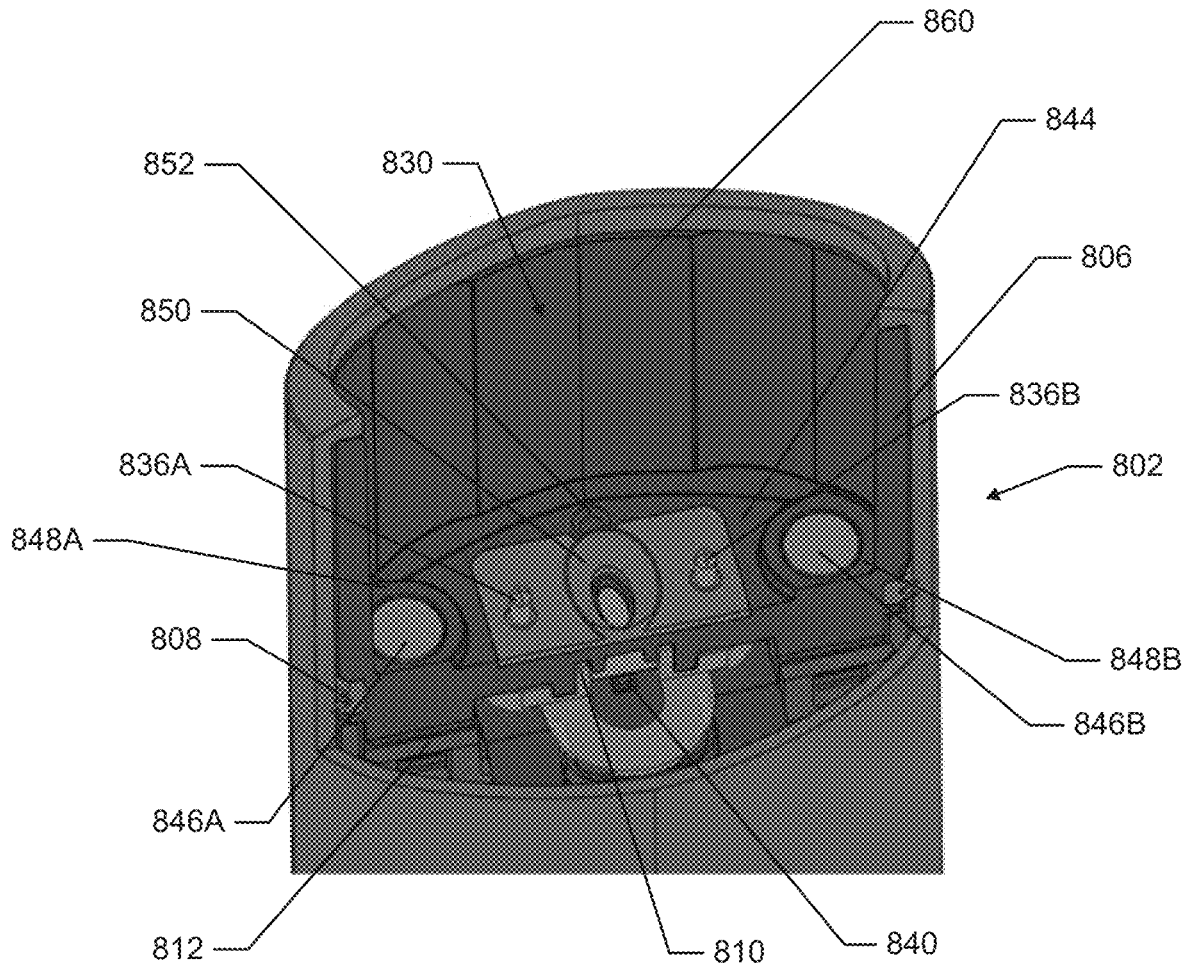
Figure 31:
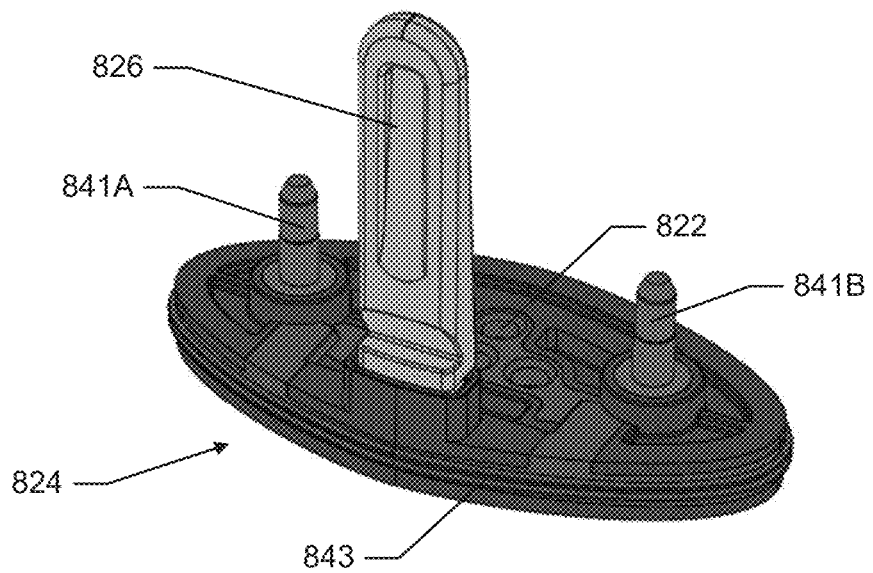
Figure 32:
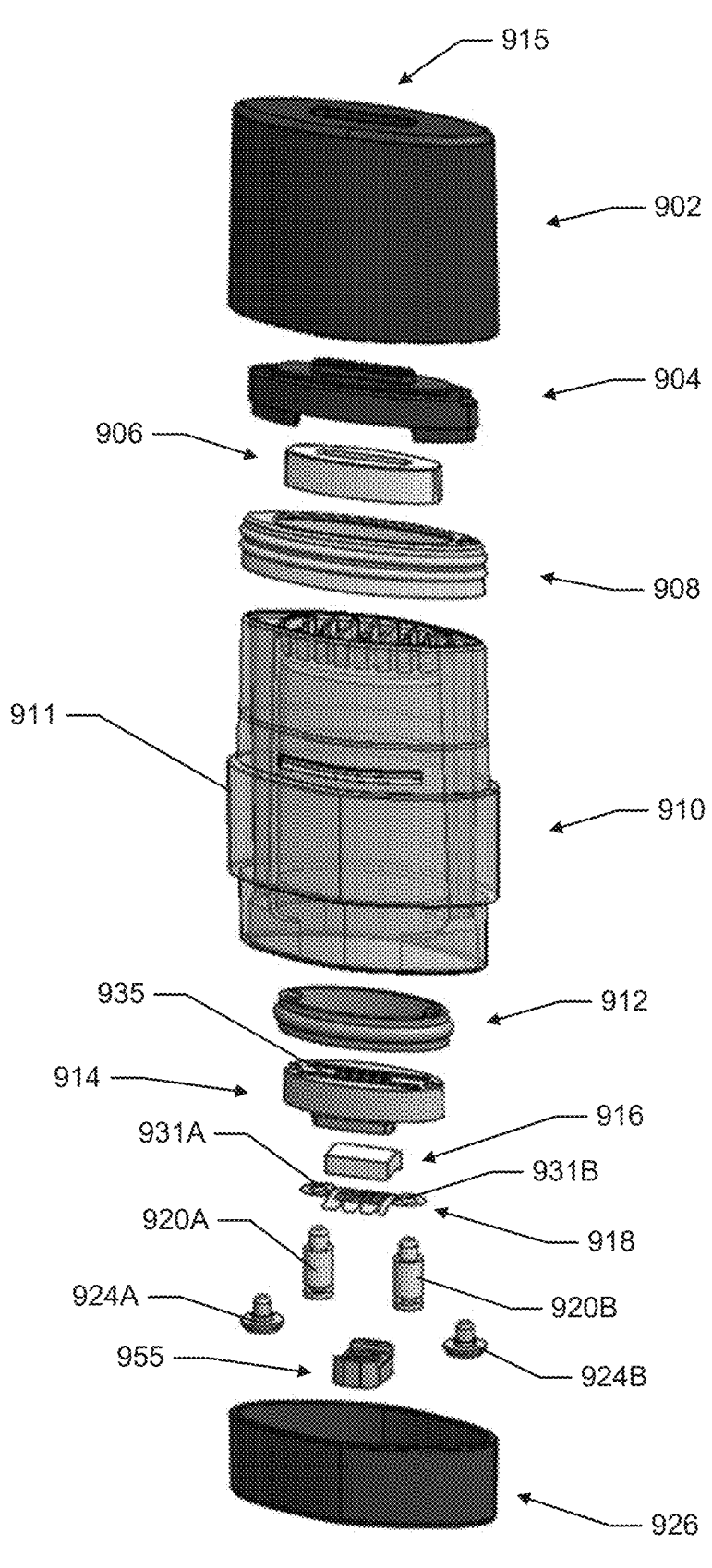
Figure 33:
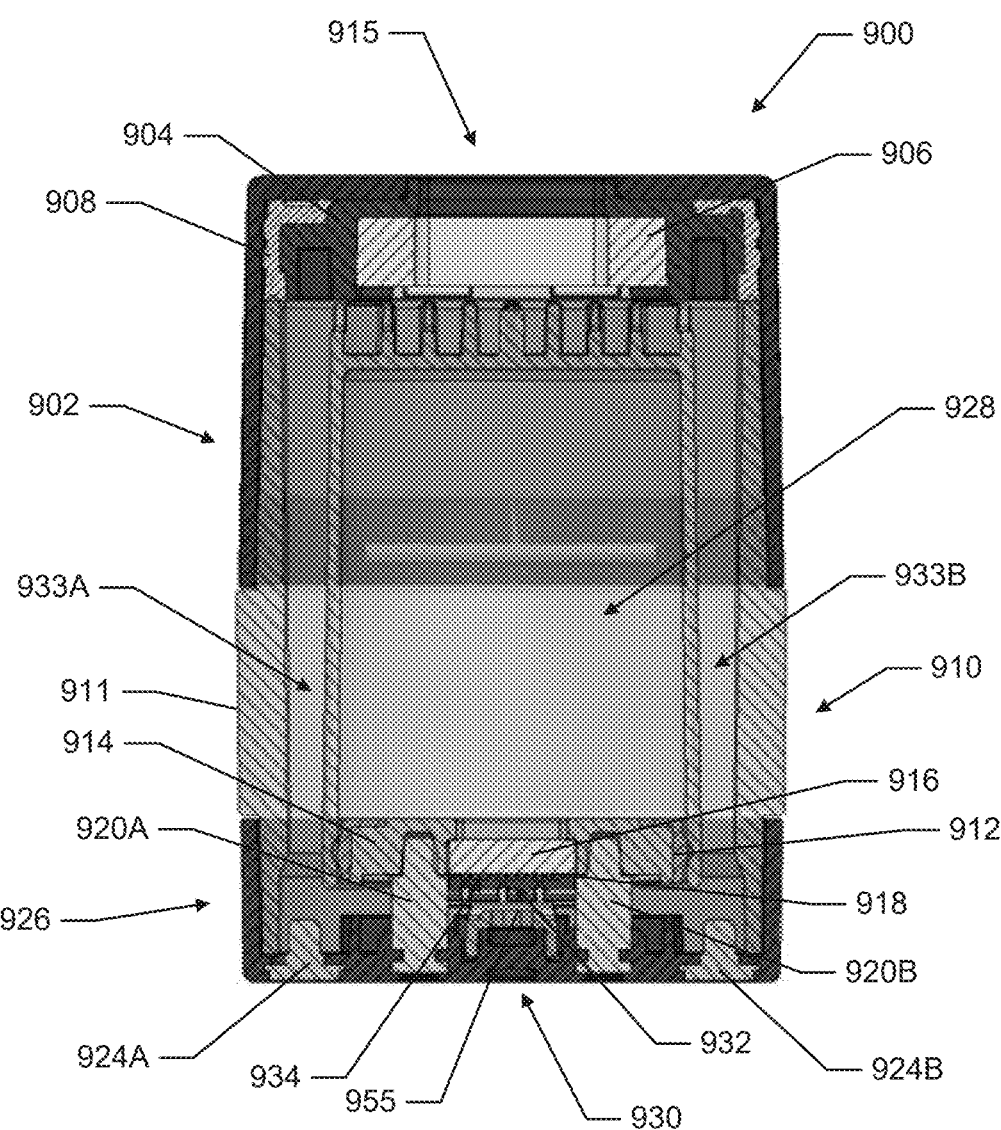
Figure 34:
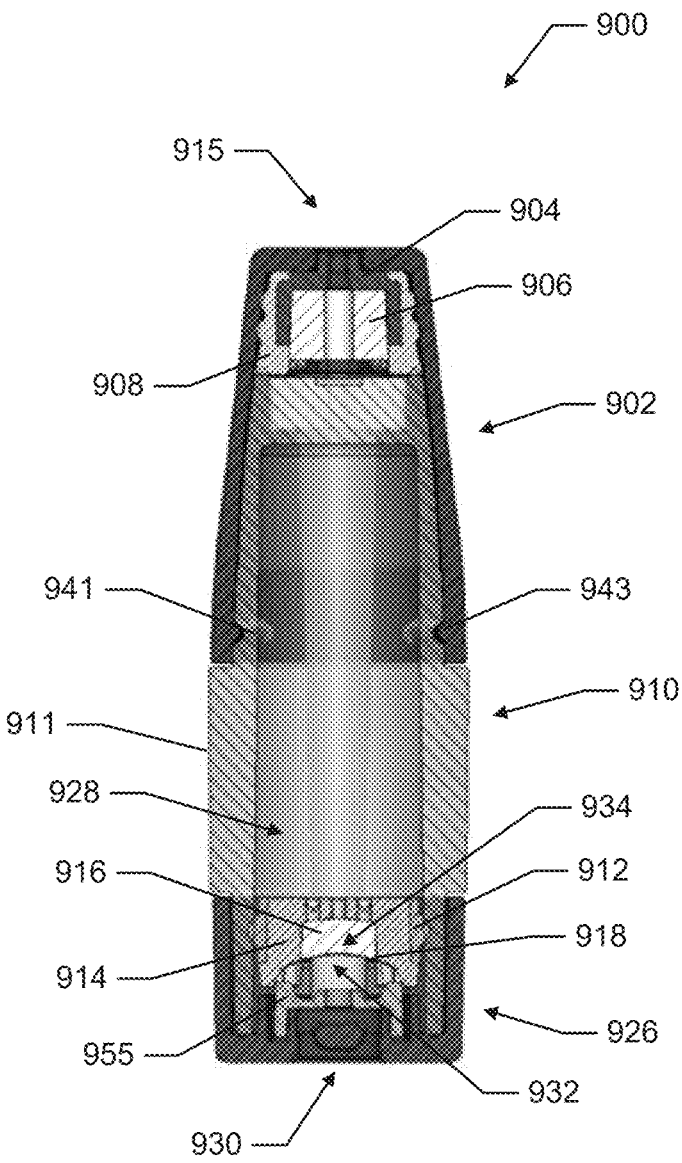
Figure 35:
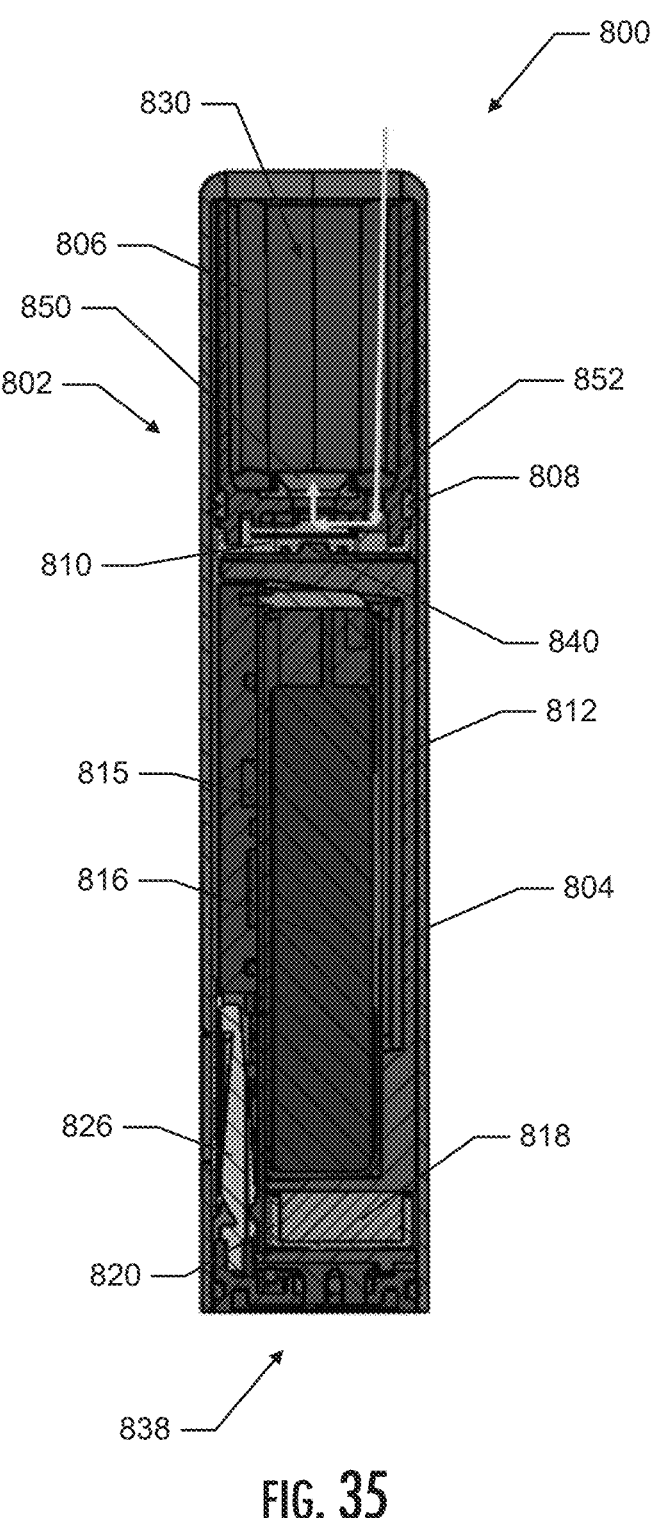
Figure 36:
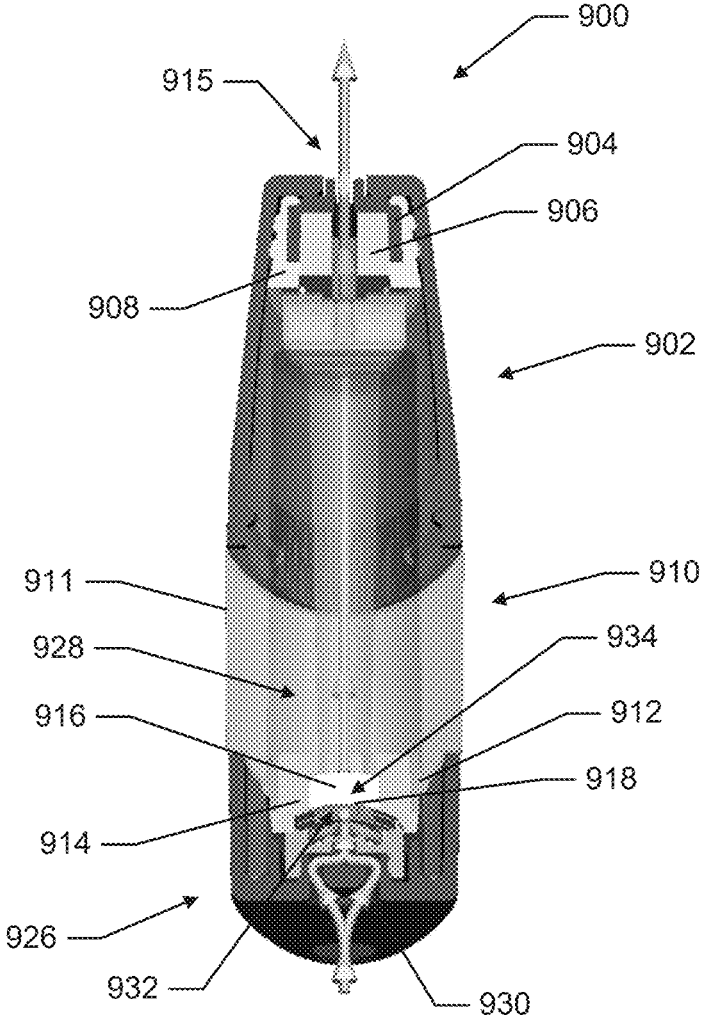
Figure 37:
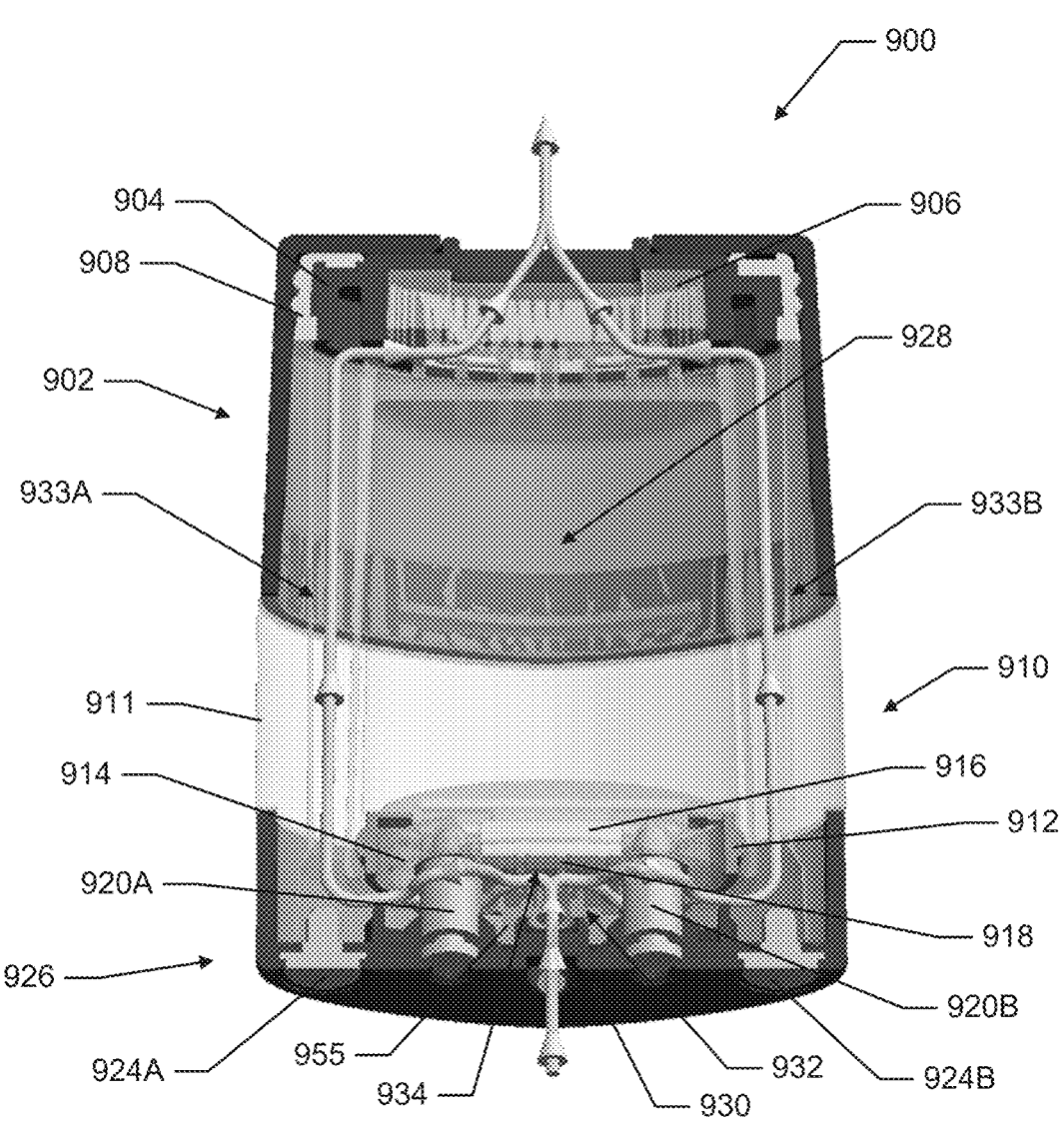
Figure 38:
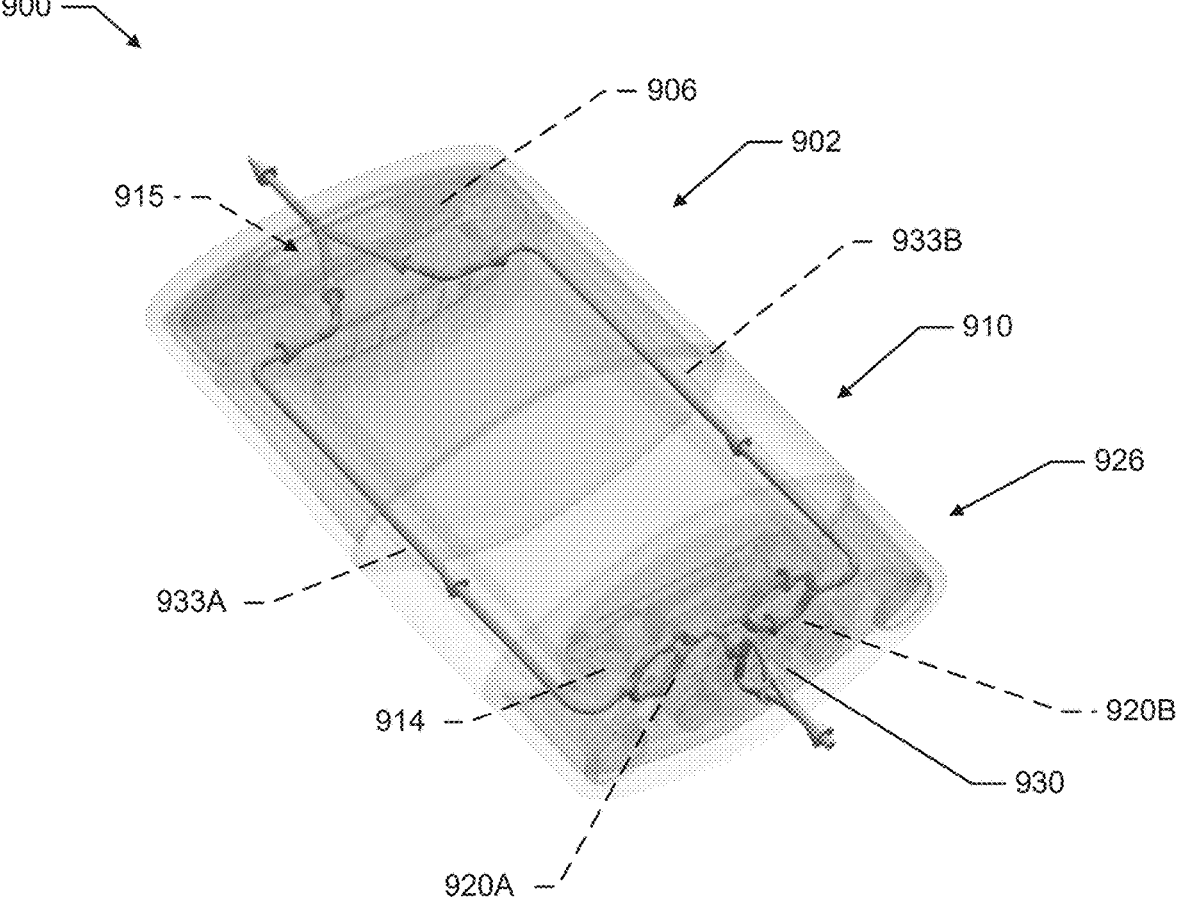

Having thus described the disclosure in the foregoing general terms, reference will now be made to the accompanying drawings, which are not necessarily drawn to scale, and wherein:

FIG. 1 illustrates a perspective view of an aerosol delivery device, according to example implementations of the present disclosure;

FIG. 2 illustrates a perspective view of a control device of an aerosol delivery device, according to example implementations of the present disclosure;

FIG. 3 illustrates an exploded perspective view of a control device of an aerosol delivery device, according to an example implementation of the present disclosure;

FIG. 4A illustrates a front view of a control device of an aerosol delivery device, according to an example implementation of the present disclosure;

FIG. 4B illustrates a corresponding section view of the control device of FIG. 4A, according to an example implementation of the present disclosure;

FIG. 5A illustrates a side view of a control device of an aerosol delivery device, according to an example implementation of the present disclosure;

FIG. 5B illustrates a corresponding section view of the control device of FIG. 5A, according to an example implementation of the present disclosure;

FIG. 6 illustrates a perspective partial section view of a control device of an aerosol delivery device, according to an example implementation of the present disclosure;

FIG. 7 illustrates a perspective view of a cartridge of an aerosol delivery device, according to example implementations of the present disclosure;

FIG. 8 illustrates an exploded perspective view of a cartridge of an aerosol delivery device, according to an example implementation of the present disclosure;

FIG. 9A illustrates a front view of a cartridge of an aerosol delivery device, according to an example implementation of the present disclosure;

FIG. 9B illustrates a corresponding section view of the cartridge of FIG. 8A, according to an example implementation of the present disclosure;

FIG. 10A illustrates a side view of a cartridge of an aerosol delivery device, according to an example implementation of the present disclosure;

FIG. 10B illustrates a corresponding section view of the cartridge of FIG. 9A, according to an example implementation of the present disclosure;

FIG. 11 illustrates a perspective section view of an aerosol delivery device showing portions of the airflow and aerosol paths, according to an example implementation of the present disclosure;

FIG. 12A illustrates a side view of a cartridge of an aerosol delivery device showing portions of the airflow and aerosol paths, according to an example implementation of the present disclosure;

FIG. 12B illustrates a corresponding section view of the cartridge of FIG. 12A, according to an example implementation of the present disclosure;

FIG. 13 illustrates a bottom perspective view of a cartridge of a control device showing portions of the airflow and aerosol paths, according to an example implementation of the present disclosure;

FIG. 14 illustrates an exploded perspective view of a control device of an aerosol delivery device, according to an example implementation of the present disclosure;

FIG. 15 illustrates a front section view of a control device of an aerosol delivery device, according to an example implementation of the present disclosure;

FIG. 16 illustrates a perspective view of an endcap assembly, according to an example implementation of the present disclosure;

FIG. 17A illustrates subassemblies of the control device of FIG. 14, according to an example implementation;

FIG. 17B illustrates subassemblies of the control device of FIG. 14, according to an example implementation;

FIG. 17C illustrates subassemblies of the control device of FIG. 14, according to an example implementation;

FIG. 18 illustrates a perspective view of a cartridge of an aerosol delivery device, according to example implementations of the present disclosure;

FIG. 19 illustrates an exploded perspective view of a cartridge of an aerosol delivery device, according to an example implementation of the present disclosure;

FIG. 20 illustrates a side section view of a cartridge of an aerosol delivery device, according to an example implementation of the present disclosure;

FIG. 21A illustrates subassemblies of a cartridge of an aerosol delivery device, according to an example implementation of the present disclosure;

FIG. 21B illustrates subassemblies of a cartridge of an aerosol delivery device, according to an example implementation of the present disclosure;

FIG. 22 illustrates an exploded perspective view of a control device of an aerosol delivery device, according to an example implementation of the present disclosure;

FIG. 23 illustrates a front section view of a control device of an aerosol delivery device, according to an example implementation of the present disclosure;

FIG. 24 illustrates an exploded perspective view of a cartridge of an aerosol delivery device, according to an example implementation of the present disclosure;

FIG. 25 illustrates a front section view of a cartridge of an aerosol delivery device, according to an example implementation of the present disclosure;

FIG. 26 illustrates a side section view of a cartridge of an aerosol delivery device, according to an example implementation of the present disclosure;

FIG. 27 illustrates a front section view of a cartridge and a control device of an aerosol delivery device, according to an example implementation of the present disclosure;

FIG. 28 illustrates an exploded perspective view of a control device of an aerosol delivery device, according to an example implementation of the present disclosure;

FIG. 29 illustrates a front section view of a control device of an aerosol delivery device, according to an example implementation of the present disclosure;

FIG. 30 illustrates a perspective partial section view of a control device of an aerosol delivery device, according to an example implementation of the present disclosure;

FIG. 31 illustrates a perspective view of an endcap assembly, according to an example implementation of the present disclosure;

FIG. 32 illustrates an exploded perspective view of a cartridge of an aerosol delivery device, according to an example implementation of the present disclosure;

FIG. 33 illustrates a front section view of a cartridge of an aerosol delivery device, according to an example implementation of the present disclosure;

FIG. 34 illustrates a side section view of a cartridge of an aerosol delivery device, according to an example implementation of the present disclosure;

FIG. 35 illustrates a side section view of a control device of an aerosol delivery device showing airflow through the control device, according to an example implementation of the present disclosure;

FIG. 36 illustrates an angled side section view of a cartridge of an aerosol delivery device showing air and aerosol flow paths, according to an example implementation of the present disclosure;

FIG. 37 illustrates an angled front section view of a cartridge of an aerosol delivery device showing air and aerosol flow paths, according to an example implementation of the present disclosure; and FIG. 38 illustrates a bottom perspective view of a cartridge of an aerosol delivery device showing portions of the air and aerosol flow paths, according to an example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to heat a material (preferably without combusting the material to any significant degree and/or without significant chemical alteration of the material) to form an inhalable substance; and components of such devices have the form of articles that most preferably are sufficiently compact to be considered hand-held devices. That is, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), a heater or heat generation member (e.g., an electrical resistance heating element or other component, which alone or in combination with one or more further elements may be commonly referred to as an "atomizer"), a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

In various implementations, the present disclosure relates to aerosol delivery devices and cartridges and control devices that together comprise an aerosol delivery device. As will be described in more detail below, in various implementations the aerosol delivery device may have improved connectively, airflow, and/or aerosol paths through the device.

An example implementation of an aerosol delivery device 100 of the present disclosure is shown in FIG. 1. As illustrated, the aerosol delivery device 100 includes a control device 200 and a removable cartridge 300. Although only one cartridge is shown in the depicted implementation, it should be understood that, in various implementations, the aerosol delivery device 100 may comprise an interchangeable system. For example, in one or more implementations, a single control device may be usable with a plurality of different cartridges. Likewise, in one or more implementations, a single cartridge may be usable with a plurality of different control devices.

FIG. 2 illustrates a perspective view of the control device 200, and FIG. 3 illustrates an exploded perspective view of the control device 200. As shown in the figures, the control device 200 of the depicted implementation generally includes a housing 202 defining an outer wall 204, an upper frame 206, an upper frame seal 208, a pressure sensor seal 210, a lower frame 212, a control component 214, a battery 216, a vibration motor 218, a motor housing 220, a pin seal 222, an end cap 224, and a light diffuser 226. The arrangement of these components is illustrated in FIGS. 4A and 4B, and FIGS. 5A and 5B. In particular, FIG. 4A illustrates a front view of the control device 200, and FIG. 4B illustrates a corresponding section view of the control device 200. Likewise, FIG. 5A illustrates a side view of the control device 200, and FIG. 5B illustrates a corresponding section view of the control device 200. As illustrated in the figures, the upper frame 206 of the control device 200 defines a cartridge receiving chamber 230 within which a cartridge may be coupled. The control device 200 also includes a pair of opposite indication windows 232 that are defined through the outer wall 204 of the housing 202, as well as through the upper frame 206. As will be described in more detail below, in various implementations the indication windows 232 may provide a user with the ability to view one or more components (and/or conditions thereof) of an installed cartridge. It will be appreciated, however, that the illustrated indication windows 232 are provided by way of example and not by way of limitation. For example, alternative implementations may include an indication window having a different shape than that illustrated. As another example, some implementations may include only a single indication window. In still other implementations, there need not be any indication windows. In the depicted implementation, the upper frame 206 and the housing 202 represent different parts; however, in other implementations, the upper frame and the housing may be continuously formed such that they comprise the same part.

In the depicted implementation, the housing 202 comprises a metal material, such as, for example, aluminum; however, in other implementations the housing may comprise a metal alloy material, and in still other implementations the housing may comprise a molded plastic material. In the depicted implementation, one or more of the housing 202, upper frame 206, lower frame 212, and end cap 224 may be made of a molded polymer material, such as, for example, a molded plastic material (e.g., polybutylene tere- phthalate (PBT), acrylonitrile butadiene styrene (ABS), polyethylene, polycarbonate, Polyamide (Nylon), high impact polystyrene, polypropylene, and combinations thereof). In other implementations, one or more of these components may be made of other materials, including, for example, metal materials (e.g., aluminum, stainless steel, metal alloys, etc.), glass materials, ceramic materials (e.g., alumina, silica, mullite, silicon carbide, silicon nitride, alu- minum nitride, etc.), composite materials, and/or any com- binations thereof.

In the depicted implementation, the lower frame 212 is configured to contain the battery 216 in an interior area thereof. In the depicted implementation, the battery may comprise a lithium polymer (LiPo) battery; however various other batteries may be suitable. Some other examples of batteries that can be used according to the disclosure are described in U.S. Pat. App. Pub. No. 2010/0028766 to Peckerar et al., the disclosure of which is incorporated herein by reference in its entirety. In some implementations, other types of power sources may be utilized. For example, in various implementations a power source may comprise a replaceable battery or a rechargeable battery, solid-state battery, thin-film solid-state battery, rechargeable superca- pacitor or the like, and thus may be combined with any type of recharging technology, including connection to a wall charger, connection to a car charger (e.g., cigarette lighter receptacle, USB port, etc.), connection to a computer, such as through a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, a wireless charger, such as a charger that uses inductive wireless charging (including for example, wireless charging accord- ing to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapaci- tor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapaci- tor. Examples of power supplies that include supercapacitors are described in U.S. Pat. App. Pub. No. 2017/0112191 to Sur et al., which is incorporated herein by reference in its entirety.

The aerosol delivery device 100 of the depicted imple- mentation includes a control mechanism in the form of the control component 214, which is configured, in part, to control the amount of electric power provided to the heating member of the cartridge. Although other configurations are possible, the control component 214 of the depicted imple- mentation comprises a circuit board 234 (e.g., a printed circuit board (PCB)) that includes both rigid and flexible portions. In particular, the circuit board 234 of the depicted implementation includes a rigid central section 215 and two rigid end sections comprising a proximal end section 217 and a distal end section 219, with each of the end sections 217, 219 being connected to the central section 215 by a respective flexible connection. In such a manner, when the lower frame 212, battery 216, and circuit board 234 are assembled into the control device 200, the central section 215 of the circuit board 234 is configured to be disposed proximate a major surface of the battery 216, and the two end sections 217, 219 are configured to be disposed substantially perpendicular to the central section 215. In particular, the proximal end section 217 of the circuit board 234 is configured to extend over the top of the lower frame 212, and the distal end section 219 is configured to extend over the bottom of the lower frame 212. The lower frame 212 of the control device 200 is also configured to contain the motor housing 220, into which the vibration motor 218 is received. In various implementations, the vibration motor 218 may provide haptic feedback relating to various operations of the device 100.

The central section 215 of the depicted implementation also includes an indicator in the form of a light source 221. In some implementations, the light source may comprise, for example, at least one light emitting diode (LED) capable of providing one or more colors of light. In other implementations, the light source may be configured to illuminate in only one color, while in other implementations, the light source may be configured to illuminate in variety of different colors. In still other implementations, the light source may be configured to provide white light. In the depicted implementation, the light source 221 comprises an RGB (red, green, blue) LED that is configured to provide a variety of colors of light, including white light. The central section 215 of the depicted circuit board 234 also includes electrical contacts 223 that are configured to operatively connect the circuit board 234 to the vibration motor 218. Other types of electronic components, structures and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference. Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In the depicted implementation, the light source 221 is covered by the light diffuser 226, a portion of which is configured to be received by the end cap 224. In such a manner, when assembled, the light diffuser 226 is positioned in or proximate an aperture 225 defined in the outer wall 204 of the housing 202 and proximate a distal end thereof. In the depicted implementation, the aperture 225 comprises a narrow, elongate opening; however, in other implementations, the aperture may be provided in any desired shape and may be positioned at any location on the control device 200. In some implementations, the light diffuser 226 may comprise a transparent or translucent member configured to allow a user to view the light source 221 from the outside of the housing 202. In the depicted implementation, the light diffuser 226 may be made of a molded polymer material, such as, for example, a molded plastic material (e.g., acrylonitrile butadiene styrene (ABS), polyethylene, polycarbonate, Polyamide (Nylon), high impact polystyrene, polypropylene, and combinations thereof), although other materials, including glass, are possible. In various implementations, further indicators (e.g., other haptic feedback components, an audio feedback component, or the like) can be included in addition to or as an alternative to the indicators included in the depicted implementation. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties.

Although other configurations are possible, the proximal end section 217 of the circuit board 234 of the depicted implementation includes a pair of conductive pins 236A, 236B, as well as a pressure sensor 240. In the depicted implementation, the conductive pins 236A, 236B comprise spring-loaded pins (e.g., electrical pogo pins) that extend through the upper frame 206 such that portions of the ends of the pins 236A, 236B extend into the cartridge receiving chamber 230 and are biased in that position due to the force of the internal springs of the conductive pins 236A, 236B. In such a manner, when a cartridge is coupled with the control device 200, the conductive pins 236A, 236B are configured to contact corresponding features of the cartridge and deflect downward (e.g., toward the lower frame 212) against the force of the springs, thus operatively connecting the installed cartridge with the control component 214 and the battery 216. In the depicted implementation, the conductive pins 236A, 236B comprise gold plated metal pins; however, other materials or combinations of materials, which may also include coatings and/or platings of electrically conductive materials, are possible. Examples of electrically conductive materials, include, but are not limited to, copper, aluminum, platinum, gold, silver, iron, steel, brass, bronze, graphite, conductive ceramic materials, and/or any combination thereof. Although other profiles are possible, the ends of the conductive pins 236A, 236B of the depicted implementation have a rounded profile such that deflection of the conductive pins 236A, 236B is facilitated when a cartridge is inserted into the cartridge receiving chamber 230. In other implementations, the conductive pins may be positioned in other locations of the cartridge receiving chamber 230, such as, for example, proximate the top of the cartridge receiving chamber 230. In other implementations, the conductive pins may be positioned at a point on the sides of the upper frame 206 between the proximal end of the outer housing 202 and the bottom wall of the upper frame 206. Further, in still other implementations the conductive pins may be positioned between a midpoint of the sidewalls and the proximal end of the outer housing 202 (i.e., in an upper half of the sidewalls). Alternatively, the conductive pins may be positioned between a midpoint of the sidewalls and the bottom wall of the inner frame wall (e.g., in a lower half of the sidewalls). Moreover, in still other implementations, the conductive pins may be present at any position of the upper frame 206.

In various implementations, the aerosol delivery device 100 may include an airflow sensor, pressure sensor, or the like. As noted above, the control component 214 of the depicted implementation includes a pressure sensor 240, which is positioned proximate and below the cartridge receiving chamber 230. The position and function of the pressure sensor 240 of the depicted implementation will be described below; however, in other implementations an airflow or pressure sensor may be positioned anywhere within the control device 200 so as to subject to airflow and/or a pressure change that can signal a draw on the device and thus cause the battery 216 to delivery power to the heating member of the cartridge 300. Various configurations of a printed circuit board and a pressure sensor, for example, are described in U.S. Pat. Pub. No. 2015/0245658 to Worm et al., the disclosure of which is incorporated herein by reference in its entirety. In the absence of an airflow sensor, pressure sensor, or the like, an aerosol delivery device may be activated manually, such as via a pushbutton that may be located on the control device and/or the cartridge. For example, one or more pushbuttons may be used as described in U.S. Pat. App. Pub. No. 2015/0245658 to Worm et al., which is incorporated herein by reference in its entirety. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pat. App. Pub. No. 2016/0158782 to Henry et al., which is incorporated herein by reference in its entirety.

Although not included in the depicted implementation, some implementations may include other types of input elements, which may replace or supplement an airflow or pressure sensor. The input may be included to allow a user to control functions of the device and/or for output of information to a user. Any component or combination of components may be utilized as an input for controlling the function of the device. In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In the depicted implementation, the pressure sensor seal 210 is configured to cover the pressure sensor 240 to protect it from any liquid and/or aerosol from an installed cartridge. In addition, the pressure sensor seal 210 of the depicted implementation is configured to seal the conductive pins

236A, 236B. In such a manner, the pressure sensor seal 210 of the depicted implementation may be made of silicone rubber, boron nitride (BN) rubber, natural rubber, thermoplastic polyurethane, or another resilient material. In the depicted implementation, the upper frame seal 208 is configured to be positioned proximate and above the pressure sensor seal 210, such that a pair of upper frame seal tubes 209A, 209B (see FIG. 6) of the upper frame seal 208 extend through the upper frame 206 and into the cartridge receiving chamber 230. The upper frame seal 208 of the depicted implementation may also be made of a silicone, thermoplastic polyurethane, or another resilient material.

Although other configurations are possible, the distal end section 219 of the circuit board 234 includes the external connection element 238. In various implementations, the external connection element 238 may be configured for connecting to an external connector and/or a docking station or other power or data source. For example, in some implementations an external connector may comprise first and second connector ends that may be interconnected by a union, which may be, for example, a cord of variable length. In some implementations, the first connector end may be configured for electrical and, optionally, mechanical connection with the device (100,200), and the second connector end may be configured for connection to a computer or similar electronic device or for connection to a power source. An adaptor including a USB connector at one end and a power unit connector at an opposing end is disclosed in U.S. Pat. App. Pub. No. 2014/0261495 to Novak et al., which is incorporated herein by reference in its entirety. In the depicted implementation, the pin seal 222 is configured to seal the interface between the external connection element 238 and the end cap 224. In such a manner, the pin seal 222 of the depicted implementation may be made of a silicone, thermoplastic polyurethane, or another resilient material. In the depicted implementation, one or more pins of the external connection element 238 may extend through the end cap 224 of the control device as noted above.

In various implementations, the control device may include one or more components configured to meet battery outgassing requirements under UL 8139. For example, the control device may include an end cap configured to eject in the event that sudden pressurization occurs within the control device enclosure. In one implementation, the end cap may include retaining pins that extend substantially perpendicularly from a wall of the end cap. The retaining pins may be configured to mate with receiving features (e.g., holes) in a frame of the control device to establish a friction fit or press fit that may be overcome if an internal pressure within the control device housing exceeds a defined internal pressure.

FIG. 6 illustrates a perspective partial section view of a control device of an aerosol delivery device. In particular, FIG. 6 illustrates a partial section view of the housing 202, upper frame 206, upper frame seal 208, pressure sensor seal 210, pressure sensor 240), and lower frame 212 of the control device 200. As shown in the figure, a portion of the conductive pins 236A, 236B of the control component 214 extend through the upper frame 206. In particular, a portion of the conductive pins 236A, 236B of the depicted implementation, which as noted above comprise spring-loaded contacts, extend through a recessed surface 244 of the upper frame 206 and into the cartridge receiving chamber 230. In addition, a portion of the upper frame seal tubes 209A, 209B (which define respective seal tube channels 211A, 211B) of the upper frame seal 208 extend through the upper frame 206 and are exposed in the cartridge receiving chamber 230. As will be described in more detail below, regardless of the orientation of an installed cartridge, the conductive pins 236A, 236B and one of the upper frame seal tubes 209A, 209B are configured to substantially align with corresponding features of an installed cartridge.

As also shown in the figure, the upper frame 206 includes a pair of magnets 246A, 246B that are also exposed in the cartridge receiving chamber 230. In various implementations, the magnets 246A, 246B may comprise any type of magnets, including rare earth magnets. For example, in some implementations, one or more of the magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more of the magnets may comprise Samarium Cobalt magnets (also known as SmCo magnets). In still other implementations, one or more of the magnets may comprise Ceramic/Ferrite magnets. In other implementations, one or more of the magnets may comprise Aluminum-Nickel-Cobalt (AlNiCo) magnets. In any of the foregoing implementations, one or more of the magnets may be plated and/or coated. For example, in some implementations, one or more of the magnets may be coated with nickel. In other implementations, one or more magnets may be coated with one or more of zinc, tin, copper, epoxy, silver and/or gold. In some implementations, one or more of the magnets may be coated with combinations of these materials. For example, in one implementation, one or more of the magnets may be coated with nickel, copper, and nickel again. In another implementation, one or more of the magnets may be coated with nickel, copper, nickel, and a top coating of gold.

In the depicted implementation, each magnet 246A, 246B is substantially surrounded by a respective location feature 248A, 248B of the upper frame 206, wherein the location features 248A, 248B also extend into the cartridge receiving chamber 230. Likewise, each upper frame seal tube 209A, 209B of the upper frame seal 208 is substantially surrounded by a respective location feature 250A, 250B. As will be discussed in more detail below, one or more of the location features 248A, 248B, 250A, 250B of the upper frame 206 are configured as stopping or vertical locating features for an installed cartridge and are thus configured to position the cartridge 300 with respect to the recessed surface 244 of the upper frame 206 of the control device 200.

As noted above, a portion of the cartridge 300 is configured to be coupled with the cartridge receiving chamber 230 of the inner frame 206 of the control device 200 such that mechanical and electrical connections are created between the cartridge 300 and the control device 200. In particular, when the cartridge 300 of the depicted implementation is coupled with the upper frame 206 of the control device 200, a magnetic connection is created between the magnets 246A, 246B located in the upper frame 206 and corresponding features of the cartridge 300. In addition, when the cartridge 300 of the depicted implementation is coupled with the inner frame 206, an electrical connection is created between the pair conductive pins 236A, 236B of the control device 200 and corresponding features of the cartridge 300. As such, when the cartridge 300 is received in the receiving chamber 230 of the control device 200, the cartridge 300 may be operatively connected to the control component 214 and the battery 216 of the control device 200. Thus, when the cartridge 300 of the depicted implementation is coupled with the control device 200, the cartridge 300 is mechanically biased into connection with the control device 200 such that electrical connection is maintained between the cartridge and the control device. It should be understood that for the purposes of the present disclosure, the term "operatively connected" and other related forms thereof should be interpreted broadly so as to encompass components that are directly connected and/or connected via one or more additional components.

FIG. 7 illustrates a perspective view of the cartridge 300, and FIG. 8 illustrates an exploded perspective view of the cartridge 300. Although other configurations are possible, the cartridge 300 of the depicted implementation generally includes a mouthpiece 302, a mouthpiece insert 304, an upper aerosol channel insert 306, an upper cartridge seal 308, a tank 310 that defines a tank wall 311, a lower cartridge seal 312, a base member 314, a liquid transport element (e.g., a wick) 316, a heating member 318, a pair of heater connectors 320A, 320B, a pair of O-ring seals 322A, 322B, a pair of metal inserts 324A, 324B, and a bottom cap 326. The arrangement of these components is illustrated in FIGS. 9A, 9B, 10A, and 10B. In particular, FIG. 9A illustrates a front view of the cartridge 300, and FIG. 9B illustrates a corresponding section view of the cartridge 300. Likewise, FIG. 10A illustrates a side view of the cartridge 300, and FIG. 10B illustrates a corresponding section view of the cartridge 300.

As shown in the figures, the mouthpiece 302 of the depicted implementation defines a proximal end and a distal end, with the proximal end of the mouthpiece 302 defining an exit portal 315 therein. In the depicted implementation, the mouthpiece insert 304 is configured to be located proximate the proximal end of the mouthpiece 302 such that it extends through the exit portal 315 thereof. In the depicted implementation, mouthpiece 302 and the mouthpiece insert 304 may be made of a molded polymer material, such as, for example, a molded plastic material (e.g., polypropylene, acrylonitrile butadiene styrene (ABS), polyethylene, polycarbonate, Polyamide (Nylon), high impact polystyrene, and combinations thereof), although other materials are possible. The mouthpiece insert 304 of the depicted implementation includes a flange feature on a lower portion thereof such that the mouthpiece insert 304 may be installed from inside the mouthpiece 302 and may be configured for a press or snap-fit connection with the exit portal 315. In other implementations, other attachment methods are possible (e.g., via adhesives, heat staking/welding, ultrasonic welding, etc.). In still other implementations, the mouthpiece and mouthpiece insert may be constructed using an insert molding or overmolding process such that the mouthpiece 302 and the mouthpiece insert 304 comprise a unitary part. The mouthpiece 302 of the depicted implementation is configured to be secured to the tank 310 via snap features included on one or both of the mouthpiece 302 and tank 310; however, other attachment methods are possible (e.g., via adhesives, heat staking/welding, ultrasonic welding, etc.).

In some implementations, the mouthpiece insert may exhibit a color associated with a distinctive characteristic of the cartridge. For example, in some implementations a cartridge of the present disclosure may include a liquid composition that includes a distinctive characteristic such as, for example, a particular flavorant (as discussed infra), or a specific strength of nicotine, although any characteristic of the cartridge may be considered a distinctive characteristic. For the purposes of the current description, the term "color" should be interpreted broadly, for example covering any color or any shade of the same color. It should also be noted that in some implementations, certain colors may be commonly associated with particular distinctive characteristics (e.g., the color green may be associated with a mint flavorant, and the color red may be associated with an apple flavorant); however, in other implementations, certain colors may be associated with particular distinctive characteristics according to an index or guide, which may be provided or made available to a user. Examples of distinctive characteristics are described in U.S. patent application Ser. No. 16/171,920, titled Aerosol Delivery Device with Flavor Indicator, which is incorporated herein by reference in its entirety.

The tank 310 of the depicted implementation defines a proximal end and a distal end, wherein the mouthpiece 302 is configured to engage the proximal end of the tank 310 and the bottom cap 326 is configured to engage the distal end of the tank 310. In the depicted implementation, the tank 310 also defines a reservoir cavity 328 that includes a closed proximal end and an open distal end. As such, the reservoir cavity 328 of the tank 310 is configured to contain a liquid composition (e.g., an e-liquid or aerosol precursor composition) therein. The closed proximal end of the reservoir cavity 328 allows the cavity to create a reliable seal on the top side of the liquid composition column. This may prevent the seepage/entry of air into the reservoir cavity from the top end when the cartridge is held upright. This may also prevent air from entering from the top of the liquid composition column, which may create a vacuum and may reduce the potential of the liquid composition to leak from the bottom of the tank through the liquid transport element or other passages.

Although other configurations are possible, in the depicted implementation a pair of internal aerosol flow tubes 333A, 333B are defined on opposite sides of the reservoir cavity 328 of the tank 310. In the case of an injection molded tank 310, the internal aerosol flow tubes 333A, 333B are configured to be molded therein. As will be described in more detail below, aerosol produced in a vaporization chamber of the cartridge 300 is configured to travel through the aerosol flow tubes 333A, 333B for delivery to a user.

In the depicted implementation, the tank wall 311 is configured to be transparent or translucent so that the liquid composition contained therein may be visible externally. As such, in the depicted implementation the entire tank wall 311 is configured to be transparent or translucent. Alternatively, in some implementations, only a portion of the tank wall or only a single side of the tank wall may be transparent or translucent while the remaining portions of the tank wall may be substantially opaque. In other implementations, the tank wall may be substantially opaque, and a strip extending from the proximal end of the tank to the distal end of the tank may be transparent or translucent. In further implementations, the tank wall may be colored. In some implementations, the color can be configured so that the liquid composition within the tank is still visible, such by using a transparent or translucent outer tank wall. In other implementations, the tank wall can be configured so that the outer tank wall has substantially opaque color. In the depicted implementation, the tank 310 may be made of a molded polymer material, such as, for example, a molded plastic material (e.g., a copolyester material, such as, for example, Tritan™ copolyester, acrylonitrile butadiene styrene (ABS), polyethylene, polycarbonate, Polyamide (Nylon), high impact polystyrene, polypropylene, and combinations thereof), although other materials, including glass, are possible.

The indication window 232 of the depicted implementation of the control device 200 is configured so that at least a portion of the tank 310 and at least a portion of the bottom cap 326 are visible when the cartridge 300 is engaged with the control device 200. As noted above, in some implementations at least a portion of the tank wall 311 may be configured to be at least partially transparent or translucent so that the liquid composition contained therein is visible externally. Thus, the relative amount of any liquid composition present in the tank 310 may be visible through the indication window 232 when the cartridge 300 is engaged with the control device 200. As illustrated in FIGS. 1-6, the indication window 232 of the depicted implementation is located near the proximal end of the control device 200 and is configured as an elongate oval shaped cut-out in the outer wall 204 of the housing 202 and the upper frame 206 of the control device 200. It should be understood that in other implementations, the indication window may have any other shapes and/or locations. For example, in some implementations the indication window may be configured as a notch extending from the proximal end of the outer wall of the control device a distance toward the distal end of the device. In still other implementations, the indication window may be configured so as not to have any open borders and thus may expressly exclude a notch configuration as noted above. In some implementations, the indication window may be completely open, and in other implementations, the indication window may have a transparent member (e.g., glass or plastic) positioned in the opening defined by the indication window or covering the indication window on one or both of the inner surface and outer surface of the outer wall of the control device. It should be understood that in some implementations, the indication window may be formed in part by the cartridge and in part by the control device. For example, in some implementations, the cartridge may include a portion of the indication window (e.g., a top portion of an indication window), and the control device may include a separate portion of the indication window (e.g., a bottom portion of the indication window).

Although other configurations are possible, in the depicted implementation the proximal end of the tank 310 is configured to receive the upper cartridge seal 308, which is configured to form a substantially air tight and liquid tight seal between the tank 310 and the mouthpiece 302. As such, the upper cartridge seal 308 may be made of silicone rubber, boron nitride (BN) rubber, natural rubber, thermoplastic polyurethane, or another resilient material. In the depicted implementation, the upper cartridge seal 308 is also configured to receive and seal the upper aerosol channel insert 306 (see also FIG. 11).

For aerosol delivery systems that are characterized as electronic cigarettes, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

In the depicted implementation, the liquid composition, sometime referred to as an aerosol precursor composition or a vapor precursor composition or "e-liquid", may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In the depicted implementation, the reservoir cavity 328 is configured to hold approximately 1.5 mL of aerosol precursor composition. In other embodiments, the reservoir cavity 328 is configured to hold about 1 ml or more, about 2 ml or more, about 5 ml or more, or about 10 ml or more of the aerosol precursor composition.

In some implementations, the liquid composition may include one or more flavorants. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, verba santa, bacopa monniera, *gingko biloba*, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be understood that reference to a flavorant should not be limited to any single flavorant as described above, and may, in fact, represent a combination of one or more flavorants.

As shown in the figures, the cartridge 300 of the depicted implementation also includes a base member 314, which is configured to engage and cover the open distal end of the reservoir cavity 328 of the tank 310. The lower seal 312 of the depicted implementation is configured form a substantially air tight and liquid tight seal between a lower portion of the tank 310 and the bottom cap 326 (see also FIG. 11). In particular, the lower seal 312 is configured to be located within a groove on an outer surface of the base member 314 so as to facilitate a substantially air tight and liquid tight seal between the base member 314 and tank 310. In various implementations, the lower seal 312 may be made of silicone rubber, boron nitride (BN) rubber, natural rubber, thermoplastic polyurethane, or another resilient material. In the depicted implementation, the base member 314 may be made of a molded polymer material, such as, for example, a molded plastic material (e.g., acrylonitrile butadiene styrene (ABS), polyethylene, polycarbonate, Polyamide (Nylon), high impact polystyrene, polypropylene, and combinations thereof), although other materials are possible. The base member 314 of the depicted implementation also includes a plurality of slots 335 (see also FIG. 11) that are configured to provide liquid flow passages for the liquid composition contained in the reservoir cavity 328 of the tank 310 in order to facilitate transfer of the liquid to the liquid transport element 316. In some implementations, the slots 335 may also provide retention of some liquid even when the bulk liquid composition in the reservoir cavity 328 is not in contact with the base member 314 (such as, for example, when the aerosol delivery device 100 is upside down).

As shown in the figures, the liquid transport element 316 is disposed within the base member 314 and extends between the liquid composition in the reservoir cavity 328 and the heating member 318 (see also FIG. 11). In the depicted implementation, the liquid transport element 316 is formed of a cotton material and, when installed in the cartridge 300, has a curved shape. In other implementations, however, the liquid transport element 316 may have other shapes and may be formed of a variety of materials configured for transport of a liquid, such as by capillary action. For example, in some implementations the liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In other implementations, the liquid transport element may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference in their entireties.

As shown in the figures, the heating member 318 of the depicted implementation is also configured to be disposed within the base member 314. In particular, the heating member 318 of the depicted implementation comprises a heating element that has a substantially flat profile (e.g., initially formed as a substantially planar element). Although other implementations may differ, in the depicted implementation the heating member 318 includes a first end, a second end, and a heater loop connecting the first end and the second end. In particular, the heater loop of the depicted implementation comprises a serpentine pattern of heater traces that are connected at respective ends thereof and that extend substantially transverse to a longitudinal axis of the heating member to connect the first end to the second end. While in some implementations the heater traces may be solid, the heater traces of the depicted implementation comprise a plurality of split traces. In the depicted implementation, the edges of the heating member are substantially solid and the plurality of split traces are located in a central area of the heating member. In such a manner, the heater loop of the depicted implementation may be configured to concentrate heat in an area of the heating element configured to be in contact with the liquid transport element 316.

While in some implementations the heating member may maintain a substantially flat profile when installed in a cartridge, when the heating member 318 of the depicted implementation is installed in the cartridge 300 it has a curved or bowed shape corresponding to the curved shape of the liquid transport element 316 (see also FIG. 11). In such a manner, the heating member 318 in the installed position contacts a bottom surface of the liquid transport element 316. In the depicted implementation, the curved form of the flat heating member 318 may provide a large ratio of cross-sectional flow area to flow path length through the liquid transport element 316. This may provide increased performance with respect to delivery of the liquid composition to the liquid transport element 316. When installed, edges of the heating member 318 are configured to engage the base member 314 such that the heating member 318 maintains its curved shape. In such a manner, the curvature of the heating member 318 may also provide a compressive force against the liquid transport element 316. In addition, the spring recover force of the heating member 318 allows the edges of the heating member 318 to locate or lock into the base member 314, which may reduce or eliminate any need for additional features configured to hold the heating member 318 in the base member 314 from the other side. The installed curvature of the heating member 318 may also bias deflection of the heating member 318 that may occur with thermal expansion towards the liquid transport element 316, thus helping to maintain thermal contact between the heating member 318 and the liquid transport element 316. In the depicted implementation, the liquid transport element 316 and the heating member 318 comprise a heating assembly 334, which, together with the base member 314 and the bottom cap 326, define a vaporization chamber 332.

It should be noted that some implementations need not include a heating assembly, but, rather, may include an atomization assembly configured to generate an aerosol in another manner. Some examples of atomization assemblies that generate aerosols in other ways can be found, for example, in U.S. application Ser. No. 16/544,326, filed on Aug. 19, 2019, and titled Detachable Atomization Assembly for Aerosol Delivery Device, which is incorporated herein by reference in its entirety.

In the depicted implementation, the heating member 318 may be made of a metal material, such as a stainless steel material, including, but not limited to, 316L, 316, 304, or 304L stainless steel. In other implementations, the heating member may be made of a different material, such as, for example, Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. Other heaters are described in U.S. Pat. App. Pub. No. 2016/0345633 to DePiano et al., which is incorporated herein by reference in its entirety.

Although in other implementations additional and/or differing contact features may be provided, the heating member 318 of the depicted implementation includes a pair of contact holes 331A, 331B that are configured to connect the heating member 318 to the heater connectors 320A, 320B of the cartridge 300. In depicted implementation, the heater connectors 320A, 320B are made of a conductive material and are plated with nickel and/or gold. Examples of conductive materials include, but are not limited to, copper, aluminum, platinum, gold, silver, iron, steel, brass, bronze, graphite, conductive ceramic materials, and/or any combination thereof. In the depicted implementation, the contact holes 331A, 331B are configured to have an inner diameter that is less than an outer diameter of the mating portions of the heater connectors 320A, 320B. In some implementations, the contact holes may include one or more features (e.g., one or more fingers or extensions) that create an effective inner diameter that is less than an outer diameter of the mating portion of the heater connectors 320A, 320B. In such a manner, the contact holes 331A, 331B of the heating member 318 may create an interference fit with the upper ends of the heater connectors 320A, 320B such that the heating member 318 may maintain electrical contact with the heater connectors 320A, 320B. In the depicted implementation, the lower end of the heater connectors 320A, 320B are sealed around respective circumferential surfaces thereof by the pair of O-rings 322A, 322B, which are configured to form a substantially air tight and liquid tight seal between the heater connectors 320A, 320B and the bottom cap 326. In such a manner, the O-rings 322A, 322B of the depicted implementation may be made of silicone rubber, boron nitride (BN) rubber, natural rubber, thermoplastic polyurethane, or another resilient material.

The bottom cap 326 of the depicted implementation is configured to be secured to the distal end of the tank 310 via snap features included on one or both of the bottom cap 326 and tank 310; however, other attachment methods are possible (e.g., via adhesives, heat staking/welding, ultrasonic welding, etc.). In the depicted implementation, the bottom cap 326 of the cartridge 300 includes a cartridge air inlet channel 330, which is located in an approximate center of a bottom surface of the bottom cap 326. Although other configurations are possible, in the depicted implementation the cartridge air inlet channel 330 has a nozzle-like shape. In particular, the cartridge air inlet channel 330 of the depicted implementation includes a first portion (proximate the bottom surface of the bottom cap 326), which has a substantially cylindrical shape and a second portion, which has a substantially conical shape and leads to the vaporization chamber 332. In such a manner, the internal diameter of the cartridge air inlet channel 330 decreases before leading to the vaporization chamber 332. This configuration may help to keep the air inlet channel 330 relatively clear of liquid build-up leading into the vaporization chamber 332.

Although other configurations are possible, the cartridge 300 of the depicted implementation also includes a pair of metal inserts 324A, 324B that are positioned in the bottom cap 326 and are configured to be exposed through the bottom surface thereof. In some implementations, the metal inserts 324A, 324B may be configured for a press or snap fit connection with the bottom cap 326. In other implementations, the metal inserts may be a product of an insert molding process such that the bottom cap 326 and the metal inserts 324A, 324B form a unitary part. In the depicted implementation, the metal inserts 324A. 324B comprise any material configured to be attracted by a magnet, such as various ferromagnetic materials, including, but not limited, to iron, nickel, cobalt, alloys such as steel, and/or any combination thereof.

As noted above, when the cartridge 300 is coupled with the cartridge receiving chamber 230 of the control device 200, mechanical and electrical connections are created between the cartridge 300 and the control device 200. In particular, when the cartridge 300 of the depicted implementation is coupled with the upper frame 206 of the control device 200, a magnetic connection is created between the magnets 246A, 246B located in the upper frame 206 and the metal inserts 324A, 324B located in the bottom cap 326 of the cartridge 300. In addition, when the cartridge 300 of the depicted implementation is coupled with the inner frame 206, an electrical connection is created between the pair of conductive pins 236A, 236B of the control device 200 and the heater connectors 320A, 320B of the cartridge 300. Thus, when the cartridge 300 of the depicted implementation is coupled with the control device 200, the cartridge 300 is mechanically biased into connection with the control device 200 such that electrical connection is maintained between the cartridge 300 (and, in particular the heating assembly 334) and the control device (and in particular, the control component 214 and the battery 216).

When the cartridge 300 of the depicted implementation is coupled with the control device 200, the electrical connection between the control device 200 and the heating member 318 of the cartridge 300 (via the conductive pins 236A, 236B of the control device 200 and the heater connectors 320A, 320B of the cartridge) allows the control body 200 to direct electrical current to the heating member 318. In the depicted implementation, this may occur when a puff on the aerosol delivery device 100 is detected (or, in other implementations, via actuation by the user, such as, for example, via a pushbutton). When a user of the aerosol device 100 of the depicted implementation draws on the mouthpiece 302, inlet airflow is directed into the device 100 via a gap 400 (see FIG. 11) between the cartridge 300 (e.g., an outer wall of the cartridge 300) and the control device 200 (e.g., an inner wall of the control device 200 defining the receiving chamber 230 thereof).

In the depicted implementation, the gap 400 comprises a peripheral gap that extends around substantially the entire periphery of the cartridge 300. It should be understood that in other implementations, the gap need not extend around the entire periphery of the cartridge, for example in some implementations the gap may comprise one or more gaps that extend around a portion of the periphery of the cartridge rather than the entire periphery, and in some implementations, the gap may comprise one or more individual holes. As shown in the figures, the gap 400 originates at an interface between an outside surface of the cartridge 300 and an inside surface of the control device 200. In particular, the gap 400 originates at the interface of an outer surface of the mouthpiece 302 of the cartridge 300 and a top edge of the outer wall 204 of the housing 202 of the control device 200. In other implementations, however, the gap may originate at another interface between the cartridge and the control device. For example, in one implementation the gap may originate at an interface between an outside surface of the cartridge below the mouthpiece and inside surface of the control device. Although other implementations may differ, in the depicted implementation the opening defined by the top edge of the outer wall of the housing 202 is greater in size than the outer peripheral surface of the mouthpiece 302 such that a maximum perimeter of the cartridge 300 is wholly received within the receiving chamber 230. In addition, as shown in FIG. 11, when the cartridge 300 of the depicted implementation is coupled to the control device 200, a portion of the mouthpiece 302 extends below the top edge of the outer wall of the housing 202 and into the receiving chamber 230.

In the depicted implementation, the gap 400 between the cartridge 300 and the control device 200 is established and maintained by features of the cartridge 300 and the control device 200. Although other configurations are possible, the upper frame 206 of the depicted implementation includes a plurality of protuberances 260 (see FIG. 6) that are spaced around an inner surface of the upper frame 206 and that are configured to laterally position the cartridge 300. In the depicted implementation, the plurality of protuberances 260 comprise a plurality of raised elongate bosses that extend from an approximate top of the upper frame 206 to a recessed surface 244 thereof. When the cartridge 300 of the depicted implementation is coupled with the control device 200, the plurality of protuberances 260 of the upper frame 206 contact an outer surface of the cartridge 300 (and in particular, an outer surface of the mouthpiece 302 and/or an outer surface of the tank 310 and/or an outer surface of the bottom cap 326). In such a manner, the protuberances 260 position the cartridge 300 laterally with respect to the upper frame 206, thus establishing and maintaining the gap 400. It should be understood that in other implementations, the protuberances may take other forms (including, for example, one or more bumps), and may be located on one or more components of the cartridge rather than (or in addition to) the control device.

As a user draws on the device 100, the air that enters the gap 400 between the cartridge 300) and the control device 200 travels downward around the outside of the cartridge 300 and below the bottom cap 326 thereof. In the depicted implementation, inlet air is permitted to travel below the bottom cap 326 due to the vertical position of the cartridge 300 with respect to the bottom of the cartridge receiving chamber 230. In particular, the vertical position of the cartridge 300 of the depicted implementation is established using one or more of the location features 248A, 248B, 250A, 250B that extend upward from the recessed surface 244 of the upper frame 206, at least one of which is configured to contact the bottom surface of the bottom cap 326 when the cartridge 300 is coupled with the control device 200. In such a manner, when the cartridge 300 is received into the control device 200, the gap between the cartridge 300 and the control device 200 is also established between the bottom of the bottom cap 326 and the recessed surface 244 of the upper frame 206.

As noted above, although other configurations are possible, the bottom cap 326 of the depicted implementation includes an inlet channel 330 that is located in an approximate center of the bottom surface of the bottom cap 326. Because of the gap established between the bottom of the bottom cap 326 and the recessed surface 244 of the upper frame 206, inlet air that travels around the outside of the cartridge 300 and below the bottom cap 326 enters the cartridge 300 through the inlet channel 330 of the bottom cap 326. The air that enters through the inlet channel 330 then enters the vaporization chamber 332 of the cartridge 300 as shown by the beginning of arrowed flow paths shown in FIGS. 11-13. As the air is drawn through the inlet channel 330 into the cartridge 300, the pressure sensor 240 of the control device 200 detects the draw. In the depicted implementation, the pressure sensor 240 may detect a draw by sensing a pressure drop in the cartridge 300. A pressure drop in the cartridge 300 of the depicted implementation is conveyed to the pressure sensor 240 via a single offset pressure channel 342 that is defined in the bottom cap 326 of the cartridge 300. The pair of upper frame seal tubes 209A, 209B of the upper frame seal 208 of the control device 200 are configured such that regardless of the rotational orientation of an installed cartridge 300, when the cartridge 300 is coupled with the control device 200, one of the seal tube channels 211A, 211B of the upper frame seal tubes 209A, 209B will substantially align with the offset pressure channel 342 of the cartridge 300, as shown in FIG. 11. In the depicted implementation, the cavity defined by the pressure sensor seal 210 and the bottom of the upper frame seal 208 (with which the pressure channel 342 communicates when the cartridge 300 is coupled with the control device) represents a substantially sealed cavity. During a draw on the device 100 of the depicted implementation there is substantially little to no air flow through the pressure channel 342, and thus the pressure channel 342 acts as a static pressure line, thereby not substantially affecting the system pressure drop.

When a draw is detected by the pressure sensor 240, the control component 214 directs current through the heating member 318 in order to heat the heating member 318. As the heating member 318 heats, at least a portion of the liquid composition contained in the liquid transport element 316 is vaporized in the vaporization chamber 332. Accordingly, aerosol produced in the vaporization chamber 332 may then directed to the user. In particular, as the air enters the cartridge 300 via the air inlet channel 330, the air travels through the vaporization chamber 332 where it impinges on the heating member 318 substantially perpendicularly thereto and mixes with the vaporized liquid composition to become the aerosol. Due to the geometry of the vaporization chamber 332 and the bottom cap 326, the aerosol is split into two separate paths that extend through the inside of the bottom cap 326 and then through the aerosol flow tubes 333A, 333B that are defined on opposite sides of the reservoir cavity 328 of the tank 310 (see FIGS. 12B and 13). This relatively tortuous configuration may increase the effective flow path length and area for heat sinking, thus providing increased cooling of the aerosol stream prior to reaching the user. As shown in the figures, the two aerosol paths converge at the proximal end of the tank 310 and below the upper aerosol channel insert 306. The recombined aerosol then flows through the upper aerosol channel insert 306 and out of the exit portal 315 of the mouthpiece 300, to the user. It should be understood that the aerosol passages downstream from the air inlet channel 330 inlet are configured to be oversized, in order to minimize any additional system pressure drop created by these passages. In this manner, the device is configured such that the greatest portion of the system pressure drop is present in the location of the pressure channel 342, to maximize the pressure "signal" available to the pressure sensor 240.

Although other configurations are possible, in the depicted implementation, the upper aerosol channel insert 306 is configured to absorb liquid formed by deposition and/or condensation from aerosol formed in the vaporization chamber 332, and is configured to have rigid or semi-rigid properties. As such, the upper aerosol channel insert 306 of the depicted implementation may be made of a fibrous, sintered beaded, or open cell foam material. In such a manner, the upper aerosol channel insert 306 may be configured for a press or snap fit attachment with the mouthpiece 302. The upper aerosol channel insert 306 is also configured to help to prevent accumulation of liquid from exiting the cartridge 300 through the mouthpiece 302. In addition, the upper aerosol channel insert 306 is located in such a way that aerosol produced in the vaporization chamber 332 passes through the insert 306 just prior to exiting the cartridge 300. In the depicted implementation, the inside cavity of the upper aerosol channel insert 306 may also serve as a cooling chamber within which the formed aerosol can be allowed to expand and/or cool before passing through the exit portal 315. In some implementations, the vaporization chamber 332 and the cooling chamber may be configured to have a defined relative volume ratio.

FIG. 14 illustrates an exploded perspective view of a control device of an aerosol delivery device, according to another example implementation of the present disclosure. As shown in the figure, the control device 400 of the depicted implementation generally includes a housing 402 defining an outer wall 404, an upper frame 406, a pressure sensor seal 410, a lower frame 412, a control component 414, a battery 416, a vibration motor 418, a motor housing 420, a pin seal 422, an end cap 424, a light diffuser 426 (shown assembled to the end cap 424), and a vent 439. The control device 400 of the depicted implementation also includes a front foam pad 431, a back foam pad 433, an upper chassis seal 435, and a base seal 437. In the depicted implementation, the front foam pad is configured to be disposed between the battery 416 and the control component 414, and the back foam pad 433 is configured to be disposed between the battery 416 and the lower frame 412. The upper chassis seal 435 is configured to seal around the upper frame 406, and the base seal 437 is configured to seal around the end cap 424. The arrangement of the components of the control device 400 is illustrated in FIG. 15. In particular, FIG. 15 illustrates a front section view of the control device 400. As illustrated in the figure, the upper frame 406 of the control device 400 defines a cartridge receiving chamber 430 within which a cartridge may be coupled. The control device 400 also includes a pair of opposite indication windows 432 that are defined through the outer wall 404 of the housing 402, as well as through the upper frame 406. As will be described in more detail below, in various implementations the indication windows 432 may provide a user with the ability to view one or more components (and/or conditions thereof) of an installed cartridge. It will be appreciated, however, that the illustrated indication windows 432 are provided by way of example and not by way of limitation. For example, alternative implementations may include an indication window 432 having a different shape than that illustrated. As another example, some implementations may include only a single indication window 432 or may omit the indication windows 432 altogether. In the depicted implementation, the upper frame 406 and the housing 402 represent different parts; however, in other implementations, the upper frame and the housing may be continuously formed such that they comprise the same part.

In the depicted implementation, the housing 402 comprises a metal material, such as, for example, aluminum; however, in other implementations the housing may comprise a metal alloy material, and in still other implementations the housing may comprise a molded polymer material. In the depicted implementation, one or more of the upper frame 406, lower frame 412, and end cap 424 may be made of a molded polymer material, such as, for example, a molded plastic material (e.g., polybutylene terephthalate (PBT), acrylonitrile butadiene styrene (ABS), polyethylene, polycarbonate, Polyamide (Nylon), high impact polystyrene, polypropylene, and combinations thereof). In other implementations, one or more of these components may be made of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

In the depicted implementation, the lower frame 412 is configured to contain the battery 416 in an interior area thereof. In the depicted implementation, the battery may comprise a lithium polymer (LiPo) battery; however various other batteries may be suitable. Some other examples of batteries that can be used according to the disclosure are described in U.S. Pat. App. Pub. No. 2010/0028766 to Peckerar et al., the disclosure of which is incorporated herein by reference in its entirety. In some implementations, other types of power sources may be utilized. For example, in various implementations a power source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (e.g., cigarette lighter receptacle, USB port, etc.), connection to a computer, such as through a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

The aerosol delivery device 400 of the depicted implementation includes a control mechanism in the form of the control component 414, which is configured, in part, to control the amount of electric power provided to the heating member of the cartridge. Although other configurations are possible, the control component 414 of the depicted implementation comprises a circuit board 434 (e.g., a printed circuit board (PCB)) that includes both rigid and flexible portions. In particular, the circuit board 434 of the depicted implementation includes a rigid central section 415 and two rigid end sections comprising a proximal end section 417 and a distal end section 419, with each of the end sections 417, 419 being connected to the central section 415 by a respective flexible connection. In such a manner, when the lower frame 412, battery 416, and circuit board 434 are assembled into the control device 400, the central section 415 of the circuit board 434 is configured to be disposed proximate a major surface of the battery 416, and the two end sections 417, 419 are configured to be disposed substantially perpendicular to the central section 415. In particular, the proximal end section 417 of the circuit board 434 is configured to extend over the top of the lower frame 412, and the distal end section 419 is configured to extend over the bottom of the lower frame 412. The lower frame 412 of the control device 400 is also configured to contain the motor housing 420, into which the vibration motor 418 is received. In various implementations, the vibration motor 418 may provide haptic feedback relating to various operations of the device.

The central section 415 of the depicted implementation also includes an indicator in the form of a light source 421. In some implementations, the light source may comprise, for example, at least one light emitting diode (LED) capable of providing one or more colors of light. In other implementations, the light source may be configured to illuminate in only one color, while in other implementations, the light source may be configured to illuminate in variety of different colors. In still other implementations, the light source may be configured to provide white light. In the depicted implementation, the light source 421 comprises an RGB (red, green, blue) LED that is configured to provide a variety of colors of light, including white light. The central section 415 of the depicted circuit board 434 also includes electrical contacts 423 that are configured to operatively connect the circuit board 434 to the vibration motor 418. Other types of electronic components, structures and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference. Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In the depicted implementation, the vent 439 is configured to be installed on the inside of the housing 402 such that it covers the aperture 425. As such, in the depicted implementation one side of the vent 439 may include a pressure sensitive adhesive. In the depicted implementation, the vent 439 comprises a breathable membrane material, such as, for example, a Gore-Tex® material; however, other suitable materials are possible. In the depicted implementation, the light source 421 is covered by the light diffuser 426, a portion of which is configured to be received by the end cap 424. In such a manner, when assembled, the light diffuser 426 is positioned in or proximate an aperture 425 defined in the outer wall 404 of the housing 402 and proximate a distal end thereof. In the depicted implementation, the aperture 425 comprises a narrow, elongate opening; however, in other implementations, the aperture may be provided in any desired shape and may be positioned at any location on the control device 400. In some implementations, the light diffuser 426 may comprise a transparent or translucent member configured to allow a user to view the light source 421 from the outside of the housing 402. In the depicted implementation, the light diffuser 426 may be made of a molded polymer material, such as, for example, a molded plastic material (e.g., poly butylene terephthalate (PBT), acrylonitrile butadiene styrene (ABS), polyethylene, polycarbonate, Polyamide (Nylon), high impact polystyrene, polypropylene, and combinations thereof), although other materials, including glass, are possible. In various implementations, further indicators (e.g., other haptic feedback components, an audio feedback component, or the like) can be included in addition to or as an alternative to the indicators included in the depicted implementation. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties.

Although other configurations are possible, the proximal end section 417 of the circuit board 434 of the depicted implementation includes a pair of conductive pins 436A, 436B, as well as a pressure sensor 440. In the depicted implementation, the conductive pins 436A, 436B comprise spring-loaded pins (e.g., electrical pogo pins) that extend through the upper frame 406 such that portions of the ends of the pins 436A, 436B extend into the cartridge receiving chamber 430) and are biased in that position due to the force of the internal springs of the conductive pins 436A, 436B. In such a manner, when a cartridge is coupled with the control device 400, the conductive pins 436A, 436B are configured to contact corresponding features of the cartridge and deflect downward (e.g., toward the lower frame 412) against the force of the springs, thus operatively connecting the installed cartridge with the control component 414 and the battery 416. In the depicted implementation, the conductive pins 436A, 436B comprise gold plated metal pins; however, other materials or combinations of materials, which may also include coatings and/or platings of electrically conductive materials, are possible. Examples of electrically conductive materials, include, but are not limited to, copper, aluminum, platinum, gold, silver, iron, steel, brass, bronze, graphite, conductive ceramic materials, and/or any combination thereof. Although other profiles are possible, the ends of the conductive pins 436A, 436B of the depicted implementation have a rounded profile such that deflection of the conductive pins 436A, 436B is facilitated when a cartridge is inserted into the cartridge receiving chamber 430. In other implementations, the conductive pins may be positioned in other locations of the cartridge receiving chamber 430, such as, for example, proximate the top of the cartridge receiving chamber 430. In other implementations, the conductive pins may be positioned at a point on the sides of the upper frame 406 between the proximal end of the outer housing 402 and the bottom wall of the upper frame 406. Further, in still other implementations the conductive pins may be positioned between a midpoint of the sidewalls and the proximal end of the outer housing 402 (i.e., in an upper half of the sidewalls). Alternatively, the conductive pins may be positioned between a midpoint of the sidewalls and the bottom wall of the inner frame wall (e.g., in a lower half of the sidewalls). Moreover, in still other implementations, the conductive pins may be present at any position of the upper frame 406.

In various implementations, the aerosol delivery device may include an airflow sensor, pressure sensor, or the like. As noted above, the control component 414 of the depicted implementation includes a pressure sensor 440, which is positioned proximate and below the cartridge receiving chamber 430. The position and function of the pressure sensor 440 of the depicted implementation will be described below; however, in other implementations an airflow or pressure sensor may be positioned anywhere within the control device 400 so as to subject to airflow and/or a pressure change that can signal a draw on the device and thus cause the battery 416 to delivery power to the heating member of a cartridge. Various configurations of a printed circuit board and a pressure sensor, for example, are described in U.S. Pat. App. Pub. No. 2015/0245658 to Worm et al., the disclosure of which is incorporated herein by reference in its entirety. In the absence of an airflow sensor, pressure sensor, or the like, an aerosol delivery device may be activated manually, such as via a pushbutton that may be located on the control device and/or the cartridge. For example, one or more pushbuttons may be used as described in U.S. Pat. App. Pub. No. 2015/0245658 to Worm et al., which is incorporated herein by reference in its entirety. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pat. App. Pub. 2016/0158782 to Henry et al., which is incorporated herein by reference in its entirety.

Although not included in the depicted implementation, some implementations may include other types of input elements, which may replace or supplement an airflow or pressure sensor. The input may be included to allow a user to control functions of the device and/or for output of information to a user. Any component or combination of components may be utilized as an input for controlling the function of the device. In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In the depicted implementation, the pressure sensor seal 410 is configured to cover the pressure sensor 440 to protect it from any liquid and/or aerosol from an installed cartridge. In such a manner, the pressure sensor seal 410 of the depicted implementation (as well as other sealing members, including the upper chassis seal 435, lower chassis seal 437, motor housing 420, and the pin seal 422) may be made of silicone rubber, boron nitride (BN) rubber, natural rubber, thermoplastic polyurethane, or another resilient material.

Although other configurations are possible, the distal end section 419 of the circuit board 434 includes the external connection element 438. In various implementations, the external connection element 438 may be configured for connecting to an external connector and/or a docking station or other power or data source. For example, in some implementations an external connector may comprise first and second connector ends that may be interconnected by a union, which may be, for example, a cord of variable length. In some implementations, the first connector end may be configured for electrical and, optionally, mechanical connection with the device, and the second connector end may be configured for connection to a computer or similar electronic device or for connection to a power source. An adaptor including a USB connector at one end and a power unit connector at an opposing end is disclosed in U.S. Pat. App. Pub. No. 2014/0261495 to Novak et al., which is incorporated herein by reference in its entirety. In the depicted implementation, the pin seal 422 is configured to seal the interface between the external connection element 438 and the end cap 424. In the depicted implementation, one or more pins of the external connection element 438 may extend through the end cap 424 of the control device as noted above. In the depicted implementation, the end cap 424 also includes a pair of end cap pins 441A, 441B that may be affixed to the end cap 424. For example, in some implementations, the end cap pins 441A, 441B may be insert-molded into the end cap 424. In some implementations, a bottom surface of the end cap pins 441A, 441B (which, in some implementations, may be flat) may be configured to provide attraction for magnets contained in an external charger assembly. In such a manner, the end cap pins 441A, 441B may be made of any material configured to be attracted by a magnet, such as various ferromagnetic materials, including, but not limited to, steel, iron, nickel, cobalt, other alloys, and/or any combination thereof. A detailed view of the end cap assembly is shown in FIG. 16.

Referring back to FIG. 15, the upper frame 406 includes a pair of magnets 446A, 446B that are exposed in the cartridge receiving chamber 430. In various implementations, the magnets 446A, 446B may comprise any type of magnets, including rare earth magnets. For example, in some implementations, one or more of the magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more of the magnets may comprise Samarium Cobalt magnets (also known as SmCo magnets). In still other implementations, one or more of the magnets may comprise Ceramic/Ferrite magnets. In other implementations, one or more of the magnets may comprise Aluminum-Nickel-Cobalt (AlNiCo) magnets. In any of the foregoing implementations, one or more of the magnets may be plated and/or coated. For example, in some implementations, one or more of the magnets may be coated with nickel. In other implementations, one or more magnets may be coated with one or more of zinc, tin, copper, epoxy, silver and/or gold. In some implementations, one or more of the magnets may be coated with combinations of these materials. For example, in one implementation, one or more of the magnets may be coated with nickel, copper, and nickel again. In another implementation, one or more of the magnets may be coated with nickel, copper, nickel, and a top coating of gold.

FIG. 16 illustrates a perspective view of an end cap assembly, according to an example implementation of the present disclosure. In particular, FIG. 16 illustrates a perspective view of the end cap 424, light diffuser 426, and end cap pins 441A, 441B. As shown in the figure, the end cap 424 also includes a seal groove 442, which extends around a distal periphery of the end cap 424. Referring back to FIG. 15, the seal groove 442 of the end cap 424 is configured to receive an end cap seal 443 that provides a sealing interface between the end cap 424 and the housing 402, and in particular, an inner surface of the outer wall 404. In various implementations, the end cap seal 443 may be made of silicone rubber, boron nitride (BN) rubber, natural rubber, thermoplastic polyurethane, or another resilient material. As also shown in FIG. 15, in various implementations the upper portions of the end cap pins 441A, 441B are configured to engage with the lower frame 412. For example, in the depicted implementation the upper portions of the end cap pins 441A, 441B are configured to create an interference or press-fit engagement with corresponding slotted openings in the lower frame 412. In various implementations, the interface between the end cap 424 and the housing 402 (e.g., via the interface between the end cap seal 443 and the inner surface of the outer housing wall 404 and/or the upper portions of the end cap pins 441A, 441B and the lower frame 412) may create a press-fit engagement with the housing 402 that is configured to be releasable so that the end cap 424 (or end cap assembly) may be removable.

In various implementations, the control device may include one or more components configured to meet battery outgassing requirements under UL 8139. For example, the control device may include an end cap configured to eject in the event that sudden pressurization occurs within the control device enclosure. In one implementation, the end cap may include retaining pins that extend substantially perpendicularly from a wall of the end cap. The retaining pins may be configured to mate with receiving features (e.g., holes) in a frame of the control device to establish a friction fit or press fit that may be overcome if an internal pressure within the control device housing exceeds a defined internal pressure.

FIGS. 17A-17C illustrate several subassemblies that together comprise the control device 400. In particular, FIG. 17A illustrates a lower inner subassembly 447 and an upper inner subassembly 445, FIG. 17B illustrates an inner subassembly 451 and a housing subassembly 449, and FIG. 17C illustrates a main subassembly 453 and an end cap subassembly 455. In the depicted implementation, the upper inner subassembly 445 is assembled by applying glue to receiving pockets of the upper frame 406 and press-fitting the magnets 446A, 446B into the upper frame 406. In addition, the sensor seal 410 is pressed into a receiving pocket of the upper frame 406, and the upper chassis seal 435 is stretched over a receiving groove of the upper frame 406. In the depicted implementation, the lower inner subassembly 447 is assembled by soldering the battery 416 to the circuit board 434 (in the depicted implementation, the vibration motor 418 is pre-soldered to the circuit board 434). The circuit board 434 is then coupled with the battery 416 using the front foam pad 431, which may have adhesive material on both sides thereof. The motor housing 420 may then be pressed onto the vibration motor 418, such as via an interference fit. The circuit board 434 with the attached components may then be inserted into the lower frame 412, with the back foam pad 433 located in between (adhesive may be present on one or both sides of the back foam pad 433 to aid in assembly). As illustrated in FIG. 17A, the lower inner subassembly 447 and the upper inner subassembly 445 may then be assembled together via one or more snap features that may be included on the upper inner subassembly 445 and/or the lower inner subassembly 447. As illustrated in FIG. 17B, the inner subassembly 451, comprised of the lower inner subassembly 447 and the upper inner subassembly 445, may then be inserted into the housing subassembly 449, which is assembled by adhering the vent 439 on the inside of the housing 406 proximate the aperture 425 thereof. In some implementations, adhesive may be used to secure the parts together (such as, for example, by applying adhesive through one or more holes in the lower frame 412).

FIGS. 18-20 illustrate a cartridge 500, a portion which is configured to be coupled with the cartridge receiving chamber 430 of the inner frame 406 of the control device 400) such that mechanical and electrical connections are created between the cartridge 400 and the control device 400. In particular, when the cartridge 400 of the depicted implementation is coupled with the upper frame 406 of the control device 400, a magnetic connection is created between the magnets 446A, 446B located in the upper frame 406 and corresponding features of the cartridge 500. In addition, when the cartridge 500 of the depicted implementation is coupled with the inner frame 406, an electrical connection is created between the pair conductive pins 436A, 436B of the control device 400 and corresponding features of the cartridge 500. As such, when the cartridge 500 is received in the upper frame 430 of the control device 400, the cartridge 500 may be operatively connected to the control component 414 and the battery 416 of the control device 400. Thus, when the cartridge 500 of the depicted implementation is coupled with the control device 400, the cartridge 500 is mechanically biased into connection with the control device 400 such that electrical connection is maintained between the cartridge and the control device.

In particular, FIG. 18 illustrates a perspective view of a cartridge 500, according to another example implementation of the present disclosure, FIG. 19 illustrates an exploded perspective view of the cartridge 500, and FIG. 20 illustrates a side section view of the cartridge 500. Although other configurations are possible, the cartridge 500 of the depicted implementation generally includes a mouthpiece 502, a mouthpiece insert 504, an upper aerosol channel insert 506, an upper cartridge seal 508, a tank 510 that defines a tank wall 511, a lower cartridge seal 512, a base member 514, a liquid transport element (e.g., a wick) 516, a heating member 518, a pair of heater connectors 520A, 520B, a pair of metal inserts 524A, 524B, and a bottom cap 526.

As shown in the figures, the mouthpiece 502 of the depicted implementation defines a proximal end and a distal end, with the proximal end of the mouthpiece 502 defining an exit portal 515 therein. In the depicted implementation, the mouthpiece insert 504 is configured to be located proximate the proximal end of the mouthpiece 502 such that it extends through the exit portal 515 thereof. In the depicted implementation, the mouthpiece 502 and the mouthpiece insert 504 may be made of a molded polymer material, such as, for example, a molded plastic material (e.g., polypropylene, acrylonitrile butadiene styrene (ABS), polyethylene, polycarbonate, Polyamide (Nylon), high impact polystyrene, and combinations thereof), although other materials are possible. The mouthpiece insert 504 of the depicted implementation includes a flange feature on a lower portion thereof such that the mouthpiece insert 504 may be installed from inside the mouthpiece 502 and may be configured for a press or snap-fit connection with the exit portal 515. In other implementations, other attachment methods are possible (e.g., via adhesives, heat staking/welding, ultrasonic welding, etc.). In still other implementations, the mouthpiece and mouthpiece insert may be constructed using an insert molding or overmolding process such that the mouthpiece 502 and the mouthpiece insert 504 comprise a unitary part. The mouthpiece 502 of the depicted implementation is configured to be secured to the tank 510 via snap features. For example, the mouthpiece 502 of the depicted implementation includes a ridge feature 543 (see FIG. 20) that extends around at least a portion of an inner surface thereof, and the tank 510 includes a corresponding groove feature 541 that extends around at least a portion of an outer surface thereof. In other implementations, these features may be reversed (e.g., the mouthpiece may include a groove and the tank may include a ridge feature). In still other implementations, other attachment methods are possible (e.g., via adhesives, heat staking/welding, ultrasonic welding, etc.).

In some implementations, the mouthpiece insert may exhibit a color associated with a distinctive characteristic of the cartridge. For example, in some implementations a cartridge of the present disclosure may include a liquid composition that includes a distinctive characteristic such as, for example, a particular flavorant (as discussed infra), or a specific strength of nicotine, although any characteristic of the cartridge may be considered a distinctive characteristic. For the purposes of the current description, the term "color" should be interpreted broadly, for example covering any color or any shade of the same color. It should also be noted that in some implementations, certain colors may be commonly associated with particular distinctive characteristics (e.g., the color green may be associated with a mint flavorant, and the color red may be associated with an apple flavorant); however, in other implementations, certain colors may be associated with particular distinctive characteristics according to an index or guide, which may be provided or made available to a user. Examples of distinctive characteristics are described in U.S. patent application Ser. No. 16/171,920, titled Aerosol Delivery Device with Flavor Indicator, which is incorporated herein by reference in its entirety.

The tank 510 of the depicted implementation defines a proximal end and a distal end, wherein the mouthpiece 502 is configured to engage the proximal end of the tank 510 and the bottom cap 526 is configured to engage the distal end of the tank 510. In the depicted implementation, the tank 510 also defines a reservoir cavity 528 that includes a closed proximal end and an open distal end. As such, the reservoir cavity 528 of the tank 510 is configured to contain a liquid composition (e.g., an e-liquid or aerosol precursor composition) therein. The closed proximal end of the reservoir cavity 528 allows the cavity to create a reliable seal on the top side of the liquid composition column. This may prevent the seepage/entry of air into the reservoir cavity from the top end when the cartridge is held upright. This may also prevent air from entering from the top of the liquid composition column, which may create a vacuum and may reduce the potential of the liquid composition to leak from the bottom of the tank through the liquid transport element or other passages.

Although other configurations are possible, in the depicted implementation a pair of internal aerosol flow tubes are defined on opposite sides of the reservoir cavity 528 of the tank 510. In the case of an injection molded tank 510, the internal aerosol flow tubes are configured to be molded therein. As will be described in more detail below, aerosol produced in a vaporization chamber of the cartridge 500 is configured to travel through the aerosol flow tubes for delivery to a user.

In the depicted implementation, the tank wall 511 is configured to be transparent or translucent so that the liquid composition contained therein may be visible externally. As such, in the depicted implementation the entire tank wall 511 is configured to be transparent or translucent. Alternatively, in some implementations, only a portion of the tank wall or only a single side of the tank wall may be transparent or translucent while the remaining portions of the tank wall may be substantially opaque. In other implementations, the tank wall may be substantially opaque, and a strip extending from the proximal end of the tank to the distal end of the tank may be transparent or translucent. In further implementations, the tank wall may be colored. In some implementations, the color can be configured so that the liquid composition within the tank is still visible, such by using a transparent or translucent outer tank wall. In other implementations, the tank wall can be configured so that the outer tank wall has substantially opaque color. In the depicted implementation, the tank 510 may be made of a molded polymer material, such as, for example, a molded plastic material (e.g., a copolyester material, such as, for example, Tritan™ copolyester), acrylonitrile butadiene styrene (ABS), polyethylene, polycarbonate, Polyamide (Nylon), high impact polystyrene, polypropylene, and combinations thereof), although other materials, including glass, are possible.

In some implementations, the indication window 432 of the control device 400 may be configured so that at least a portion of the tank 510 and at least a portion of the bottom cap 526 are visible when the cartridge 500 is engaged with the control device 400. As noted above, in some implementations at least a portion of the tank wall 511 may be configured to be at least partially transparent or translucent so that the liquid composition contained therein is visible externally. Thus, the relative amount of any liquid composition present in the tank 510 may be visible through the indication window when the cartridge 500 is engaged with the control device 400. As illustrated in FIGS. 14 and 15, the indication window 432 of the depicted implementation is located near the proximal end of the control device 400 and is configured as an elongate oval shaped cut-out in the outer wall 404 of the housing 402 and the upper frame 406 of the control device 400. It should be understood that in other implementations, the indication window my have any other shapes and/or locations. For example, in some implementations the indication window may be configured as a notch extending from the proximal end of the outer wall of the control device a distance toward the distal end of the device. In still other implementations, the indication window may be configured so as not to have any open borders and thus may expressly exclude a notch configuration as noted above. In some implementations, the indication window may be completely open, and in other implementations, the indication window may have a transparent member (e.g., glass or plastic) positioned in the opening defined by the indication window or covering the indication window on one or both of the inner surface and outer surface of the outer wall of the control device. It should be understood that in some implementations, the indication window may be formed in part by the cartridge and in part by the control device. For example, in some implementations, the cartridge may include a portion of the indication window (e.g., a top portion of an indication window), and the control device may include a separate portion of the indication window (e.g., a bottom portion of the indication window). In some implementations, the indication window may be located in the cartridge rather than, or in addition to, an indication window located in the control device. For example, in one implementation the mouthpiece and/or another cartridge component may act as a sleeve covering a transparent wall of the cartridge. The sleeve may include an indication window, which may be positioned mostly or entirely above a power unit chamber when the cartridge is inserted into the control device. As noted, other implementations may not include any indication windows.

Although other configurations are possible, in the depicted implementation the proximal end of the tank 510 is configured to receive the upper cartridge seal 508, which is configured to form a substantially air tight and liquid tight seal between the tank 510 and the mouthpiece 502. As such, the upper cartridge seal 508 may be made of silicone rubber, boron nitride (BN) rubber, natural rubber, thermoplastic polyurethane, or another resilient material. In the depicted implementation, the upper cartridge seal 508 is also configured to receive and seal the upper aerosol channel insert 506 (see also FIG. 20).

For aerosol delivery systems that are characterized as electronic cigarettes, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

In the depicted implementation, the liquid composition, sometime referred to as an aerosol precursor composition or a vapor precursor composition or "e-liquid", may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In the depicted implementation, the reservoir cavity 528 is configured to hold approximately 1.5 mL of aerosol precursor composition. In other embodiments, the reservoir cavity 528 is configured to hold about 1 ml or more, about 2 ml or more, about 5 ml or more, or about 10 ml or more of the aerosol precursor composition.

In some implementations, the liquid composition may include one or more flavorants. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honey bush, rooibos, verba santa, bacopa monniera, *gingko biloba*, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be understood that reference to a flavorant should not be limited to any single flavorant as described above, and may, in fact, represent a combination of one or more flavorants.

As shown in the figures, the cartridge 500 of the depicted implementation also includes a base member 514, which is configured to engage and cover the open distal end of the reservoir cavity 528 of the tank 510. The lower seal 512 of the depicted implementation is configured form a substantially air tight and liquid tight seal between a lower portion of the tank 510 and the bottom cap 526 (see also FIG. 20), in particular, the lower seal 512 is configured to be located within a groove on an outer surface of the base member 514 so as to facilitate a substantially air tight and liquid tight seal between the base member 514 and tank 510. In various implementations, the lower seal 512 may be made of silicone rubber, boron nitride (BN) rubber, natural rubber, thermoplastic polyurethane, or another resilient material. In the depicted implementation, the base member 514 may be made of a molded polymer material, such as, for example, a molded plastic material (e.g., a copolyester material, such as, for example. Tritan™ copolyester, acrylonitrile butadiene styrene (ABS), polyethylene, polycarbonate. Polyamide (Nylon), high impact polystyrene, polypropylene, and combinations thereof), although other materials are possible. The base member 514 of the depicted implementation also includes a plurality of slots (see also FIG. 17) that are configured to provide liquid flow passages for the liquid composition contained in the reservoir cavity 528 of the tank 510 in order to facilitate transfer of the liquid to the liquid transport element 516. In some implementations, the slots may also provide retention of some liquid even when the bulk liquid composition in the reservoir cavity 528 is not in contact with the base member 514 (such as, for example, when the aerosol delivery device is upside down).

As shown in the figures, the liquid transport element 516 is disposed within the base member 514 and extends between the liquid composition in the reservoir cavity 528 and the heating member 518 (see also FIG. 20). In the depicted implementation, the liquid transport element 516 is formed of a cotton material and, when installed in the cartridge 500, has a curved shape. In other implementations, however, the liquid transport element 516 may have other shapes and may be formed of a variety of materials configured for transport of a liquid, such as by capillary action. For example, in some implementations the liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In other implementations, the liquid transport element may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference in their entireties.

As shown in the figures, the heating member 518 of the depicted implementation is also configured to be disposed within the base member 514. In particular, the heating member 518 of the depicted implementation comprises a heating element that has a substantially flat profile. While in some implementations the heating member may maintain a substantially flat profile when installed in a cartridge, when the heating member 518 of the depicted implementation is installed in the cartridge 500 it has a curved or bowed shape corresponding to the curved shape of the liquid transport element 516 (see also FIG. 20). In such a manner, the heating member 518 in the installed position contacts a bottom surface of the liquid transport element 516. In the depicted implementation, the curved form of the flat heating member 518 may provide a large ratio of cross-sectional flow area to flow path length through the liquid transport element 516. This may provide increased performance with respect to delivery of the liquid composition to the liquid transport element 516. When installed, edges of the heating member 518 are configured to engage the base member 514 such that the heating member 518 maintains its curved shape. In such a manner, the curvature of the heating member 518 may also provide a compressive force against the liquid transport element 516. In addition, the spring recover force of the heating member 518 allows the edges of the heating member 518 to locate or lock into the base member 514, which may reduce or eliminate any need for additional features configured to hold the heating member 518 in the base member 514 from the other side. The installed curvature of the heating member 518 may also bias deflection of the heating member 518 that may occur with thermal expansion towards the liquid transport element 516, thus helping to maintain thermal contact between the heating member 518 and the liquid transport element 516. In the depicted implementation, the liquid transport element 516 and the heating member 518 comprise a heating assembly 534, which, together with the base member 514 and the bottom cap 526, define a vaporization chamber 532.

It should be noted that some implementations need not include a heating assembly, but, rather, may include an atomization assembly configured to generate an aerosol in another manner. Some examples of atomization assemblies that generate aerosols in other ways can be found, for example, in U.S. application Ser. No. 16/544,326, filed on Aug. 19, 2019, and titled Detachable Atomization Assembly for Aerosol Delivery Device, which is incorporated herein by reference in its entirety.

In the depicted implementation, the heating member 518 may be made of a metal material, such as a stainless steel material, including, but not limited to, 316L, 316, 304, or 304L stainless steel. In other implementations, the heating member may be made of a different material, such as, for example, Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. Other heaters are described in U.S. Pat. App. Pub. No. 2016/0345633 to DePiano et al., which is incorporated herein by reference in its entirety.

Although in other implementations additional and/or differing contact features may be provided, the heating member 518 of the depicted implementation includes a pair of contact holes 531A, 531B that are configured to connect the heating member 518 to the heater connectors 520A, 520B of the cartridge 500. In depicted implementation, the heater connectors 520A, 520B are made of a conductive material and are plated with nickel and/or gold. Examples of conductive materials include, but are not limited to, copper, aluminum, platinum, gold, silver, iron, steel, brass, bronze, graphite, conductive ceramic materials, and/or any combination thereof. In the depicted implementation, the contact holes 531A, 531B are configured to have an inner diameter that is less than an outer diameter of the mating portions of the heater connectors 520A, 520B. In some implementations, the contact holes may include one or more features (e.g., one or more fingers or extensions) that create an effective inner diameter that is less than an outer diameter of the mating portion of the heater connectors 520A, 520B. In such a manner, the contact holes 531A, 531B of the heating member 518 may create an interference fit with the upper ends of the heater connectors 520A, 520B such that the heating member 518 may maintain electrical contact with the heater connectors 520A, 520B. In the depicted implementation, the heater connectors 520A, 520B are insert-molded into the bottom cap 526.

The bottom cap 526 of the depicted implementation is configured to be secured to the distal end of the tank 510 via an ultrasonic welding process; however, other attachment methods are possible (e.g., via adhesives, heat staking/welding, snap-fit, etc.). In the depicted implementation, the bottom cap 526 of the cartridge 500 includes a cartridge air inlet channel 530, which is located in an approximate center of a bottom surface of the bottom cap 526. Although other configurations are possible, in the depicted implementation the cartridge air inlet channel 530) has a nozzle-like shape. In particular, the cartridge air inlet channel 530 of the depicted implementation includes a first portion (proximate the bottom surface of the bottom cap 526), which has a substantially cylindrical shape and a second portion, which has a substantially conical shape and leads to the vaporization chamber 532. In such a manner, the internal diameter of the cartridge air inlet channel 530 decreases before leading to the vaporization chamber 532. This configuration may help to keep the air inlet channel 530 relatively clear of liquid build-up leading into the vaporization chamber 532.

Although other configurations are possible, the cartridge 500 of the depicted implementation also includes a pair of metal inserts 524A, 524B that are positioned in the bottom cap 526 and are configured to be exposed through the bottom surface thereof. In the depicted implementation, the metal inserts 524A, 524B are insert-molded into the bottom cap 526. In some implementations, the metal inserts 524A, 524B may be configured for a press or snap fit connection with the bottom cap 526. In the depicted implementation, the metal inserts 524A, 524B are made of stainless steel plated with nickel; however, in other implementations the metal inserts may be made of any material configured to be attracted by a magnet, such as various ferromagnetic materials, including, but not limited, to iron, nickel, cobalt, alloys such as steel, and/or any combination thereof.

As noted above, when the cartridge 500 is coupled with the cartridge receiving chamber 430 of the control device 400, mechanical and electrical connections are created between the cartridge 500 and the control device 400. In particular, when the cartridge 500 of the depicted implementation is coupled with the upper frame 406 of the control device 400, a magnetic connection is created between the magnets 446A, 446B located in the upper frame 406 and the metal inserts 524A, 524B located in the bottom cap 526 of the cartridge 500. In addition, when the cartridge 500 of the depicted implementation is coupled with the inner frame 406, an electrical connection is created between the pair of conductive pins 436A, 436B of the control device 400 and the heater connectors 520A, 520B of the cartridge 500. Thus, when the cartridge 500 of the depicted implementation is coupled with the control device 400, the cartridge 500 is mechanically biased into connection with the control device 400 such that electrical connection is maintained between the cartridge 500 (and, in particular the heating assembly 534) and the control device (and in particular, the control component 414 and the battery 416).

When the cartridge 500 of the depicted implementation is coupled with the control device 400, the electrical connection between the control device 400 and the heating member 518 of the cartridge 500) (via the conductive pins 436A, 436B of the control device 400) and the heater connectors 520A, 520B of the cartridge) allows the control body 400 to direct electrical current to the heating member 518. In the depicted implementation, this may occur when a puff on the aerosol delivery device is detected (or, in other implementations, via actuation by the user, such as, for example, via a pushbutton). When a user of the aerosol device of the depicted implementation draws on the mouthpiece 502, inlet airflow is directed into the device via a gap between the cartridge 500 and the control device 400. In the depicted implementation, the gap comprises a peripheral gap that extends around substantially the entire periphery of the cartridge 500. It should be understood that in other implementations, the gap need not extend around the entire periphery of the cartridge, for example in some implementations the gap may comprise one or more gaps that extend around a portion of the periphery of the cartridge rather than the entire periphery, and in some implementations, the gap may comprise one or more individual holes. In the depicted implementation, the gap originates at an interface between an outside surface of the cartridge 500 and an inside surface of the control device 400. In particular, the gap originates at the interface of an outer surface of the mouthpiece 502 of the cartridge 500 and a top edge of the outer wall 404 of the housing 402 of the control device 400.

In the depicted implementation, the gap between the cartridge 500 and the control device 400 is established and maintained by features of the cartridge 500 and the control device 400. Although other configurations are possible, the upper frame 406 of the depicted implementation includes a plurality of protuberances that are spaced around an inner surface of the upper frame 406 and that are configured to laterally position the cartridge 400. In the depicted implementation, the plurality of protuberances comprise a plurality of raised elongate bosses that extend from an approximate top of the upper frame 406 to a recessed surface thereof. When the cartridge 500 of the depicted implementation is coupled with the control device 400, the plurality of protuberances of the upper frame 406 contact an outer surface of the cartridge 500) (and in particular, an outer surface of the mouthpiece 502 and/or an outer surface of the tank 510 and/or an outer surface of the bottom cap 526). In such a manner, the protuberances position the cartridge 500 laterally with respect to the upper frame 406, thus establishing and maintaining the gap. It should be understood that in other implementations, the protuberances may take other forms (including, for example, one or more bumps), and may be located on one or more components of the cartridge rather than (or in addition to) the control device.

As a user draws on the device, the air that enters the gap between the cartridge 500 and the control device 400 travels downward around the outside of the cartridge 500 and below the bottom cap 526 thereof. In the depicted implementation, inlet air is permitted to travel below the bottom cap 526 due to the vertical position of the cartridge 500 with respect to the bottom of the cartridge receiving chamber 430. In particular, the vertical position of the cartridge 500 of the depicted implementation is established using one or more of location features that extend upward from the recessed surface of the upper frame 406, at least one of which is configured to contact the bottom surface of the bottom cap 526 when the cartridge 500 is coupled with the control device 400. In such a manner, when the cartridge 500 is received into the control device 400, the gap between the cartridge 500 and the control device 400 is also established between the bottom of the bottom cap 526 and the recessed surface of the upper frame 406.

As noted above, although other configurations are possible, the bottom cap 526 of the depicted implementation includes an inlet channel 530 that is located in an approximate center of the bottom surface of the bottom cap 526. Because of the gap established between the bottom of the bottom cap 526 and the recessed surface of the upper frame 406, inlet air that travels around the outside of the cartridge 500 and below the bottom cap 526 enters the cartridge 500) through the inlet channel 530 of the bottom cap 526. The air that enters through the inlet channel 530 then enters the vaporization chamber 532 of the cartridge. As the air is drawn through the inlet channel 530 into the cartridge 500, the pressure sensor 440) of the control device 400 detects the draw. When a draw is detected by the pressure sensor 440), the control component 414 directs current through the heating member 518 in order to heat the heating member 518. As the heating member 518 heats, at least a portion of the liquid composition contained in the liquid transport element 516 is vaporized in the vaporization chamber 532. Accordingly, aerosol produced in the vaporization chamber 532 may then directed to the user. In particular, as the air enters the cartridge 500 via the air inlet channel 530, the air travels through the vaporization chamber 532 where it mixes with the vaporized liquid composition and becomes the aerosol. Due to the geometry of the vaporization chamber 532 and the bottom cap 526, the aerosol is split into two separate paths that extend through the inside of the bottom cap 526 and then through aerosol flow tubes that are defined on opposite sides of the reservoir cavity 528 of the tank 510. This relatively tortuous configuration may increase the effective flow path length and area for heat sinking, thus providing increased cooling of the aerosol stream prior to reaching the user. The two aerosol paths converge at the proximal end of the tank 510 and below the upper aerosol channel insert 506. The recombined aerosol then flows through the upper aerosol channel insert 506 and out of the exit portal 515 of the mouthpiece 500, to the user. It should be understood that the aerosol passages downstream from the air inlet channel 530 inlet are configured to be oversized, in order to minimize any additional system pressure drop created by these passages.

Although other configurations are possible, in the depicted implementation, the upper aerosol channel insert 506 is configured to absorb liquid formed by deposition and/or condensation from aerosol formed in the vaporization chamber 532, and is configured to have rigid or semi-rigid properties. As such, the upper aerosol channel insert 506 of the depicted implementation may be made of a fibrous, sintered beaded, or open cell foam material. For example, in some implementations, the upper aerosol channel insert may be made of a fibrous bonded polyethylene (PE) or polyethylene terephthalate (PET) material. In such a manner, the upper aerosol channel insert 506 may be configured for a press or snap fit attachment with the mouthpiece 502. The upper aerosol channel insert 506 is also configured to help to prevent accumulation of liquid from exiting the cartridge 500 through the mouthpiece 502. In addition, the upper aerosol channel insert 506 is located in such a way that aerosol produced in the vaporization chamber 532 passes through the insert 506 just prior to exiting the cartridge 500. In the depicted implementation, the inside cavity of the upper aerosol channel insert 506 may also serve as a cooling chamber within which the formed aerosol can be allowed to expand and/or cool before passing through the exit portal 515. In some implementations, the vaporization chamber 532 and the cooling chamber may be configured to have a defined relative volume ratio.

FIGS. 21A and 21B illustrate subassemblies of the cartridge of FIG. 18, according to example implementations of the present disclosure. In particular, FIG. 21A illustrates a bottom cap subassembly 545 and a tank subassembly 547, and FIG. 21B illustrates a lower subassembly 551 and a mouthpiece subassembly 549. In the depicted implementation, the bottom cap subassembly 545 comprises the bottom cap 526, the metal inserts 524A, 524B, the heater connectors 520A, 520B, the heating member 518, the liquid transport element 516, the base member 514, and the lower cartridge seal 512. In the depicted implementation, the metal inserts 524A, 524B and the heater connectors 520A, 520B are insert-molded into the bottom cap 526. In addition, the lower cartridge seal 512 is stretched around the base member 514 such that it is positioned in the groove thereof. The liquid transport element 516 is inserted into the base member 514 and the heating member is press-fit into the base member 514 such that the contact holes 531A, 531B press around respective portions of the heater connectors 520A, 520B and the heating member 518 bends into a curved shape, therein also trapping and bending the liquid transport element 516 into a curved shape. The tank subassembly 547 of the depicted implementation comprises the tank 510 into which the liquid composition has been filled via the open end of the tank 510.

In the depicted implementation, the lower subassembly 551 of FIG. 21B is assembled by joining the bottom cap subassembly 545 to the tank subassembly 547. In particular, the bottom cap subassembly 545 of the depicted implementation is joined to the tank subassembly 547 via a substantially continuous ultrasonic weld. In the depicted implementation, the mouthpiece subassembly 549 comprises the mouthpiece 502, the mouthpiece insert 504, the aerosol channel insert 506, and the cartridge seal 508. The mouth-piece subassembly 549 of the depicted implementation is assembled by pressing the mouthpiece insert 504 into the mouthpiece 502, pressing the cartridge seal 508 into the mouthpiece 502, and pressing the aerosol channel insert 506 into the cartridge seal 508. In the depicted implementation, the final assembly of the cartridge 500 occurs by snapping the mouthpiece subassembly 549 onto the lower subassembly 551 via the groove feature 541 of the outer surface of the tank 510 and the ridge feature of the inner surface of the mouthpiece 502.

FIG. 22 illustrates an exploded perspective view of a control device of an aerosol delivery device, according to another example implementation of the present disclosure. As shown in the figure, the control device 600 of the depicted implementation generally includes a housing 602 defining an outer wall 604, an upper frame 606, an upper frame seal 608, a pressure sensor seal 610, a lower frame 612, a control component 614, a battery 616, a vibration motor 618, a motor housing 620, a pin seal 622, an end cap 624, a light diffuser 626, and a vent 645. The control device 600 of the depicted implementation also includes a front foam pad 631, a plurality of side foam pads 637, and an insulator 639. In the depicted implementation, the front foam pad 631 is configured to be disposed between the battery 616 and the control component 614, and the side foam pads 437 are configured to be disposed on opposite sides of the battery 616. In some implementations, the control device may include one or more other seals, which may include, for example, an upper chassis seal and/or a lower chassis seal.

The arrangement of the components of the control device 600 is illustrated in FIG. 23, which depicts a section view of the control device, according to an example implementation of the present disclosure. In particular, FIG. 23 illustrates a front section view of the control device 600. As illustrated in the figure, the upper frame 606 of the control device 600 defines a cartridge receiving chamber 630 within which a cartridge may be coupled. The control device 600 also includes a pair of opposite indication windows 632 that are defined through the outer wall 404 of the housing 602, as well as through the upper frame 606. It should be noted, however, that is some implementations there need not be any indication windows. For implementations that include indication windows, such indication windows may provide a user with the ability to view one or more components (and/or conditions thereof) of an installed cartridge. It will be appreciated, however, that the illustrated indication windows 632 are provided by way of example and not by way of limitation. For example, alternative implementations may include an indication window having a different shape than that illustrated. As another example, some implementations may include only a single indication window. In the depicted implementation, the upper frame 606 and the housing 602 represent different parts; however, in other implementations, the upper frame and the housing may be continuously formed such that they comprise the same part.

In the depicted implementation, the housing 602 comprises a metal material, such as, for example, aluminum; however, in other implementations the housing may comprise a metal alloy material, and in still other implementations the housing may comprise a molded polymer material. In the depicted implementation, one or more of the upper frame 606, lower frame 612, and end cap 624 may be made of a molded polymer material, such as, for example, a molded plastic material (e.g., polybutylene terephthalate (PBT), acrylonitrile butadiene styrene (ABS), polyethylene, polycarbonate, Polyamide (Nylon), high impact polystyrene, polypropylene, and combinations thereof). In other implementations, one or more of these components may be made of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

In the depicted implementation, the lower frame 612 is configured to contain the battery 616 in an interior area thereof. In the depicted implementation, the battery may comprise a lithium polymer (LiPo) battery; however various other batteries may be suitable. Some other examples of batteries that can be used according to the disclosure are described in U.S. Pat. App. Pub. No. 2010/0028766 to Peckerar et al., the disclosure of which is incorporated herein by reference in its entirety. In some implementations, other types of power sources may be utilized. For example, in various implementations a power source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (e.g., cigarette lighter receptacle, USB port, etc.), connection to a computer, such as through a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

The control device 600 of the depicted implementation includes a control mechanism in the form of the control component 614, which is configured, in part, to control the amount of electric power provided to the heating member of the cartridge. Although other configurations are possible, the control component 614 of the depicted implementation comprises a circuit board 634 (e.g., a printed circuit board (PCB)) that includes both rigid and flexible portions. In particular, the circuit board 634 of the depicted implementation includes a rigid central section 615 and two rigid end sections comprising a proximal end section 617 and a distal end section 619, with each of the end sections 617, 619 being connected to the central section 615 by a respective flexible connection. In such a manner, when the lower frame 612, battery 616, and circuit board 634 are assembled into the control device 600, the central section 615 of the circuit board 634 is configured to be disposed proximate a major surface of the battery 616, and the two end sections 617, 619 are configured to be disposed substantially perpendicular to the central section 615. In particular, the proximal end section 617 of the circuit board 634 is configured to extend over the top of the lower frame 612, and the distal end section 619 is configured to extend over the bottom of the lower frame 612. The lower frame 612 of the control device 600 is also configured to contain the motor housing 620, into which the vibration motor 618 is received. In various implementations, the vibration motor 618 may provide haptic feedback relating to various operations of the device.

The central section 615 of the depicted implementation also includes an indicator in the form of a light source 621. In some implementations, the light source may comprise, for example, at least one light emitting diode (LED) capable of providing one or more colors of light. In other implementations, the light source may be configured to illuminate in only one color, while in other implementations, the light source may be configured to illuminate in variety of different colors. In still other implementations, the light source may be configured to provide white light. In the depicted implementation, the light source 621 comprises an RGB (red, green, blue) LED that is configured to provide a variety of colors of light, including white light. The central section 615 of the depicted circuit board 634 also includes electrical contacts 623 that are configured to operatively connect the circuit board 634 to the vibration motor 618. Other types of electronic components, structures and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference. Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In the depicted implementation, the vent 645 is configured to be installed on the inside of the housing 602 such that it covers the aperture 625. As such, in the depicted implementation one side of the vent 645 may include a pressure sensitive adhesive. In the depicted implementation, the vent 645 comprises a breathable membrane material, such as, for example, a Gore-Tex® material; however, other suitable materials are possible. In the depicted implementation, the light source 621 is covered by the light diffuser 626, a portion of which is configured to be received by the end cap 624. In such a manner, when assembled, the light diffuser

626 is positioned in or proximate an aperture 625 defined in the outer wall 604 of the housing 602 and proximate a distal end thereof. In the depicted implementation, the aperture 625 comprises a narrow, elongate opening; however, in other implementations, the aperture may be provided in any desired shape and may be positioned at any location on the control device 600. In some implementations, the light diffuser 626 may comprise a transparent or translucent member configured to allow a user to view the light source 621 from the outside of the housing 602. In the depicted implementation, the light diffuser 626 may be made of a molded polymer material, such as, for example, a molded plastic material (e.g., poly butylene terephthalate (PBT), acrylonitrile butadiene styrene (ABS), polyethylene, polycarbonate, Polyamide (Nylon), high impact polystyrene, polypropylene, and combinations thereof), although other materials, including glass, are possible. In various implementations, further indicators (e.g., other haptic feedback components, an audio feedback component, or the like) can be included in addition to or as an alternative to the indicators included in the depicted implementation. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties.

Although other configurations are possible, the proximal end section 617 of the circuit board 634 of the depicted implementation includes a pair of conductive pins 636A, 636B, as well as a pressure sensor 640. In the depicted implementation, the conductive pins 636A, 636B comprise spring-loaded pins (e.g., electrical pogo pins) that extend through the upper frame 606 such that portions of the ends of the pins 636A, 636B extend into the cartridge receiving chamber 630) and are biased in that position due to the force of the internal springs of the conductive pins 636A, 636B. In such a manner, when a cartridge is coupled with the control device 600, the conductive pins 636A, 636B are configured to contact corresponding features of the cartridge and deflect downward (e.g., toward the lower frame 612) against the force of the springs, thus operatively connecting the installed cartridge with the control component 614 and the battery 616. In the depicted implementation, the conductive pins 636A, 636B comprise gold plated metal pins; however, other materials or combinations of materials, which may also include coatings and/or platings of electrically conductive materials, are possible. Examples of electrically conductive materials, include, but are not limited to, copper, aluminum, platinum, gold, silver, iron, steel, brass, bronze, graphite, conductive ceramic materials, and/or any combination thereof. Although other profiles are possible, the ends of the conductive pins 636A, 636B of the depicted implementation have a rounded profile such that deflection of the conductive pins 636A, 636B is facilitated when a cartridge is inserted into the cartridge receiving chamber 630. In other implementations, the conductive pins may be positioned in other locations of the cartridge receiving chamber 630, such as, for example, proximate the top of the cartridge receiving chamber 630. In other implementations, the conductive pins may be positioned at a point on the sides of the upper frame between the proximal end of the outer housing and the bottom wall of the upper frame. Further, in still other implementations the conductive pins may be positioned between a midpoint of the sidewalls and the proximal end of the outer housing (i.e., in an upper half of the sidewalls). Alternatively, the conductive pins may be positioned between a midpoint of the sidewalls and the bottom wall of the inner frame wall (e.g., in a lower half of the sidewalls). Moreover, in still other implementations, the conductive pins may be present at any position of the upper frame.

In various implementations, the aerosol delivery device may include an airflow sensor, pressure sensor, or the like. As noted above, the control component 614 of the depicted implementation includes a pressure sensor 640, which is positioned proximate and below the cartridge receiving chamber 630. The position and function of the pressure sensor 640 of the depicted implementation will be described below; however, in other implementations an airflow or pressure sensor may be positioned anywhere within the control device 600 so as to subject to airflow and/or a pressure change that can signal a draw on the device and thus cause the battery 616 to delivery power to the heating member of a cartridge. Various configurations of a printed circuit board and a pressure sensor, for example, are described in U.S. Pat. App. Pub. No. 2015/0245658 to Worm et al., the disclosure of which is incorporated herein by reference in its entirety. In the absence of an airflow sensor, pressure sensor, or the like, an aerosol delivery device may be activated manually, such as via a pushbutton that may be located on the control device and/or the cartridge. For example, one or more pushbuttons may be used as described in U.S. Pat. App. Pub. No. 2015/0245658 to Worm et al., which is incorporated herein by reference in its entirety. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pat. App. Pub. 2016/0158782 to Henry et al., which is incorporated herein by reference in its entirety.

Although not included in the depicted implementation, some implementations may include other types of input elements, which may replace or supplement an airflow or pressure sensor. The input may be included to allow a user to control functions of the device and/or for output of information to a user. Any component or combination of components may be utilized as an input for controlling the function of the device. In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In the depicted implementation, the pressure sensor seal 610 is configured to cover the pressure sensor 640 to protect it from any liquid and/or aerosol from an installed cartridge. In such a manner, the pressure sensor seal 610 of the depicted implementation (as well as other sealing members, including the motor housing 620, the pin seal 622, and/or an end cap seal 643) may be made of silicone rubber, boron nitride (BN) rubber, natural rubber, thermoplastic polyure-thane, or another resilient material. In some implementations, the upper portions of the end cap pins are configured to engage with the lower frame. For example, in some implementations the upper portions of the end cap pins are configured to create an interference or press-fit engagement with corresponding slotted openings in the lower frame. In various implementations, the interface between the end cap and the housing (e.g., via the interface between the end cap seal and the inner surface of the outer housing wall and/or the upper portions of the end cap pins and the lower frame) may create a press-fit engagement with the housing that is configured to be releasable so that the end cap (or end cap assembly) may be removable. In some implementations the control device may include one or more components configured to meet battery outgassing requirements under UL 8139. For example, the control device may include an end cap configured to eject in the event that sudden pressurization occurs within the control device enclosure. In one implementation, the end cap may include retaining pins that extend substantially perpendicularly from a wall of the end cap. The retaining pins may be configured to mate with receiving features (e.g., holes) in a frame of the control device to establish a friction fit or press fit that may be overcome if an internal pressure within the control device housing exceeds a defined internal pressure.

Although other configurations are possible, the distal end section 619 of the circuit board 634 includes the external connection element 638. In various implementations, the external connection element 638 may be configured for connecting to an external connector and/or a docking station or other power or data source. For example, in some implementations an external connector may comprise first and second connector ends that may be interconnected by a union, which may be, for example, a cord of variable length. In some implementations, the first connector end may be configured for electrical and, optionally, mechanical connection with the device, and the second connector end may be configured for connection to a computer or similar electronic device or for connection to a power source. An adaptor including a USB connector at one end and a power unit connector at an opposing end is disclosed in U.S. Pat. App. Pub. No. 2014/0261495 to Novak et al., which is incorporated herein by reference in its entirety. In the depicted implementation, the pin seal 622 is configured to seal the interface between the external connection element 638 and the end cap 624. In the depicted implementation, one or more pins of the external connection element 638 may extend through the end cap 624 of the control device as noted above. In the depicted implementation, the end cap 624 also includes a pair of end cap pins 641A, 641B that may be affixed to the end cap 624. For example, in some implementations, the end cap pins 641A, 641B may be insert-molded into the end cap 624. In some implementations, a bottom surface of the end cap pins 641A, 641B (which, in some implementations, may be flat) may be configured to provide attraction for magnets contained in an external charger assembly. In such a manner, the end cap pins 641A, 641B may be made of any material configured to be attracted by a magnet, such as various ferromagnetic materials, including, but not limited, to steel, iron, nickel, cobalt, other alloys, and/or any combination thereof.

The upper frame 606 of the depicted implementation includes a pair of magnets 646A, 646B that are exposed in the cartridge receiving chamber 630. In various implementations, the magnets 646A, 646B may comprise any type of magnets, including rare earth magnets. For example, in some implementations, one or more of the magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more of the magnets may comprise Samarium Cobalt magnets (also known as SmCo magnets). In still other implementations, one or more of the magnets may comprise Ceramic/Ferrite magnets. In other implementations, one or more of the magnets may comprise Aluminum-Nickel-Cobalt (AlNiCo) magnets. In any of the foregoing implementations, one or more of the magnets may be plated and/or coated. For example, in some implementations, one or more of the magnets may be coated with nickel. In other implementations, one or more magnets may be coated with one or more of zinc, tin, copper, epoxy, silver and/or gold. In some implementations, one or more of the magnets may be coated with combinations of these materials. For example, in one implementation, one or more of the magnets may be coated with nickel, copper, and nickel again. In another implementation, one or more of the magnets may be coated with nickel, copper, nickel, and a top coating of gold.

FIG. 24 illustrates an exploded perspective view of a cartridge 700, according to another example implementation of the present disclosure. FIG. 25 illustrates a front section view of the cartridge 700, and FIG. 26 illustrates a side section view of the cartridge 700. Although other configurations are possible, the cartridge 700 of the depicted implementation generally includes a mouthpiece 702, a mouthpiece insert 704, an upper aerosol channel insert 706, an upper cartridge seal 708, a tank 710 that defines a tank wall 711, a lower cartridge seal 712, a base member 714, a liquid transport element (e.g., a wick) 716, a heating member 718, a pair of heater connectors 720A, 720B, a pair of metal inserts 724A, 724B, and a bottom cap 726.

As shown in the figures, the mouthpiece 702 of the depicted implementation defines a proximal end and a distal end, with the proximal end of the mouthpiece 702 defining an exit portal 715 therein. In the depicted implementation, the mouthpiece insert 704 is configured to be located proximate the proximal end of the mouthpiece 702 such that it extends through the exit portal 715 thereof. In the depicted implementation, the mouthpiece 702 may be made of a moldable plastic material, such as polypropylene, although other materials are possible including, but not limited to, Tritan™ copolyester, acrylonitrile butadiene styrene (ABS), polyethylene, polycarbonate, Polyamide (Nylon), high impact polystyrene, and combinations thereof. In the depicted implementation, the mouthpiece insert 704 may be made of a molded polymer material, such as, for example, Tritan™ copolyester, although other materials are possible, including, but not limited to, polypropylene, acrylonitrile butadiene styrene (ABS), polyethylene, polycarbonate, Polyamide (Nylon), high impact polystyrene, and combinations thereof. In the depicted implementation, the upper cartridge seal 708 is overmolded onto/with the mouthpiece insert 704, although in other implementations these components may represent separate parts. In the depicted implementation, the upper cartridge seal 708 is configured to form a substantially air tight and liquid tight seal between the tank 710 and the mouthpiece 702. As such, the upper cartridge seal 708 may be made of thermoplastic elastomer. In other implementations, the upper cartridge seal may be made of other materials, including, but not limited to, silicone rubber, boron nitride (BN) rubber, natural rubber, thermoplastic polyurethane, or another resilient material. In the depicted implementation, the mouthpiece insert 704 is configured to receive and seal the upper aerosol channel insert 706 (see also FIGS. 25 and 26).

In the depicted implementation, the mouthpiece insert 704 and upper cartridge seal 708 assembly includes a flange feature such that the mouthpiece insert 704 and upper cartridge seal 708 may be installed from inside the mouthpiece 702 and may be configured for a press or snap-fit connection with the exit portal 715 and/or another portion of the mouthpiece 702. In other implementations, other attachment methods are possible (e.g., via adhesives, heat staking/welding, ultrasonic welding, etc.). In the depicted implementation, the mouthpiece 702 is configured to be secured to the tank 710 via snap features. For example, the mouthpiece 702 of the depicted implementation includes a ridge feature 743 (see FIG. 26) that extends around at least a portion of an inner surface thereof, and the tank 710 includes a corresponding groove feature 741 that extends around at least a portion of an outer surface thereof. In other implementations, these features may be reversed (e.g., the mouthpiece may include a groove and the tank may include a ridge feature). In still other implementations, other attachment methods are possible (e.g., via adhesives, heat staking/welding, ultrasonic welding, etc.).

In some implementations, the mouthpiece insert may exhibit a color associated with a distinctive characteristic of the cartridge. For example, in some implementations a cartridge of the present disclosure may include a liquid composition that includes a distinctive characteristic such as, for example, a particular flavorant (as discussed infra), or a specific strength of nicotine, although any characteristic of the cartridge may be considered a distinctive characteristic. For the purposes of the current description, the term "color" should be interpreted broadly, for example covering any color or any shade of the same color. It should also be noted that in some implementations, certain colors may be commonly associated with particular distinctive characteristics (e.g., the color green may be associated with a mint flavorant, and the color red may be associated with an apple flavorant); however, in other implementations, certain colors may be associated with particular distinctive characteristics according to an index or guide, which may be provided or made available to a user. Examples of distinctive characteristics are described in U.S. patent application Ser. No. 16/171,920, titled Aerosol Delivery Device with Flavor Indicator, which is incorporated herein by reference in its entirety.

The tank 710 of the depicted implementation defines a proximal end and a distal end, wherein the mouthpiece 702 is configured to engage the proximal end of the tank 710 and the bottom cap 726 is configured to engage the distal end of the tank 710. In the depicted implementation, the tank 710 also defines a reservoir cavity 728 that includes a closed proximal end and an open distal end. As such, the reservoir cavity 728 of the tank 710 is configured to contain a liquid composition (e.g., an e-liquid or aerosol precursor composition) therein. The closed proximal end of the reservoir cavity 728 allows the cavity to create a reliable seal on the top side of the liquid composition column. This may prevent the seepage/entry of air into the reservoir cavity from the top end when the cartridge is held upright. This may also prevent air from entering from the top of the liquid composition column, which may create a vacuum and may reduce the potential of the liquid composition to leak from the bottom of the tank through the liquid transport element or other passages.

Although other configurations are possible, in the depicted implementation a pair of internal aerosol flow tubes 733A, 733B are defined on opposite sides of the reservoir cavity 728 of the tank 710. In the case of an injection molded tank 710, the internal aerosol flow tubes are configured to be molded therein. As will be described in more detail below, aerosol produced in a vaporization chamber of the cartridge 700 is configured to travel through the aerosol flow tubes for delivery to a user.

In the depicted implementation, the tank wall 711 is configured to be transparent or translucent so that the liquid composition contained therein may be visible externally. As such, in the depicted implementation the entire tank wall 711 is configured to be transparent or translucent. Alternatively, in some implementations, only a portion of the tank wall or only a single side of the tank wall may be transparent or translucent while the remaining portions of the tank wall may be substantially opaque. In other implementations, the tank wall may be substantially opaque, and a strip extending from the proximal end of the tank to the distal end of the tank may be transparent or translucent. In further implementations, the tank wall may be colored. In some implementations, the color can be configured so that the liquid composition within the tank is still visible, such by using a transparent or translucent outer tank wall. In other implementations, the tank wall can be configured so that the outer tank wall has substantially opaque color. In the depicted implementation, the tank 710 is made of Tritan™ copolyester, although in other implementations the tank may be made of other materials including, but not limited to, acrylonitrile butadiene styrene (ABS), polyethylene, polycarbonate, Polyamide (Nylon), high impact polystyrene, polypropylene, and combinations thereof. Still other materials are possible, including, for example, glass.

For those implementations that include an indication window in the control device, at least a portion of the tank and/or at least a portion of the bottom cap may be visible when the cartridge is engaged with the control device. As noted above, in some implementations at least a portion of the tank wall 711 may be configured to be at least partially transparent or translucent so that the liquid composition contained therein is visible externally. Thus, in some implementations the relative amount of any liquid composition present in the tank may be visible through the indication window when the cartridge is engaged with the control device. In some implementations, the indication window may be located near the proximal end of the control device and is configured as an elongate oval shaped cut-out in the outer wall of the housing and the upper frame of the control device. It should be understood that in still other implementations, the indication window may have any other shapes and/or locations, as described above with respect to other depicted implementations, and, as noted, some implementations need not include any indication windows.

In the depicted implementation, the tank 710, and in particular, the reservoir cavity 728, contains a liquid composition, which may include an aerosol precursor composition and/or a flavorant. Reference is made to the above discussions of these materials and variations thereof. As shown in the figures, the cartridge 700 of the depicted implementation also includes a base member 714, which is configured to engage and cover the open distal end of the reservoir cavity 728 of the tank 710. The lower seal 712 of the depicted implementation is configured form a substantially air tight and liquid tight seal between a lower portion of the tank 710 and the bottom cap 726 (see also FIGS. 25 and 26), in particular, the lower seal 712 is configured to be located within a groove on an outer surface of the base member 714 so as to facilitate a substantially air tight and liquid tight seal between the base member 714 and tank 710. In the depicted implementation, the lower seal 712 is made of silicon rubber. In other implementations, the lower seal may be made of other materials, including, but not limited to, boron nitride (BN) rubber, natural rubber, thermoplastic polyurethane, or another resilient material. In the depicted implementation, the base member 714 is made of Tritan™ copolyester. In other implementations, the base member may be made of another material, including, but not limited to, acrylonitrile butadiene styrene (ABS), polyethylene, polycarbonate, Polyamide (Nylon), high impact polystyrene, polypropylene, and combinations thereof. The base member 714 of the depicted implementation also includes a plurality of slots 735 that are configured to provide liquid flow passages for the liquid composition contained in the reservoir cavity 728 of the tank 710 in order to facilitate transfer of the liquid to the liquid transport element 716. In some implementations, the slots may also provide retention of some liquid even when the bulk liquid composition in the reservoir cavity 728 is not in contact with the base member 714 (such as, for example, when the aerosol delivery device is upside down).

As shown in the figures, the liquid transport element 716 is disposed within the base member 714 and extends between the liquid composition in the reservoir cavity 728 and the heating member 718 (see also FIGS. 25 and 26). In the depicted implementation, the liquid transport element 716 is made of 100% cotton and, when installed in the cartridge 700, has a curved shape. In other implementations, however, the liquid transport element may have other shapes and may be formed of a variety of materials configured for transport of a liquid, such as by capillary action. For example, in some implementations the liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In other implementations, the liquid transport element may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference in their entireties.

As shown in the figures, the heating member 718 of the depicted implementation is also configured to be disposed within the base member 714. In particular, the heating member 718 of the depicted implementation comprises a heating element that has a substantially flat profile. While in some implementations the heating member may maintain a substantially flat profile when installed in a cartridge, when the heating member 718 of the depicted implementation is installed in the cartridge 700 it has a curved or bowed shape corresponding to the curved shape of the liquid transport element 716 (see also FIG. 26). Although other implementations may differ, in the depicted implementation the heating member 718 includes a first end, a second end, and a heater loop connecting the first end and the second end. In particular, the heater loop of the depicted implementation comprises a serpentine pattern of heater traces that are connected at respective ends thereof and that extend substantially transverse to a longitudinal axis of the heating member to connect the first end to the second end. While in some implementations the heater traces may be solid, the heater traces of the depicted implementation comprise a plurality of split traces. In the depicted implementation, the edges of the heating member are substantially solid and the plurality of split traces are located in a central area of the heating member. In such a manner, the heater loop of the depicted implementation may be configured to concentrate heat in an area of the heating element configured to be in contact with the liquid transport element 716.

In the depicted implementation, the heating member 718 in the installed position contacts a bottom surface of the liquid transport element 716. In the depicted implementation, the curved form of the flat heating member 718 may provide a large ratio of cross-sectional flow area to flow path length through the liquid transport element 716. This may provide increased performance with respect to delivery of the liquid composition to the liquid transport element 716. When installed, edges of the heating member 718 are configured to engage the base member 714 such that the heating member 718 maintains its curved shape. In such a manner, the curvature of the heating member 718 may also provide a compressive force against the liquid transport element 716. In addition, the spring recover force of the heating member 718 allows the edges of the heating member 718 to locate or lock into the base member 714, which may reduce or eliminate any need for additional features configured to hold the heating member 718 in the base member 714 from the other side. The installed curvature of the heating member 718 may also bias deflection of the heating member 718 that may occur with thermal expansion towards the liquid transport element 716, thus helping to maintain thermal contact between the heating member 718 and the liquid transport element 716. In the depicted implementation, the liquid transport element 716 and the heating member 718 comprise a heating assembly 734, which, together with the base member 714 and a nozzle member 755, define a vaporization chamber 732. In the depicted implementation, the nozzle member 755 includes a central opening and is located proximate the base member 726 and below the heating member 718. In the depicted implementation, the nozzle member 755 is made of silicone rubber although other materials are possible, including, but not limited to, boron nitride (BN) rubber, natural rubber, thermoplastic polyurethane, or another resilient material. In other implementations, the nozzle member may be made of other materials, including, but not limited to, moldable plastic materials.

It should be noted that some implementations need not include a heating assembly, but, rather, may include an atomization assembly configured to generate an aerosol in another manner. Some examples of atomization assemblies that generate aerosols in other ways can be found, for example, in U.S. application Ser. No. 16/544,326, filed on Aug. 19, 2019, and titled Detachable Atomization Assembly for Aerosol Delivery Device, which is incorporated herein by reference in its entirety.

In the depicted implementation, the heating member 718 is made of 316L stainless steel, although other materials may be used including, but not limited to, 316, 304, or 304L stainless steel. In other implementations, the heating member may be made of a different material, such as, for example, Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. Other heaters are described in U.S. Pat. App. Pub. No. 2016/0345633 to DePiano et al., which is incorporated herein by reference in its entirety.

Although in other implementations additional and/or differing contact features may be provided, the heating member 718 of the depicted implementation includes a pair of contact holes 731A, 731B that are configured to connect the heating member 718 to the heater connectors 720A, 720B of the cartridge 700. In depicted implementation, the heater connectors 720A, 720B are made of brass and are plated with gold over nickel. In other implementations, the heater connectors may be made of another conductive material that may or may not be plated. Examples of other possible conductive materials include, but are not limited to, copper, aluminum, platinum, gold, silver, iron, steel, bronze, graphite, conductive ceramic materials, and/or any combination thereof. In the depicted implementation, the contact holes 731A, 731B are configured to have an inner diameter that is less than an outer diameter of the mating portions of the heater connectors 720A, 720B. In some implementations, the contact holes may include one or more features (e.g., one or more fingers or extensions) that create an effective inner diameter that is less than an outer diameter of the mating portion of the heater connectors 720A, 720B. In such a manner, the contact holes 731A, 731B of the heating member 718 may create an interference fit with the upper ends of the heater connectors 720A, 720B such that the heating member 518 may maintain electrical contact with the heater connectors 720A, 720B. In the depicted implementation, the heater connectors 720A, 720B are insert-molded into the bottom cap 726.

The bottom cap 726 of the depicted implementation is configured to be secured to the distal end of the tank 710 via an ultrasonic welding process; however, other attachment methods are possible (e.g., via adhesives, heat staking/welding, snap-fit, etc.). In the depicted implementation, the bottom cap 726 of the cartridge 700 includes a cartridge air inlet channel 730, which is located in an approximate center of a bottom surface of the bottom cap 726. Although other configurations are possible, in the depicted implementation the cartridge air inlet channel 730 has an oval shape and includes a cross-bar feature that extends across the inlet between the opening of the air inlet channel 730 and the vaporization chamber 732.

Although other configurations are possible, the cartridge 700 of the depicted implementation also includes a pair of metal inserts 724A, 724B that are positioned in the bottom cap 726 and are configured to be exposed through the bottom surface thereof. In the depicted implementation, the metal inserts 724A, 724B are insert-molded into the bottom cap 726. In some implementations, the metal inserts may be configured for a press or snap fit connection with the bottom cap. In the depicted implementation, the metal inserts 724A, 724B are made of stainless steel plated with nickel; however, in other implementations the metal inserts may be made of any material configured to be attracted by a magnet, such as various ferromagnetic materials, including, but not limited, to iron, nickel, cobalt, alloys such as steel, and/or any combination thereof.

As noted above, when a cartridge is coupled with a cartridge receiving chamber of a control device, mechanical and electrical connections are created between the cartridge and the control device. FIG. 27 illustrates a front cross section view of an aerosol delivery device, according to an example implementation of the present invention. In particular, FIG. 27 depicts cartridge 700 coupled with control device 600. When the cartridge 700 of the depicted implementation is coupled with the upper frame 606 of the control device 600, a magnetic connection is created between the magnets 646A, 646B located in the upper frame 606 and the metal inserts 724A, 724B located in the bottom cap 726 of the cartridge 700. In addition, an electrical connection is created between the pair of conductive pins 636A, 636B of the control device 600 and the heater connectors 720A, 720B of the cartridge 700. Thus, when the cartridge 700 of the depicted implementation is coupled with the control device 600, the cartridge 700 is mechanically biased into connection with the control device 600 such that electrical connection is maintained between the cartridge 700 (and, in particular the heating assembly 734) and the control device (and in particular, the control component 614 and the battery 616).

When the cartridge 700 of the depicted implementation is coupled with the control device 600, the electrical connection between the control device 600 and the heating member 718 of the cartridge 700 (via the conductive pins 636A, 636B of the control device 600 and the heater connectors 720A, 720B of the cartridge) allows the control body 600 to direct electrical current to the heating member 718. In the depicted implementation, this may occur when a puff on the aerosol delivery device is detected (or, in other implementations, via actuation by the user, such as, for example, via a pushbutton). When a user of the aerosol device of the depicted implementation draws on the mouthpiece 702, inlet airflow is directed into the device via a gap between the cartridge 700 and the control device 600. In the depicted implementation, the gap comprises a peripheral gap that extends around substantially the entire periphery of the cartridge 700. It should be understood that in other implementations, the gap need not extend around the entire periphery of the cartridge, for example in some implementations the gap may comprise one or more gaps that extend around a portion of the periphery of the cartridge rather than the entire periphery, and in some implementations, the gap may comprise one or more individual holes. In the depicted implementation, the gap originates at an interface between an outside surface of the cartridge 700 and an inside surface of the control device 600. In particular, the gap originates at the interface of an outer surface of the mouthpiece 702 of the cartridge 700 and a top edge of the outer wall 604 of the housing 602 of the control device 600.

In the depicted implementation, the gap between the cartridge 700 and the control device 600 is established and maintained by features of the cartridge 700 and/or the control device 600. Although other configurations are possible, the upper frame 606 of the depicted implementation includes a pair of spaced protuberances located on one side of the cartridge receiving chamber 630 and a pair of spaced channels located on the opposite side of the cartridge receiving chamber 630. In the depicted implementation, the protuberances comprise raised elongate bosses that extend from an approximate top of the upper frame 606 to a recessed surface thereof. Likewise, the channels extend from an approximate top of the upper frame 606 to a recessed surface thereof. When the cartridge 700 of the depicted implementation is coupled with the control device 600, the protuberances located on the inner surface of the cartridge receiving chamber 630, the area of the upper frame between the channels (which, alternatively, may be considered a relative wide or large protuberance), and/or the area between the protuberances and the channels contact an outer surface of the cartridge 700 (and in particular, an outer surface of the mouthpiece 702 and/or an outer surface of the tank 710 and/or an outer surface of the bottom cap 726). In such a manner, these features position the cartridge 700 laterally with respect to the upper frame 606, thus establishing and maintaining the gap. It should be understood that in other implementations, positioning features may take other forms (including, for example, one or more bumps), and may be located on one or more components of the cartridge rather than (or in addition to) the control device.

As a user draws on the device, the air that enters the gap between the cartridge 700 and the control device 600 travels downward around the outside of the cartridge 700 and below the bottom cap 726 thereof. In the depicted implementation, inlet air is permitted to travel below the bottom cap 726 due to the vertical position of the cartridge 700 with respect to the bottom of the cartridge receiving chamber 730. In particular, the vertical position of the cartridge 700 of the depicted implementation is established using one or more of location features that extend upward from the recessed surface of the upper frame 606, at least one of which is configured to contact the bottom surface of the bottom cap 726 when the cartridge 700 is coupled with the control device 600. In the depicted implementation, the location features include at least a pair of bosses, each of which extends around a respective magnet 646. In such a manner, when the cartridge 700 is received into the control device 600, the gap between the cartridge 700 and the control device 600 is also established between the bottom of the bottom cap 726 and the recessed surface of the upper frame 606.

As noted above, although other configurations are possible, the bottom cap 726 of the depicted implementation includes an inlet channel 730 that is located in an approximate center of the bottom surface of the bottom cap 726. In the depicted implementation, the recessed surface of the receiving chamber 630 includes an opening therethrough, and the upper frame seal 608 of the depicted implementation includes a raised portion that is configured, when the cartridge 700 is installed in the receiving chamber 630, of abutting against the bottom of the bottom cap 726 and substantially surrounding the inlet channel 730. As such, air that enters the gap between the cartridge 700 and the control device 600 travels through the opening in the recessed surface of the receiving chamber 630 (and proximate the pressure sensor), through the raised portion of the upper frame seal, and into the inlet channel 730 of the cartridge 700. The air that enters through the inlet channel 730 then enters the vaporization chamber 732 of the cartridge. As the air is drawn through the inlet channel 730) into the cartridge 700, the pressure sensor 640 of the control device 600 detects the draw.

When a draw is detected by the pressure sensor 640, the control component 614 directs current through the heating member 718 in order to heat the heating member 718. As the heating member 718 heats, at least a portion of the liquid composition contained in the liquid transport element 716 is vaporized in the vaporization chamber 732. Accordingly, aerosol produced in the vaporization chamber 732 may then directed to the user. In particular, as the air enters the cartridge 700 via the air inlet channel 730, the air travels through the vaporization chamber 732 where it mixes with the vaporized liquid composition and becomes the aerosol. Due to the geometry of the vaporization chamber 732 and the bottom cap 726, the aerosol is split into two separate paths that extend through the inside of the bottom cap 726 and then through aerosol flow tubes that are defined on opposite sides of the reservoir cavity 728 of the tank 710. This relatively tortuous configuration may increase the effective flow path length and area for heat sinking, thus providing increased cooling of the aerosol stream prior to reaching the user. The two aerosol paths converge at the proximal end of the tank 710 and below the upper aerosol channel insert 706. The recombined aerosol then flows through the upper aerosol channel insert 706 and out of the exit portal 715 of the mouthpiece 700, to the user.

Although other configurations are possible, in the depicted implementation, the upper aerosol channel insert 706 is configured to absorb liquid formed by deposition and/or condensation from aerosol formed in the vaporization chamber 732, and is configured to have rigid or semi-rigid properties. As such, the upper aerosol channel insert 706 of the depicted implementation may be made of a fibrous, sintered beaded, or open cell foam material. For example, in some implementations, the upper aerosol channel insert may be made of a fibrous bonded polyethylene (PE) or polyethylene terephthalate (PET) material. In such a manner, the upper aerosol channel insert 706 may be configured for a press or snap fit attachment with the mouthpiece 702 (and in particular the mouthpiece insert 704). The upper aerosol channel insert 706 is also configured to help to prevent accumulation of liquid from exiting the cartridge 700 through the mouthpiece 702. In addition, the upper aerosol channel insert 706 is located in such a way that aerosol produced in the vaporization chamber 732 passes through the insert 706 just prior to exiting the cartridge 700. In the depicted implementation, the inside cavity of the upper aerosol channel insert 706 may also serve as a cooling chamber within which the formed aerosol can be allowed to expand and/or cool before passing through the exit portal 715. In some implementations, the vaporization chamber 732 and the cooling chamber may be configured to have a defined relative volume ratio.

FIG. 28 illustrates an exploded perspective view of a control device of an aerosol delivery device, according to another example implementation of the present disclosure. As shown in the figure, the control device 800 of the depicted implementation generally includes a housing 802 defining an outer wall 804, an upper frame 806, an upper frame seal 808, a pressure sensor seal 810, a lower frame 812, a control component 814, a battery 816, a vibration motor 818, a motor housing 820, a pin seal 822, an end cap 824, a light diffuser 826, and a vent 839. The control device 800 of the depicted implementation also includes a front foam pad 831, a plurality of side foam pads 837 (which may allow room for the battery to expand during use), a battery insulator 839, and an electrical insulator 847. In the depicted implementation, the battery insulator 839 is configured to be disposed between the battery 816 and the control component 814, the side foam pads 837 are configured to be disposed on opposite sides of the battery 816, the front foam pad 831 is configured to be disposed between the control component 841 and the housing 804, and the electrical insulator 847 is configured to serve an insulator for solder points when the motor and the control component meet. In various implementations, any one or any combination of these components need not be included. In addition, in various implementations one or more of these components may be replaced with curing sealant, potting, tape, etc. In some implementations, the control device may include one or more other seals, which may include, for example, an upper chassis seal and/or a lower chassis seal.

The arrangement of the components of the control device 800 is illustrated in FIG. 29, which depicts a section view of the control device, according to an example implementation of the present disclosure. In particular, FIG. 29 illustrates a front section view of the control device 800. As illustrated in the figure, the upper frame 806 of the control device 800 defines a cartridge receiving chamber 830 within which a cartridge may be coupled. In the depicted implementation, the upper frame 806 and the housing 802 represent different parts; however, in other implementations, the upper frame and the housing may be continuously formed such that they comprise the same part.

In the depicted implementation, the housing 802 comprises a metal material, such as, for example, aluminum; however, in other implementations the housing may comprise a metal alloy material, and in still other implementations the housing may comprise a molded polymer material. In the depicted implementation, one or more of the upper frame 806, lower frame 812, and end cap 824 may be made of a molded polymer material, such as, for example, a molded plastic material (e.g., polybutylene terephthalate (PBT), acrylonitrile butadiene styrene (ABS), polyethylene, polycarbonate, Polyamide (Nylon), high impact polystyrene, polypropylene, and combinations thereof). In other implementations, one or more of these components may be made of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

In the depicted implementation, the lower frame 812 is configured to contain the battery 816 in an interior area thereof. In the depicted implementation, the battery may comprise a lithium polymer (LiPo) battery; however various other batteries may be suitable. Some other examples of batteries that can be used according to the disclosure are described in U.S. Pat. App. Pub. No. 2010/0028766 to Peckerar et al., the disclosure of which is incorporated herein by reference in its entirety. In some implementations, other types of power sources may be utilized. For example, in various implementations a power source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (e.g., cigarette lighter receptacle, USB port, etc.), connection to a computer, such as through a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

The control device 800 of the depicted implementation includes a control mechanism in the form of the control component 814, which is configured, in part, to control the amount of electric power provided to the heating member of the cartridge. Although other configurations are possible, the control component 814 of the depicted implementation comprises a circuit board 834 (e.g., a printed circuit board (PCB)) that includes both rigid and flexible portions. In particular, the circuit board 834 of the depicted implementation includes a rigid central section 815 and two rigid end sections comprising a proximal end section 817 and a distal end section 819, with each of the end sections 817, 819 being connected to the central section 815 by a respective flexible connection. In such a manner, when the lower frame 812, battery 816, and circuit board 834 are assembled into the control device 800, the central section 815 of the circuit board 834 is configured to be disposed proximate a major surface of the battery 816, and the two end sections 817, 819 are configured to be disposed substantially perpendicular to the central section 815. In particular, the proximal end section 817 of the circuit board 834 is configured to extend over the top of the lower frame 812, and the distal end section 819 is configured to extend over the bottom of the lower frame 812. The lower frame 812 of the control device 800 is also configured to contain the motor housing 820, into which the vibration motor 818 is received. In various implementations, the vibration motor 818 may provide haptic feedback relating to various operations of the device. The central section 815 of the depicted implementation also includes an indicator in the form of a light source 821. In some implementations, the light source may comprise, for example, at least one light emitting diode (LED) capable of providing one or more colors of light. In other implementations, the light source may be configured to illuminate in only one color, while in other implementations, the light source may be configured to illuminate in variety of different colors. In still other implementations, the light source may be configured to provide white light. In the depicted implementation, the light source 821 comprises an RGB (red, green, blue) LED that is configured to provide a variety of colors of light, including white light. The central section 815 of the depicted circuit board 834 also includes electrical contacts 823 that are configured to operatively connect the circuit board 834 to the vibration motor 818. Other types of electronic components, structures and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al, and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference. Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In the depicted implementation, the vent 845 is configured to be installed on the inside of the housing 802 such that it covers the aperture 825. As such, in the depicted implementation one side of the vent 845 may include a pressure sensitive adhesive. In the depicted implementation, the vent 845 comprises a breathable membrane material, such as, for example, a Gore-Tex® material; however, other suitable materials are possible. In the depicted implementation, the light source 821 is covered by the light diffuser 826, a portion of which is configured to be received by the end cap 824. In the depicted implementation, the light diffuser forms a press-fit connection with the end cap 824; however, in other implementations, the light diffuser may be affixed to the end cap in another manner. When assembled, the light diffuser 826 is positioned in or proximate an aperture 825 defined in the outer wall 804 of the housing 802 and proximate a distal end thereof. In the depicted implementation, the aperture 825 comprises a narrow, elongate opening; however, in other implementations, the aperture may be provided in any desired shape and may be positioned at any location on the control device 800. In some implementations, the light diffuser 826 may comprise a transparent or translucent member configured to allow a user to view the light source 821 from the outside of the housing 802. In the depicted implementation, the light diffuser 826 may be made of a molded polymer material, such as, for example, a molded plastic material (e.g., poly butylene terephthalate (PBT), acrylonitrile butadiene styrene (ABS), polyethylene, polycarbonate, Polyamide (Nylon), high impact polystyrene, polypropylene, and combinations thereof), although other materials, including glass, are possible. In various implementations, further indicators (e.g., other haptic feedback components, an audio feedback component, or the like) can be included in addition to or as an alternative to the indicators included in the depicted implementation. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties.

Although other configurations are possible, the proximal end section 817 of the circuit board 834 of the depicted implementation includes a pair of conductive pins 836A, 836B, as well as a pressure sensor 840. In the depicted implementation, the conductive pins 836A. 836B comprise spring-loaded pins (e.g., electrical pogo pins) that extend through the upper frame 806 such that portions of the ends of the pins 836A, 836B extend into the cartridge receiving chamber 830) and are biased in that position due to the force of the internal springs of the conductive pins 836A, 636B. In such a manner, when a cartridge is coupled with the control device 800, the conductive pins 836A, 836B are configured to contact corresponding features of the cartridge and deflect downward (e.g., toward the lower frame 812) against the force of the springs, thus operatively connecting the installed cartridge with the control component 814 and the battery 816. In the depicted implementation, the conductive pins 836A, 836B comprise gold plated metal pins; however, other materials or combinations of materials, which may also include coatings and/or platings of electrically conductive materials, are possible. Examples of electrically conductive materials, include, but are not limited to, copper, aluminum, platinum, gold, silver, iron, steel, brass, bronze, graphite, conductive ceramic materials, and/or any combination thereof. Although other profiles are possible, the ends of the conductive pins 836A, 836B of the depicted implementation have a rounded profile such that deflection of the conductive pins 836A, 836B is facilitated when a cartridge is inserted into the cartridge receiving chamber 830. In other implementations, the conductive pins may be positioned in other locations of the cartridge receiving chamber 830, such as, for example, proximate the top of the cartridge receiving chamber 830. In other implementations, the conductive pins may be positioned at a point on the sides of the upper frame between the proximal end of the outer housing and the bottom wall of the upper frame. Further, in still other implementations the conductive pins may be positioned between a midpoint of the sidewalls and the proximal end of the outer housing (i.e., in an upper half of the sidewalls). Alternatively, the conductive pins may be positioned between a midpoint of the sidewalls and the bottom wall of the inner frame wall (e.g., in a lower half of the sidewalls). Moreover, in still other implementations, the conductive pins may be present at any position of the upper frame.

In various implementations, the aerosol delivery device may include an airflow sensor, pressure sensor, or the like. As noted above, the control component 814 of the depicted implementation includes a pressure sensor 840, which is positioned proximate and below the cartridge receiving chamber 830. The position and function of the pressure sensor 840 of the depicted implementation will be described below; however, in other implementations an airflow or pressure sensor may be positioned anywhere within the control device 800 so as to subject to airflow and/or a pressure change that can signal a draw on the device and thus cause the battery 816 to delivery power to the heating member of a cartridge. Various configurations of a printed circuit board and a pressure sensor, for example, are described in U.S. Pat. App. Pub. No. 2015/0245658 to Worm et al., the disclosure of which is incorporated herein by reference in its entirety. In the absence of an airflow sensor, pressure sensor, or the like, an aerosol delivery device may be activated manually, such as via a pushbutton that may be located on the control device and/or the cartridge. For example, one or more pushbuttons may be used as described in U.S. Pat. App. Pub. No. 2015/0245658 to Worm et al., which is incorporated herein by reference in its entirety. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pat. App. Pub. 2016/0158782 to Henry et al., which is incorporated herein by reference in its entirety.

Although not included in the depicted implementation, some implementations may include other types of input elements, which may replace or supplement an airflow or pressure sensor. The input may be included to allow a user to control functions of the device and/or for output of information to a user. Any component or combination of components may be utilized as an input for controlling the function of the device. In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In the depicted implementation, the pressure sensor seal 810 is configured to cover the pressure sensor 840 to protect it from any liquid and/or aerosol from an installed cartridge. In such a manner, the pressure sensor seal 810 of the depicted implementation, as well as other sealing members, including, for example, the upper frame seal 808 (and/or cartridge intake seal 850), the motor housing 820, the pin seal 822 (and/or the end cap seal 843), may be made of silicone rubber, boron nitride (BN) rubber, natural rubber, thermoplastic polyurethane, or another resilient material. In some implementations, the upper portions of the end cap pins are configured to engage with the lower frame. For example, in some implementations the upper portions of the end cap pins are configured to create an interference or press-fit engagement with corresponding slotted openings in the lower frame. In various implementations, the interface between the end cap and the housing (e.g., via the interface between the end cap seal and the inner surface of the outer housing wall and/or the upper portions of the end cap pins and the lower frame) may create a press-fit engagement with the housing that is configured to be releasable so that the end cap (or end cap assembly) may be removable. In some implementations the control device may include one or more components configured to meet battery outgassing require-ments under UL 8139. For example, the control device may include an end cap configured to eject in the event that sudden pressurization occurs within the control device enclosure. In one implementation, the end cap may include retaining pins that extend substantially perpendicularly from a wall of the end cap. The retaining pins may be configured to mate with receiving features (e.g., holes) in a frame of the control device to establish a friction fit or press fit that may be overcome if an internal pressure within the control device housing exceeds a defined internal pressure.

Although other configurations are possible, the distal end section 819 of the circuit board 834 includes the external connection element 838. In various implementations, the external connection element 838 may be configured for connecting to an external connector and/or a docking station or other power or data source. For example, in some implementations an external connector may comprise first and second connector ends that may be interconnected by a union, which may be, for example, a cord of variable length. In some implementations, the first connector end may be configured for electrical and, optionally, mechanical con-nection with the device, and the second connector end may be configured for connection to a computer or similar electronic device or for connection to a power source. An adaptor including a USB connector at one end and a power unit connector at an opposing end is disclosed in U.S. Pat. App. Pub. No. 2014/0261495 to Novak et al., which is incorporated herein by reference in its entirety. In the depicted implementation, the pin seal 822 is configured to seal the interface between the external connection element 838 and the end cap 824. In the depicted implementation, one or more pins of the external connection element 838 may extend through the end cap 824 of the control device as noted above. In the depicted implementation, the end cap 824 also includes a pair of end cap pins 841A, 841B that may be affixed to the end cap 824. For example, in some implementations, the end cap pins 841A, 641B may be insert-molded into the end cap 824. In some implementa-tions, a bottom surface of the end cap pins 841A, 841B (which, in some implementations, may be flat) may be configured to provide attraction for magnets contained in an external charger assembly. In such a manner, the end cap pins 841A, 841B may be made of any material configured to be attracted by a magnet, such as various ferromagnetic materials, including, but not limited, to steel, iron, nickel, cobalt, other alloys, and/or any combination thereof. In the depicted implementation, the opposite ends of the end cap pins 841A, 841B have multiple diameter sections. For example, each of the pins 841A, 841B defines at least three sections above the end cap 824, a first section proximate the end cap 824, a second section above the first section, and end section distal from the end cap 824. In the depicted imple-mentation, the end sections of the pins 841A, 841B have an angled diameter, and the first section has an outer diameter larger than that of the second section.

The upper frame 806 of the depicted implementation includes a pair of magnets 846A, 846B that are exposed in the cartridge receiving chamber 830. In various implemen-tations, the magnets 846A, 846B may comprise any type of magnets, including rare earth magnets. For example, in some implementations, one or more of the magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more of the mag-nets may comprise Samarium Cobalt magnets (also known as SmCo magnets). In still other implementations, one or more of the magnets may comprise Ceramic/Ferrite mag-nets. In other implementations, one or more of the magnets may comprise Aluminum-Nickel-Cobalt (AlNiCo) magnets. In any of the foregoing implementations, one or more of the magnets may be plated and/or coated. For example, in some implementations, one or more of the magnets may be coated with nickel. In other implementations, one or more magnets may be coated with one or more of zinc, tin, copper, epoxy, silver and/or gold. In some implementations, one or more of the magnets may be coated with combinations of these materials. For example, in one implementation, one or more of the magnets may be coated with nickel, copper, and nickel again. In another implementation, one or more of the mag-nets may be coated with nickel, copper, nickel, and a top coating of gold.

FIG. 30 illustrates a perspective partial section view of a control device of an aerosol delivery device. In particular, FIG. 30 illustrates a partial section view of the housing 802, upper frame 806, upper frame seal 808, pressure sensor seal 810, pressure sensor 840, cartridge intake seal 850, and lower frame 812 of the control device 800. In the depicted implementation, the cartridge intake seal 850 forms an outwardly extending radial profile (e.g., a suction cup-like profile) that extends above (e.g., toward/into the receiving chamber 830) the recessed surface 844 of the receiving chamber 830. In the depicted implementation, the cartridge intake seal 850 is part of the same overmold that includes the upper frame seal 808 (and thus may be made of the same material); however, in other implementations these seals may form separate parts, which may or may not be the result of an overmolding process. As shown in the figure, a portion of the conductive pins 836A, 836B of the control component 814 extend through the upper frame 806 and a portion of the cartridge intake seal 850. In particular, a portion of the conductive pins 836A, 836B of the depicted implementa-tion, which as noted above comprise spring-loaded contacts, extend through a recessed surface 844 and a portion of the cartridge intake seal 850 of the upper frame 806 and into the cartridge receiving chamber 830.

As also shown in the figure, the upper frame 806 includes a pair of magnets 846A, 846B that are also exposed in the cartridge receiving chamber 830. In various implementations, the magnets 846A, 846B may comprise any type of magnets, including rare earth magnets. For example, in some implementations, one or more of the magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more of the magnets may comprise Samarium Cobalt magnets (also known as SmCo magnets). In still other implementations, one or more of the magnets may comprise Ceramic/Ferrite magnets. In other implementations, one or more of the magnets may comprise Aluminum-Nickel-Cobalt (AlNiCo) magnets. In any of the foregoing implementations, one or more of the magnets may be plated and/or coated. For example, in some implementations, one or more of the magnets may be coated with nickel. In other implementations, one or more magnets may be coated with one or more of zinc, tin, copper, epoxy, silver and/or gold. In some implementations, one or more of the magnets may be coated with combinations of these materials. For example, in one implementation, one or more of the magnets may be coated with nickel, copper, and nickel again. In another implementation, one or more of the magnets may be coated with nickel, copper, nickel, and a top coating of gold.

In the depicted implementation, each magnet 846A, 846B is substantially surrounded by a respective location feature 848A, 848B of the upper frame 806, wherein the location features 848A, 848B also extend into the cartridge receiving chamber 830. As will be discussed in more detail below; one or more of the location features 848A, 848B of the upper frame 806 are configured as stopping or vertical locating features for an installed cartridge and are thus configured to position the cartridge with respect to the recessed surface 844 of the upper frame 806 of the control device 800. In the depicted implementation, the recessed surface 844 of the upper frame 806 also defines an air intake opening 852, which extends through the upper frame 806 and proximate the pressure sensor seal 810. In the depicted implementation, the air intake opening 852 is configured to receive air drawn into the aerosol delivery device by a user (see FIG. 35).

As noted above, a portion of the cartridge is configured to be coupled with the cartridge receiving chamber 830 of the inner frame 806 of the control device 800 such that mechanical and electrical connections are created between the cartridge and the control device 800. In particular, when as cartridge is coupled with the upper frame 806 of the control device 800, a magnetic connection is created between the magnets 846A, 846B located in the upper frame 806 and corresponding features of the cartridge, and an electrical connection is created between the pair conductive pins 836A, 236B of the control device 800 and corresponding features of the cartridge. As such, when a cartridge is received in the receiving chamber 830 of the control device 800, the cartridge may be operatively connected to the control component 814 and the battery 816 of the control device 800. In addition, the outwardly angled profile of the cartridge intake seal 850 deflects downward thus forming a substantially air tight seal with the bottom of the cartridge, and in particular, around the air inlet channel of a cartridge. Thus, when a cartridge is coupled with the control device, the cartridge is mechanically biased into connection with the control device such that electrical connection is maintained between the cartridge and the control device and a seal is formed between the cartridge and the control device. It should be understood that for the purposes of the present disclosure, the term "operatively connected" and other related forms thereof should be interpreted broadly so as to encompass components that are directly connected and/or connected via one or more additional components.

FIG. 31 illustrates a perspective view of an end cap assembly, according to an example implementation of the present disclosure. In particular, FIG. 31 illustrates a perspective view of the end cap 824, light diffuser 826, and end cap pins 841A, 841B. As shown in the figure, the end cap 824 also includes an end cap seal 843 that provides a sealing interface between the end cap 824 and the housing 802, and in particular, an inner surface of the outer wall 804. The depicted implementation also includes a pin seal 822, which is configured to seal the interface between the external connection element and the end cap. In the depicted implementation, the pin seal 822 and the end cap seal 843 comprise a single overmolded part; however, in other implementations these parts may be separate. In various implementations, the end cap seal 843 and/or pin seal 822 may be made of silicone rubber, boron nitride (BN) rubber, natural rubber, thermoplastic polyurethane, or another resilient material. As also shown in FIG. 29, in various implementations the upper portions of the end cap pins 841A, 841B may be configured to engage with the lower frame 812. For example, in the depicted implementation the upper portions of the end cap pins 841A, 841B are configured to create a sliding or an interference or press-fit engagement with corresponding slotted openings in the lower frame 812. In various implementations, the interface between the end cap 824 and the housing 802 (e.g., via the interface between the end cap seal 843 and the inner surface of the outer housing wall 804 and/or the upper portions of the end cap pins 841A, 841B and the lower frame 812) may create a press-fit engagement with the housing 802 that is configured to be releasable so that the end cap 824 (or end cap assembly) may be removable.

In various implementations, the control device may include one or more components configured to meet battery outgassing requirements under UL 8139. For example, the control device may include an end cap configured to eject in the event that sudden pressurization occurs within the control device enclosure. In one implementation, the end cap may include retaining pins that extend substantially perpendicularly from a wall of the end cap. The retaining pins may be configured to mate with receiving features (e.g., holes) in a frame of the control device to establish a friction fit or press fit that may be overcome if an internal pressure within the control device housing exceeds a defined internal pressure.

FIGS. 32, 33, and 34 illustrate a cartridge according to another example implementation of the present disclosure. In particular, FIG. 32 illustrates an exploded perspective view of a cartridge 900, FIG. 33 illustrates a front section view of the cartridge 900, and FIG. 34 illustrates a side section view of the cartridge 900. Although other configurations are possible, the cartridge 900 of the depicted implementation generally includes a mouthpiece 902, a mouthpiece insert 904, an upper aerosol channel insert 906, an upper cartridge seal 908, a tank 910 that defines a tank wall 911, a lower cartridge seal 912, a base member 914, a liquid transport element (e.g., a wick) 916, a heating member 918, a pair of heater connectors 920A, 920B, a pair of metal inserts 924A, 924B, and a bottom cap 926.

As shown in the figures, the mouthpiece 902 of the depicted implementation defines a proximal end and a distal end, with the proximal end of the mouthpiece 902 defining an exit portal 915 therein. In the depicted implementation, the mouthpiece insert 904 is configured to be located proximate the proximal end of the mouthpiece 902 such that it extends through the exit portal 915 thereof. In the depicted implementation, the mouthpiece 902 may be made of a moldable plastic material, such as polypropylene, although other materials are possible including, but not limited to, Tritan™ copolyester, acrylonitrile butadiene styrene (ABS), polyethylene, polycarbonate, Polyamide (Nylon), high impact polystyrene, and combinations thereof. In the depicted implementation, the mouthpiece insert 904 may be made of a molded polymer material, such as, for example, Tritan™ copolyester, although other materials are possible, including, but not limited to, polypropylene, acrylonitrile butadiene styrene (ABS), polyethylene, polycarbonate, Polyamide (Nylon), high impact polystyrene, and combinations thereof. In the depicted implementation, the upper cartridge seal 908 is overmolded onto/with the mouthpiece insert 904, although in other implementations these components may represent separate parts. In the depicted implementation, the upper cartridge seal 908 is configured to form a substantially air tight and liquid tight seal between the tank 910) and the mouthpiece 902. As such, the upper cartridge seal 908 may be made of thermoplastic elastomer. In other implementations, the upper cartridge seal may be made of other materials, including, but not limited to, silicone rubber, boron nitride (BN) rubber, natural rubber, thermoplastic polyurethane, or another resilient material. In the depicted implementation, the mouthpiece insert 904 is configured to receive and seal the upper aerosol channel insert 906.

In the depicted implementation, the mouthpiece insert 904 and upper cartridge seal 908 assembly includes a flange feature such that the mouthpiece insert 904 and upper cartridge seal 908 may be installed from inside the mouthpiece 902 and may be configured for a press or snap-fit connection with the exit portal 915 and/or another portion of the mouthpiece 902. In other implementations, other attachment methods are possible (e.g., via adhesives, heat staking/welding, ultrasonic welding, etc.). In the depicted implementation, the mouthpiece 902 is configured to be secured to the tank 910 via snap features. For example, the mouthpiece 902 of the depicted implementation includes a ridge feature that extends around at least a portion of an inner surface thereof, and the tank 910 includes a corresponding groove feature that extends around at least a portion of an outer surface thereof. In other implementations, these features may be reversed (e.g., the mouthpiece may include a groove and the tank may include a ridge feature). In still other implementations, other attachment methods are possible (e.g., via adhesives, heat staking/welding, ultrasonic welding, etc.).

In some implementations, the mouthpiece insert may exhibit a color associated with a distinctive characteristic of the cartridge. For example, in some implementations a cartridge of the present disclosure may include a liquid composition that includes a distinctive characteristic such as, for example, a particular flavorant (as discussed infra), or a specific strength of nicotine, although any characteristic of the cartridge may be considered a distinctive characteristic. For the purposes of the current description, the term "color" should be interpreted broadly, for example covering any color or any shade of the same color. It should also be noted that in some implementations, certain colors may be commonly associated with particular distinctive characteristics (e.g., the color green may be associated with a mint flavorant, and the color red may be associated with an apple flavorant); however, in other implementations, certain colors may be associated with particular distinctive characteristics according to an index or guide, which may be provided or made available to a user. Examples of distinctive characteristics are described in U.S. patent application Ser. No. 16/171,920, titled Aerosol Delivery Device with Flavor Indicator, which is incorporated herein by reference in its entirety.

The tank 910 of the depicted implementation defines a proximal end and a distal end, wherein the mouthpiece 902 is configured to engage the proximal end of the tank 910 and the bottom cap 926 is configured to engage the distal end of the tank 910. In the depicted implementation, the tank 910 also defines a reservoir cavity 928 that includes a closed proximal end and an open distal end. As such, the reservoir cavity 928 of the tank 910 is configured to contain a liquid composition (e.g., an e-liquid or aerosol precursor composition) therein. The closed proximal end of the reservoir cavity 928 allows the cavity to create a reliable seal on the top side of the liquid composition column. This may prevent the seepage/entry of air into the reservoir cavity from the top end when the cartridge is held upright. This may also prevent air from entering from the top of the liquid composition column, which may create a vacuum and may reduce the potential of the liquid composition to leak from the bottom of the tank through the liquid transport element or other passages.

Although other configurations are possible, in the depicted implementation a pair of internal aerosol flow tubes 933A, 933B are defined on opposite sides of the reservoir cavity 928 of the tank 910. In the case of an injection molded tank 910, the internal aerosol flow tubes are configured to be molded therein. As will be described in more detail below, aerosol produced in a vaporization chamber of the cartridge 900 is configured to travel through the aerosol flow tubes for delivery to a user.

In the depicted implementation, the tank wall 911 is configured to be transparent or translucent so that the liquid composition contained therein may be visible externally. As such, in the depicted implementation the entire tank wall 911 is configured to be transparent or translucent. Alternatively, in some implementations, only a portion of the tank wall or only a single side of the tank wall may be transparent or translucent while the remaining portions of the tank wall may be substantially opaque. In other implementations, the tank wall may be substantially opaque, and a strip extending from the proximal end of the tank to the distal end of the tank may be transparent or translucent. In further implementations, the tank wall may be colored. In some implementations, the color can be configured so that the liquid composition within the tank is still visible, such by using a transparent or translucent outer tank wall. In other implementations, the tank wall can be configured so that the outer tank wall has substantially opaque color. In the depicted implementation, the tank 910 is made of Tritan™ copolyester, although in other implementations the tank may be made of other materials including, but not limited to, acrylonitrile butadiene styrene (ABS), polyethylene, polycarbonate, Polyamide (Nylon), high impact polystyrene, polypropylene, and combinations thereof. Still other materials are possible, including, for example, glass.

For those implementations that include an indication window in the control device, at least a portion of the tank and/or at least a portion of the bottom cap may be visible when the cartridge is engaged with the control device. As noted above, in some implementations at least a portion of the tank wall 911 may be configured to be at least partially transparent or translucent so that the liquid composition contained therein is visible externally. Thus, in some implementations the relative amount of any liquid composition present in the tank may be visible through the indication window when the cartridge is engaged with the control device. In some implementations, the indication window may be located near the proximal end of the control device and is configured as an elongate oval shaped cut-out in the outer wall of the housing and the upper frame of the control device. It should be understood that in still other implementations, the indication window may have any other shapes and/or locations, as described above with respect to other depicted implementations, and, as noted, some implementations need not include any indication windows.

In the depicted implementation, the tank 910, and in particular, the reservoir cavity 928, contains a liquid composition, which may include an aerosol precursor composition and/or a flavorant. Reference is made to the above discussions of these materials and variations thereof. As shown in the figures, the cartridge 900 of the depicted implementation also includes a base member 914, which is configured to engage and cover the open distal end of the reservoir cavity 928 of the tank 910. In the depicted implementation, the lower cartridge seal 912 is overmolded onto/ with the mouthpiece insert 904, although in other implementations these components may represent separate parts. The lower cartridge seal 912 of the depicted implementation is configured form a substantially air tight and liquid tight seal between a lower portion of the tank 910 and the bottom cap 926. In the depicted implementation, the lower cartridge seal 912 is made of silicon rubber. In other implementations, the lower seal may be made of other materials, including, but not limited to, boron nitride (BN) rubber, natural rubber, thermoplastic polyurethane, or another resilient material. In the depicted implementation, the base member 914 is made of Tritan™ copolyester. In other implementations, the base member may be made of another material, including, but not limited to, acrylonitrile butadiene styrene (ABS), polyethylene, polycarbonate. Polyamide (Nylon), high impact polystyrene, polypropylene, and combinations thereof. The base member 914 of the depicted implementation may also include a plurality of slots that are configured to provide liquid flow passages for the liquid composition contained in the reservoir cavity 928 of the tank 910 in order to facilitate transfer of the liquid to the liquid transport element 716. In some implementations, the slots may also provide retention of some liquid even when the bulk liquid composition in the reservoir cavity 928 is not in contact with the base member 914 (such as, for example, when the aerosol delivery device is upside down).

As shown in the figures, the liquid transport element 916 is disposed within the base member 914 and extends between the liquid composition in the reservoir cavity 928 and the heating member 918. In the depicted implementation, the liquid transport element 916 is made of 100% cotton and, when installed in the cartridge 900, has a curved shape. In other implementations, however, the liquid transport element may have other shapes and may be formed of a variety of materials configured for transport of a liquid, such as by capillary action. For example, in some implementations the liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In other implementations, the liquid transport element may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/ 0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference in their entireties.

As shown in the figures, the heating member 918 of the depicted implementation is also configured to be disposed within the base member 914. In particular, the heating member 918 of the depicted implementation comprises a heating element that has a substantially flat profile. While in some implementations the heating member may maintain a substantially flat profile when installed in a cartridge, when the heating member 918 of the depicted implementation is installed in the cartridge 900 it has a curved or bowed shape corresponding to the curved shape of the liquid transport element 916. Although other implementations may differ, in the depicted implementation the heating member 918 includes a first end, a second end, and a heater loop connecting the first end and the second end. In particular, the heater loop of the depicted implementation comprises a serpentine pattern of heater traces that are connected at respective ends thereof and that extend substantially transverse to a longitudinal axis of the heating member to connect the first end to the second end. While in some implementations the heater traces may be solid, the heater traces of the depicted implementation comprise a plurality of split traces. In the depicted implementation, the edges of the heating member are substantially solid and the plurality of split traces are located in a central area of the heating member. In such a manner, the heater loop of the depicted implementation may be configured to concentrate heat in an area of the heating element configured to be in contact with the liquid transport element 916.

In the depicted implementation, the heating member 918 in the installed position contacts a bottom surface of the liquid transport element 916. In the depicted implementation, the curved form of the flat heating member 918 may provide a large ratio of cross-sectional flow area to flow path length through the liquid transport element 916. This may provide increased performance with respect to delivery of the liquid composition to the liquid transport element 916. When installed, edges of the heating member 918 are configured to engage the base member 914 such that the heating member 918 maintains its curved shape. In such a manner, the curvature of the heating member 918 may also provide a compressive force against the liquid transport element 916. In addition, the spring recover force of the heating member 918 allows the edges of the heating member 918 to locate or lock into the base member 914, which may reduce or eliminate any need for additional features config-ured to hold the heating member 918 in the base member 914 from the other side. The installed curvature of the heating member 918 may also bias deflection of the heating member 918 that may occur with thermal expansion towards the liquid transport element 916, thus helping to maintain thermal contact between the heating member 918 and the liquid transport element 916. In the depicted implementa-tion, the liquid transport element 916 and the heating mem-ber 918 comprise a heating assembly 934, which, together with the base member 914 and a nozzle member 955, define a vaporization chamber 932. In the depicted implementation, the nozzle member 955 includes a central opening and is located proximate the base member 926 and below the heating member 918. In the depicted implementation, the nozzle member 955 is made of silicone rubber although other materials are possible, including, but not limited to, boron nitride (BN) rubber, natural rubber, thermoplastic polyurethane, or another resilient material. In the depicted implementation, the nozzle member 955 is also configured to act as a heat shield to protect the base member 926 from radiant heat from the heating member 918. It may also create an indirect air inlet flow path, block direct line of sight to the heating member 918 from outside of the cartridge 900, and/or help prevent aerosol particles from exiting through the air inlet channel 930. In other implementations, the nozzle member may be made of other materials, including, but not limited to, moldable plastic materials.

It should be noted that some implementations need not include a heating assembly, but, rather, may include an atomization assembly configured to generate an aerosol in another manner. Some examples of atomization assemblies that generate aerosols in other ways can be found, for example, in U.S. application Ser. No. 16/544,326, filed on Aug. 19, 2019, and titled Detachable Atomization Assembly for Aerosol Delivery Device, which is incorporated herein by reference in its entirety.

In the depicted implementation, the heating member 918 is made of 316L stainless steel, although other materials may be used including, but not limited to, 316, 304, or 304L stainless steel. In other implementations, the heating mem-ber may be made of a different material, such as, for example, Kanthal (FeCrAl), Nichrome, Molybdenum disi-licide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative tempera-ture coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radia-tion-trapping (e.g., a black body or a white body). Suitable microheaters are described in U.S. Pat. No. 8,881,737 to Collett et al., which is incorporated herein by reference in its entirety. Microheaters, for example, can comprise a sub-strate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. Other heaters are described in U.S. Pat. App. Pub. No. 2016/0345633 to DePiano et al., which is incorporated herein by reference in its entirety.

Although in other implementations additional and/or dif-fering contact features may be provided, the heating member 918 of the depicted implementation includes a pair of contact holes that are configured to connect the heating member 918 to the heater connectors 920A, 920B of the cartridge 900. In depicted implementation, the heater con-nectors 920A, 920B are made of brass and are plated with gold over nickel. In other implementations, the heater con-nectors may be made of another conductive material that may or may not be plated. Examples of other possible conductive materials include, but are not limited to, copper, aluminum, platinum, gold, silver, iron, steel, bronze, graph-ite, conductive ceramic materials, and/or any combination thereof. In the depicted implementation, the heater connec-tors 920A, 920B are insert-molded into the bottom cap 926. Although other configurations are possible, in the depicted implementation the bottom surfaces of the heater connectors 920A, 920B are recessed with respect to the bottom surface of the bottom cap 926.

The bottom cap 926 of the depicted implementation is configured to be secured to the distal end of the tank 910 via an ultrasonic welding process; however, other attachment methods are possible (e.g., via adhesives, heat staking/ welding, snap-fit, etc.). In the depicted implementation, the bottom cap 926 of the cartridge 900 includes a cartridge air inlet channel 930, which is located in an approximate center of a bottom surface of the bottom cap 926. Although other configurations are possible, in the depicted implementation the cartridge air inlet channel 930 has an oval shape and includes a cross-bar feature that extends across the inlet between the opening of the air inlet channel 930 and the vaporization chamber 932.

Although other configurations are possible, the cartridge 900 of the depicted implementation also includes a pair of metal inserts 924A, 924B that are positioned in the bottom cap 926 and are configured to be exposed through the bottom surface thereof. In the depicted implementation, the metal inserts 924A, 924B are insert-molded into the bottom cap 926. In some implementations, the metal inserts may be configured for a press or snap fit connection with the bottom cap. In the depicted implementation, the metal inserts 924A, 924B are made of stainless steel plated with nickel; however, in other implementations the metal inserts may be made of any material configured to be attracted by a magnet, such as various ferromagnetic materials, including, but not limited, to iron, nickel, cobalt, alloys such as steel, and/or any combination thereof.

Airflow into a control device of one example implemen-tation of the present disclosure is illustrated in FIG. 35. In particular, FIG. 35 illustrates a side section view of a control device 800. As air is drawn into the control device 800 through a gap between an installed cartridge and the control device 800 as described above (such as, for example, between the cartridge and the top of the outer wall 804 of the housing 802 and/or between the cartridge and the upper frame 806), the air is drawn downward toward the bottom of the receiving chamber 830, wherein it enters the air intake opening 852. It should be noted that in various implementations, changes in the size and/or shape of the air intake opening and/or the gap between the cartridge and the control device may affect resistance to draw; thus, one or more of the related components may be designed to create a desired resistance. In the depicted implementation, air that enters the air intake opening 852 flows above the pressure sensor seal 810 (and pressure sensor 840) where it is directed into the cartridge through the upper frame 806, and cartridge intake seal 850) thereof.

Air and aerosol flow through a cartridge of one example implementation is illustrated in FIGS. 36, 37, and 38. In particular, FIG. 36 illustrates an angled side section view of a cartridge 900 showing air and aerosol flow; FIG. 37 illustrates an angled front section view of the cartridge 900; and FIG. 38 illustrates a bottom perspective view of the cartridge 900. As air is drawn through the inlet channel 930 (and around a cross-bar feature thereof) into the cartridge 900 of the depicted implementation, the pressure sensor may detect a draw by sensing a pressure drop in the cartridge 900. When a draw is detected by the pressure sensor, the control component directs current through the heating member 918 in order to heat the heating member 918. As the heating member 918 heats, at least a portion of the liquid composition contained in the liquid transport element 916 is vaporized in the vaporization chamber 932. Accordingly, aerosol produced in the vaporization chamber 932 may then directed to the user. In particular, as the air enters the cartridge 900 via the air inlet channel 930, the air travels through the vaporization chamber 932 where it impinges on the heating member 918 substantially perpendicularly thereto and mixes with the vaporized liquid composition to become the aerosol. Due to the geometry of the vaporization chamber 932, the bottom cap 926, and/or the base member 914, the aerosol is split into two separate paths that extend through the inside of the bottom cap 926, around the heater connectors 920A, 920B, and then through the aerosol flow tubes 933A, 933B that are defined on opposite sides of the reservoir cavity 928 of the tank 910. As shown in the figures, the two aerosol paths converge at the proximal end of the tank 910 and below the upper aerosol channel insert 906. The recombined aerosol then flows through the upper aerosol channel insert 906 and out of the exit portal 915 of the mouthpiece 900, to the user.

Although in some implementations a cartridge and a control device may be provided together as a complete aerosol delivery device generally, these components may be provided separately. For example, the present disclosure also encompasses a disposable unit for use with a reusable unit. In specific implementations, such a disposable unit (which may be a cartridge as illustrated in the appended figures) can be configured to engage a reusable unit (which may be a control device as illustrated in the appended figures). In still other configurations, a cartridge may comprise a reusable unit and a control device may comprise a disposable unit.

Although some figures described herein illustrate a cartridge and a control device in a working relationship, it is understood that the cartridge and the control device may exist as individual components. Accordingly, any discussion otherwise provided herein in relation to the components in combination also should be understood as applying to the control device and the cartridge as individual and separate components.

In another aspect, the present disclosure may be directed to kits that provide a variety of components as described herein. For example, a kit may comprise a control device with one or more cartridges. A kit may further comprise a control device with one or more charging components. A kit may further comprise a control device with one or more batteries. A kit may further comprise a control device with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control devices may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

a control device that includes an outer housing defining an outer wall and having a proximal end and a distal end, the proximal end of the control device defining a receiving chamber, the control device further including a power source and a control component; and a cartridge that includes a mouthpiece, a tank, and a heating assembly, the mouthpiece having a proximal end and a distal end, the proximal end of the mouthpiece having an exit portal defined therethrough, the tank being configured to contain a liquid composition, wherein the cartridge is configured to be removably coupled with the receiving chamber of the control device, wherein the heating assembly defines a vaporization chamber and is configured to heat the liquid composition to generate an aerosol, wherein an inlet airflow is defined by a gap between the cartridge and the control device, wherein the gap originates at an interface between an outer peripheral surface of the mouthpiece and the control device, wherein the gap is established by a plurality of protuberances located on the control device, and wherein the plurality of protuberances comprises a plurality of raised elongate bosses located on an upper frame of the control device.

2. The aerosol delivery device of claim 1, wherein the interface is located proximate an outer peripheral surface of the mouthpiece and a top edge of the outer wall of the housing.

3. The aerosol delivery device of claim 1, wherein the cartridge further includes a bottom cap, and wherein an inlet channel is located in the bottom cap.

4. The aerosol delivery device of claim 3, wherein inlet airflow enters the cartridge through a single inlet channel located in an approximate center of a bottom surface of the bottom cap.

5. The aerosol delivery device of claim 3, wherein the inlet channel located in the bottom cap has a nozzle-like shape.

6. The aerosol delivery device of claim 3, wherein the gap between the cartridge and the control device is established between the outer housing and the upper frame of the control device and the mouthpiece, tank, and bottom cap of the cartridge.

7. The aerosol delivery device of claim 1, wherein the heating assembly comprises a flat heating member and a liquid transport element, and wherein the flat heating member and the liquid transport element are installed in a curved orientation.

8. The aerosol delivery device of claim 3, wherein the vaporization chamber of the cartridge is defined by the bottom cap and heating assembly.

9. The aerosol delivery device of claim 1, wherein the tank further defines a reservoir cavity configured to hold the liquid composition.

10. The aerosol delivery device of claim 1, wherein an aerosol path is defined through an upper aerosol channel insert located between the tank and the exit portal of the mouthpiece.

11. The aerosol delivery device of claim 1, wherein the distal end of the bottom cap of the cartridge includes a pair of inserts comprising a ferromagnetic metal material.

12. The aerosol delivery device of claim 11, wherein the upper frame of the control device includes a pair of magnets configured to substantially align with the pair of metal inserts of the cartridge.

13. The aerosol delivery device of claim 1, wherein the control device includes a pressure sensor, and wherein the cartridge and the control device include a pressure path configured to signal a negative pressure to the pressure sensor.

14. The aerosol delivery device of claim 1, wherein an aerosol path originates at the vaporization chamber and is defined through the tank and the exit portal of the mouthpiece.

15. The aerosol delivery device of claim 1, wherein inlet air entering the vaporization chamber impinges on the heating member substantially perpendicularly thereto and spreads out substantially horizontally.

\* \* \* \* \*